(12) United States Patent
Reth et al.

(10) Patent No.: US 8,912,313 B2
(45) Date of Patent: Dec. 16, 2014

(54) VARIANTS OF THE PROMOTER OF THE GAP GENE CODING FOR GLYCERALDEHYDE-3-PHOSPHATE DEHYDROGENASE

(75) Inventors: Alexander Reth, Bielefeld (DE);
Brigitte Bathe, Salzkotten (DE);
Stephan Hans, Osnabrück (DE);
Wilfried Claes, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/534,359

(22) Filed: Jun. 27, 2012

(65) Prior Publication Data

US 2013/0004999 A1 Jan. 3, 2013

Related U.S. Application Data

(60) Provisional application No. 61/502,675, filed on Jun. 29, 2011.

(30) Foreign Application Priority Data

Jun. 28, 2011 (DE) .......................... 10 2011 118 019

(51) Int. Cl.
| | | |
|---|---|---|
| *C12N 15/11* | (2006.01) | |
| *C12N 15/77* | (2006.01) | |
| *C12N 9/02* | (2006.01) | |
| *C12P 13/08* | (2006.01) | |
| *C12P 13/10* | (2006.01) | |
| *C12P 13/04* | (2006.01) | |

(52) U.S. Cl.
CPC .............. *C12N 15/77* (2013.01); *C12N 9/0008* (2013.01); *C12P 13/08* (2013.01); *C12P 13/10* (2013.01); *C12P 13/04* (2013.01)
USPC ....................................................... 536/23.1

(58) Field of Classification Search
None
See application file for complete search history.

(56) References Cited

U.S. PATENT DOCUMENTS

| | | |
|---|---|---|
| 2004/0043458 A1 | 3/2004 | Bathe et al. |
| 2007/0026505 A1 | 2/2007 | Madden et al. |
| 2007/0259408 A1 | 11/2007 | Bathe et al. |
| 2008/0050786 A1 * | 2/2008 | Bathe et al. ................... 435/113 |
| 2008/0171371 A1 | 7/2008 | Yukawa et al. |
| 2010/0173368 A1 * | 7/2010 | Nakanishi et al. ............ 435/115 |
| 2010/0255544 A1 | 10/2010 | Bathe et al. |

FOREIGN PATENT DOCUMENTS

| | | |
|---|---|---|
| EP | 1 790 721 A1 | 5/2007 |
| WO | WO 03/014330 A2 | 2/2003 |
| WO | WO 03/014330 A3 | 2/2003 |
| WO | WO 2006/138689 A2 | 12/2006 |
| WO | WO 2006/138689 A3 | 12/2006 |

OTHER PUBLICATIONS

Patek et al., Journal of Biotechnology, 2003, vol. 104, pp. 311-323.*
International Search Report issued Sep. 21, 2012, in International Patent Application No. PCT/EP2012/062046.
Database Gensenq [Online], "DNA fragment containing a pomoter region SEQ ID No. 32.", XP002682941, Database accession No. AEG41826, May 18, 2006, 1 page.
Miroslav Patek, et al., "Promoters of *Corynebacterium glutamicum*", Journal of Biotechnology 104, Elsevier Science, XP002323247, Sep. 4, 2003, pp. 311-323.
Miroslav Patek, et al., "Function of *Corynebacterium glutamicum* promoters in *Escherichia coli, Streptomyces lividans,* and *Bacillus subtilis*", Journal of Biotechnology 104, Elsevier Science, XP002323103, Jan. 1, 20003, pp. 325-334.

* cited by examiner

*Primary Examiner* — Anne Gussow
*Assistant Examiner* — Mindy G Brown
(74) *Attorney, Agent, or Firm* — Oblon, Spivak, McClelland, Maier & Neustadt, L.L.P.

(57) ABSTRACT

The invention relates to an isolated polynucleotide having promoter activity, a variant of the promoter of the gap gene coding for glyceraldehyde-3-phosphate dehydrogenase; and to a microorganism which produces and/or secretes a fine chemical, the microorganism including the isolated polynucleotide having promoter activity, which enables various genes to be overexpressed in comparison with the particular starting strain; and to a process for preparing fine chemicals using the microorganism.

10 Claims, 5 Drawing Sheets

SEQUENCE LISTING

```
<160> NUMBER OF SEQ ID NOS: 50

<210> SEQ ID NO 1
<211> LENGTH: 484
<212> TYPE: DNA
<213> ORGANISM: Corynebacterium glutamicum ATCC13032
<220> FEATURE:
<221> NAME/KEY: misc_feature
```

```
<222> LOCATION: (1)..(484)
<223> OTHER INFORMATION: SEQ ID NO: 20 from US 2008/0050786
<220> FEATURE:
<221> NAME/KEY: misc_feature
<222> LOCATION: (247)..(346)
<223> OTHER INFORMATION: Sequence of the P-gap promoter according to
      (Journal of Biotechnology 104, 311-323 (2003))
<220> FEATURE:
<221> NAME/KEY: misc_feature
<222> LOCATION: (289)..(294)
<223> OTHER INFORMATION: -10 region of the P-gap promoter according to
      Patek et al.
<220> FEATURE:
<221> NAME/KEY: misc_feature
<222> LOCATION: (301)..(301)
<223> OTHER INFORMATION: Transcription initiation site
<220> FEATURE:
<221> NAME/KEY: misc_feature
<222> LOCATION: (363)..(363)
<223> OTHER INFORMATION: Guanine nucleobase
<220> FEATURE:
<221> NAME/KEY: RBS
<222> LOCATION: (473)..(478)
<223> OTHER INFORMATION: Ribosome binding site

<400> SEQUENCE: 1
ttgaagccta aaaacgaccg agcctattgg gattaccatt gaagccagtg tgagttgcat      60
cacattggct tcaaatctga gactttaatt tgtggattca cggggtgta  atgtagttca     120 taattaaccc cattcggggg agcagatcgt agtgcgaacg atttcaggtt cgttccctgc    180
aaaaactatt tagcgcaagt gttggaaatg ccccgtttg  gggtcaatgt ccattttga    240 atgtgtctgt atgattttgc atctgctgcg aaatctttgt ttccccgcta agttgagga    300 caggttgaca cggagttgac tcgacgaatt atccaatgtg agtaggtttg gtgcgtgagt   360
tggaaaaatt cgccatactc gcccttgggt tctgtcagct caagaattct tgagtgaccg   420
atgctctgat tgacctaact gcttgacaca ttgcatttcc tacaatcttt agaggagaca   480
caac                                                                484

<210> SEQ ID NO 2
<211> LENGTH: 461
<212> TYPE: DNA
<213> ORGANISM: Corynebacterium glutamicum ATCC13032
<220> FEATURE:
<221> NAME/KEY: promoter
<222> LOCATION: (1)..(461)
<220> FEATURE:
<221> NAME/KEY: misc_feature
<222> LOCATION: (362)..(362)
<223> OTHER INFORMATION: Guanine (g) nucleobase

<400> SEQUENCE: 2
tgaagcctaa aaacgaccga gcctattggg attaccattg aagccagtgt gagttgcatc     60
acattggctt caaatctgag actttaattt gtggattcac ggggtgtaa tgtagttcat    120 aattaacccc attcgggga gcagatcgta gtgcgaacga tttcaggttc gttccctgca    180
aaaactattt agcgcaagtg ttggaaatgc cccgtttgg ggtcaatgtc cattttgaa     240 tgtgtctgta tgattttgca tctgctgcga aatctttgtt tccccgctaa agttgaggac    300
aggttgacac ggagttgact cgacgaatta tccaatgtga gtaggtttgg tgcgtgagtt    360
ggaaaaattc gccatactcg cccttgggtt ctgtcagctc aagaattctt gagtgaccga   420
tgctctgatt gacctaactg cttgacacat tgcatttcct a                        461

<210> SEQ ID NO 3
<211> LENGTH: 461
```

```
<212> TYPE: DNA
<213> ORGANISM: Corynebacterium glutamicum ATCC13032
<220> FEATURE:
<221> NAME/KEY: promoter
<222> LOCATION: (1)..(461)
<220> FEATURE:
<221> NAME/KEY: mutation
<222> LOCATION: (362)..(362)
<223> OTHER INFORMATION: Adenine nucleobase (a)

<400> SEQUENCE: 3
tgaagcctaa aaacgaccga gcctattggg attaccattg aagccagtgt gagttgcatc      60
acattggctt caaatctgag actttaattt gtggattcac gggggtgtaa tgtagttcat     120
aattaacccc attcggggga gcagatcgta gtgcgaacga tttcaggttc gttccctgca     180
aaaactattt agcgcaagtg ttggaaatgc cccgtttgg ggtcaatgtc cattttgaa      240 tgtgtctgta tgattttgca tctgctgcga aatctttgtt tccccgctaa agttgaggac     300
aggttgacac ggagttgact cgacgaatta tccaatgtga gtaggtttgg tgcgtgagtt     360
gaaaaaattc gccatactcg cccttgggtt ctgtcagctc aagaattctt gagtgaccga     420
tgctctgatt gacctaactg cttgacacat tgcatttcct a                         461

<210> SEQ ID NO 4
<211> LENGTH: 10
<212> TYPE: DNA
<213> ORGANISM: Corynebacterium glutamicum
<220> FEATURE:
<221> NAME/KEY: RBS
<222> LOCATION: (1)..(10)
<223> OTHER INFORMATION: Shine-Dalgarno sequence according to
      (Microbiology, 145, 915-924 (1999))

<400> SEQUENCE: 4
agaaaggagg                                                            10

<210> SEQ ID NO 5
<211> LENGTH: 9
<212> TYPE: DNA
<213> ORGANISM: Corynebacterium glutamicum
<220> FEATURE:
<221> NAME/KEY: RBS
<222> LOCATION: (1)..(9)
<223> OTHER INFORMATION: Shine-Dalgarno sequence according to (Journal
      of Biotechnology 104, 41-53 (2003))

<400> SEQUENCE: 5 gaaaggagg                                                              9

<210> SEQ ID NO 6
<211> LENGTH: 9
<212> TYPE: DNA
<213> ORGANISM: Corynebacterium glutamicum
<220> FEATURE:
<221> NAME/KEY: RBS
<222> LOCATION: (1)..(9)
<223> OTHER INFORMATION: Ribosome binding site of the ppc gene according
      to (Gene 77, 237-251 (1989))

<400> SEQUENCE: 6 gaaagagtg                                                              9

<210> SEQ ID NO 7
<211> LENGTH: 7
<212> TYPE: DNA
<213> ORGANISM: Corynebacterium glutamicum
<220> FEATURE:
```

```
<221> NAME/KEY: RBS
<222> LOCATION: (1)..(7)
<223> OTHER INFORMATION: Ribosome binding site of the aceA gene
      according to (Journal of Bacteriology 176 (12), 3474-3483 (1994))

<400> SEQUENCE: 7 aaggaag                                                                  7

<210> SEQ ID NO 8
<211> LENGTH: 7
<212> TYPE: DNA
<213> ORGANISM: Corynebacterium glutamicum
<220> FEATURE:
<221> NAME/KEY: RBS
<222> LOCATION: (1)..(7)
<223> OTHER INFORMATION: Ribosome binding site of the thiX gene
      according to (Journal of Bacteriology 176 (12), 3474-3483 (1994))

<400> SEQUENCE: 8 gaaagga                                                                  7

<210> SEQ ID NO 9
<211> LENGTH: 7
<212> TYPE: DNA
<213> ORGANISM: Corynebacterium glutamicum
<220> FEATURE:
<221> NAME/KEY: RBS
<222> LOCATION: (1)..(7)
<223> OTHER INFORMATION: Ribosome binding site of the sod gene according
      to WO2005/059144

<400> SEQUENCE: 9 gaaagga                                                                  7

<210> SEQ ID NO 10
<211> LENGTH: 7
<212> TYPE: DNA
<213> ORGANISM: Corynebacterium glutamicum
<220> FEATURE:
<221> NAME/KEY: RBS
<222> LOCATION: (1)..(7)
<223> OTHER INFORMATION: Ribosome binding site of the tuf gene according
      to WO2005/059093

<400> SEQUENCE: 10 aggagga                                                                  7

<210> SEQ ID NO 11
<211> LENGTH: 7
<212> TYPE: DNA
<213> ORGANISM: Corynebacterium glutamicum
<220> FEATURE:
<221> NAME/KEY: RBS
<222> LOCATION: (1)..(7)
<223> OTHER INFORMATION: Ribosome binding site according to SEQ ID NO:44
      of EP 1 918 378 A1

<400> SEQUENCE: 11 gaaagga                                                                  7

<210> SEQ ID NO 12
<211> LENGTH: 7
<212> TYPE: DNA
<213> ORGANISM: Corynebacterium glutamicum
<220> FEATURE:
<221> NAME/KEY: RBS
<222> LOCATION: (1)..(7)
<223> OTHER INFORMATION: Ribosome binding site of the fbp gene
```

```
<400> SEQUENCE: 12 gaggagg                                                                    7

<210> SEQ ID NO 13
<211> LENGTH: 6
<212> TYPE: DNA
<213> ORGANISM: Corynebacterium glutamicum
<220> FEATURE:
<221> NAME/KEY: RBS
<222> LOCATION: (1)..(6)
<223> OTHER INFORMATION: Ribosome binding site of the gap gene according
      to (Journal of Bacteriology 174 (19), 6076-6086 (1992))

<400> SEQUENCE: 13 aggaga                                                                     6

<210> SEQ ID NO 14
<211> LENGTH: 22
<212> TYPE: DNA
<213> ORGANISM: Corynebacterium glutamicum
<220> FEATURE:
<221> NAME/KEY: RBS
<222> LOCATION: (11)..(16)
<223> OTHER INFORMATION: Ribosome binding site of the gap gene

<400> SEQUENCE: 14
caatctttag aggagacaca ac                                                  22

<210> SEQ ID NO 15
<211> LENGTH: 22
<212> TYPE: DNA
<213> ORGANISM: Corynebacterium glutamicum
<220> FEATURE:
<221> NAME/KEY: misc_feature
<222> LOCATION: (2)..(7)
<223> OTHER INFORMATION: SspI cleavage site
<220> FEATURE:
<221> NAME/KEY: RBS
<222> LOCATION: (11)..(16)
<223> OTHER INFORMATION: Ribosome binding site of the gap gene

<400> SEQUENCE: 15
caatatttag aggagacaca ac                                                  22

<210> SEQ ID NO 16
<211> LENGTH: 21
<212> TYPE: DNA
<213> ORGANISM: Corynebacterium glutamicum
<220> FEATURE:
<221> NAME/KEY: misc_feature
<222> LOCATION: (4)..(8)
<223> OTHER INFORMATION: Region of the NruI cleavage site
<220> FEATURE:
<221> NAME/KEY: mutation
<222> LOCATION: (7)..(7)
<223> OTHER INFORMATION: Cytosine (c) nucleotide deletion
<220> FEATURE:
<221> NAME/KEY: RBS
<222> LOCATION: (10)..(15)
<223> OTHER INFORMATION: Ribosomenbindestelle des Gens gap

<400> SEQUENCE: 16
caatcggaga ggagacacaa c                                                   21

<210> SEQ ID NO 17
<211> LENGTH: 22
<212> TYPE: DNA
<213> ORGANISM: Corynebacterium glutamicum
<220> FEATURE:
```

```
<221> NAME/KEY: misc_feature
<222> LOCATION: (4)..(9)
<223> OTHER INFORMATION: NruI cleavage site
<220> FEATURE:
<221> NAME/KEY: RBS
<222> LOCATION: (11)..(16)
<223> OTHER INFORMATION: Ribosome binding site of the gap gene

<400> SEQUENCE: 17
caatcgcgag aggagacaca ac                                          22

<210> SEQ ID NO 18
<211> LENGTH: 22
<212> TYPE: DNA
<213> ORGANISM: Corynebacterium glutamicum
<220> FEATURE:
<221> NAME/KEY: misc_feature
<222> LOCATION: (4)..(9)
<223> OTHER INFORMATION: NruI cleavage site
<220> FEATURE:
<221> NAME/KEY: RBS
<222> LOCATION: (8)..(14)
<223> OTHER INFORMATION: Ribosome binding site of the gap gene

<400> SEQUENCE: 18
caatcgcgag gaggcccttc ag                                          22

<210> SEQ ID NO 19
<211> LENGTH: 1266
<212> TYPE: DNA
<213> ORGANISM: Corynebacterium glutamicum
<220> FEATURE:
<221> NAME/KEY: CDS
<222> LOCATION: (1)..(1266)
<223> OTHER INFORMATION: lysC coding region

<400> SEQUENCE: 19 gtg gcc ctg gtc gta cag aaa tat ggc ggt tcc tcg ctt gag agt gcg    48
Val Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct    96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat   144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt   192
Glu Leu Leu Glu Leu Ala Ala Ala Val Asn Pro Val Pro Pro Ala Arg
    50                  55                  60 gaa atg gat atg ctc ctg act gct ggt gag cgt att tct aac gct ctc   240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg   288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc   336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc   384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc   432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg   480
Asp Val Thr Thr Leu Gly Arg Gly Gly Ser Asp Thr Thr Ala Val Ala
```

```
                Asp Val Thr Thr Leu Gly Arg Gly Gly Ser Asp Thr Thr Ala Val Ala
                145                 150                 155                 160 ttg gca gct gct ttg aac gct gat gtg tgt gag att tac tcg gac gtt             528
Leu Ala Ala Ala Leu Asn Ala Asp Val Cys Glu Ile Tyr Ser Asp Val
                    165                 170                 175 gac ggt gtg tat acc gct gac ccg cgc atc gtt cct aat gca cag aag             576
Asp Gly Val Tyr Thr Ala Asp Pro Arg Ile Val Pro Asn Ala Gln Lys
                180                 185                 190 ctg gaa aag ctc agc ttc gaa gaa atg ctg gaa ctt gct gct gtt ggc             624
Leu Glu Lys Leu Ser Phe Glu Glu Met Leu Glu Leu Ala Ala Val Gly
            195                 200                 205 tcc aag att ttg gtg ctg cgc agt gtt gaa tac gct cgt gca ttc aat             672
Ser Lys Ile Leu Val Leu Arg Ser Val Glu Tyr Ala Arg Ala Phe Asn
        210                 215                 220 gtg cca ctt cgc gta cgc tcg tct tat agt aat gat ccc ggc act ttg             720
Val Pro Leu Arg Val Arg Ser Ser Tyr Ser Asn Asp Pro Gly Thr Leu
    225                 230                 235                 240 att gcc ggc tct atg gag gat att cct gtg gaa gaa gca gtc ctt acc             768
Ile Ala Gly Ser Met Glu Asp Ile Pro Val Glu Glu Ala Val Leu Thr
                    245                 250                 255 ggt gtc gca acc gac aag tcc gaa gcc aaa gta acc gtt ctg ggt att             816
Gly Val Ala Thr Asp Lys Ser Glu Ala Lys Val Thr Val Leu Gly Ile
                260                 265                 270 tcc gat aag cca ggc gag gct gcg aag gtt ttc cgt gcg ttg gct gat             864
Ser Asp Lys Pro Gly Glu Ala Ala Lys Val Phe Arg Ala Leu Ala Asp
            275                 280                 285 gca gaa atc aac att gac atg gtt ctg cag aac gtc tct tct gta gaa             912
Ala Glu Ile Asn Ile Asp Met Val Leu Gln Asn Val Ser Ser Val Glu
        290                 295                 300 gac ggc acc acc gac atc acc ttc acc tgc cct cgt tcc gac ggc cgc             960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc            1008
Arg Ala Met Glu Ile Leu Lys Lys Leu Gln Val Gln Gly Asn Trp Thr
                    325                 330                 335 aat gtg ctt tac gac gac cag gtc ggc aaa gtc tcc ctc gtg ggt gct            1056
Asn Val Leu Tyr Asp Asp Gln Val Gly Lys Val Ser Leu Val Gly Ala
                340                 345                 350 ggc atg aag tct cac cca ggt gtt acc gca gag ttc atg gaa gct ctg            1104
Gly Met Lys Ser His Pro Gly Val Thr Ala Glu Phe Met Glu Ala Leu
            355                 360                 365 cgc gat gtc aac gtg aac atc gaa ttg att tcc acc tct gag att cgt            1152
Arg Asp Val Asn Val Asn Ile Glu Leu Ile Ser Thr Ser Glu Ile Arg
        370                 375                 380 att tcc gtg ctg atc cgt gaa gat gat ctg gat gct gct gca cgt gca            1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat            1248
Leu His Glu Gln Phe Gln Leu Gly Gly Glu Asp Glu Ala Val Val Tyr
                    405                 410                 415 gca ggc acc gga cgc taa                                                    1266
Ala Gly Thr Gly Arg
            420

<210> SEQ ID NO 20
<211> LENGTH: 421
<212> TYPE: PRT
<213> ORGANISM: Corynebacterium glutamicum

<400> SEQUENCE: 20
```

-continued

```
Val Ala Leu Val Val Gln Lys Tyr Gly Gly Ser Ser Leu Glu Ser Ala
 1               5                  10                  15
Glu Arg Ile Arg Asn Val Ala Glu Arg Ile Val Ala Thr Lys Lys Ala
            20                  25                  30
Gly Asn Asp Val Val Val Cys Ser Ala Met Gly Asp Thr Thr Asp
            35                  40                  45
Glu Leu Leu Glu Leu Ala Ala Val Asn Pro Val Pro Pro Ala Arg
 50                  55                  60
Glu Met Asp Met Leu Leu Thr Ala Gly Glu Arg Ile Ser Asn Ala Leu
 65                  70                  75                  80
Val Ala Met Ala Ile Glu Ser Leu Gly Ala Glu Ala Gln Ser Phe Thr
                85                  90                  95
Gly Ser Gln Ala Gly Val Leu Thr Thr Glu Arg His Gly Asn Ala Arg
            100                 105                 110
Ile Val Asp Val Thr Pro Gly Arg Val Arg Glu Ala Leu Asp Glu Gly
            115                 120                 125
Lys Ile Cys Ile Val Ala Gly Phe Gln Gly Val Asn Lys Glu Thr Arg
130                 135                 140
Asp Val Thr Thr Leu Gly Arg Gly Gly Ser Asp Thr Thr Ala Val Ala
145                 150                 155                 160
Leu Ala Ala Ala Leu Asn Ala Asp Val Cys Glu Ile Tyr Ser Asp Val
                165                 170                 175
Asp Gly Val Tyr Thr Ala Asp Pro Arg Ile Val Pro Asn Ala Gln Lys
            180                 185                 190
Leu Glu Lys Leu Ser Phe Glu Glu Met Leu Glu Leu Ala Ala Val Gly
            195                 200                 205
Ser Lys Ile Leu Val Leu Arg Ser Val Glu Tyr Ala Arg Ala Phe Asn
210                 215                 220
Val Pro Leu Arg Val Arg Ser Ser Tyr Ser Asn Asp Pro Gly Thr Leu
225                 230                 235                 240
Ile Ala Gly Ser Met Glu Asp Ile Pro Val Glu Glu Ala Val Leu Thr
                245                 250                 255
Gly Val Ala Thr Asp Lys Ser Glu Ala Lys Val Thr Val Leu Gly Ile
            260                 265                 270
Ser Asp Lys Pro Gly Glu Ala Ala Lys Val Phe Arg Ala Leu Ala Asp
            275                 280                 285
Ala Glu Ile Asn Ile Asp Met Val Leu Gln Asn Val Ser Ser Val Glu
            290                 295                 300
Asp Gly Thr Thr Asp Ile Thr Phe Thr Cys Pro Arg Ser Asp Gly Arg
305                 310                 315                 320
Arg Ala Met Glu Ile Leu Lys Lys Leu Gln Val Gln Gly Asn Trp Thr
                325                 330                 335
Asn Val Leu Tyr Asp Asp Gln Val Gly Lys Val Ser Leu Val Gly Ala
            340                 345                 350
Gly Met Lys Ser His Pro Gly Val Thr Ala Glu Phe Met Glu Ala Leu
            355                 360                 365
Arg Asp Val Asn Val Asn Ile Glu Leu Ile Ser Thr Ser Glu Ile Arg
            370                 375                 380
Ile Ser Val Leu Ile Arg Glu Asp Asp Leu Asp Ala Ala Ala Arg Ala
385                 390                 395                 400
Leu His Glu Gln Phe Gln Leu Gly Gly Glu Asp Glu Ala Val Val Tyr
                405                 410                 415
Ala Gly Thr Gly Arg
```

-continued

420

<210> SEQ ID NO 21
<211> LENGTH: 1266
<212> TYPE: DNA
<213> ORGANISM: Corynebacterium glutamicum
<220> FEATURE:
<221> NAME/KEY: CDS
<222> LOCATION: (1)..(1266)
<223> OTHER INFORMATION: lysC coding region
<220> FEATURE:
<221> NAME/KEY: mutation
<222> LOCATION: (932)..(932)
<223> OTHER INFORMATION: T311I mutation; cytosine (c) nucleobase to
    thymine (t)

<400> SEQUENCE: 21

| | | | | | | | | | | | | | | | |
|---|---|---|---|---|---|---|---|---|---|---|---|---|---|---|---|
| gtg | gcc | ctg | gtc | gta | cag | aaa | tat | ggc | ggt | tcc | tcg | ctt | gag | agt | gcg | 48 |
| Val | Ala | Leu | Val | Val | Gln | Lys | Tyr | Gly | Gly | Ser | Ser | Leu | Glu | Ser | Ala | |
| 1 | | | | 5 | | | | | 10 | | | | | 15 | | | gaa cgc att aga aac gtc gct gaa cgg atc gtt gcc acc aag aag gct    96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat    144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt    192
Glu Leu Leu Glu Leu Ala Ala Ala Val Asn Pro Val Pro Pro Ala Arg
50                  55                  60 gaa atg gat atg ctc ctg act gct ggt gag cgt att tct aac gct ctc    240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg    288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc    336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc    384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc    432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg    480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt    528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag    576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc    624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat    672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg    720
Val Pro Leu Arg Val Arg Ser Ser Tyr Ser Asn Asp Pro Gly Thr Leu
225                 230                 235                 240

```
att gcc ggc tct atg gag gat att cct gtg gaa gaa gca gtc ctt acc      768
Ile Ala Gly Ser Met Glu Asp Ile Pro Val Glu Glu Ala Val Leu Thr
            245                 250                 255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
        260                 265                 270 tcc gat aag cca ggc gag gct gcg aag gtt ttc cgt gcg ttg gct gat      864
Ser Asp Lys Pro Gly Glu Ala Ala Lys Val Phe Arg Ala Leu Ala Asp
    275                 280                 285 gca gaa atc aac att gac atg gtt ctg cag aac gtc tct tct gta gaa      912
Ala Glu Ile Asn Ile Asp Met Val Leu Gln Asn Val Ser Ser Val Glu
290                 295                 300 gac ggc acc acc gac atc atc ttc acc tgc cct cgt tcc gac ggc cgc      960
Asp Gly Thr Thr Asp Ile Ile Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc taa                                             1266
Ala Gly Thr Gly Arg
            420

<210> SEQ ID NO 22
<211> LENGTH: 421
<212> TYPE: PRT
<213> ORGANISM: Corynebacterium glutamicum

<400> SEQUENCE: 22

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125
```

Lys Ile Cys Ile Val Ala Gly Phe Gln Gly Val Asn Lys Glu Thr Arg
            130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 23
<211> LENGTH: 2324
<212> TYPE: DNA
<213> ORGANISM: Corynebacterium glutamicum
<220> FEATURE:
<221> NAME/KEY: gene
<222> LOCATION: (1)..(1266)
<223> OTHER INFORMATION: lysC coding region
<220> FEATURE:
<221> NAME/KEY: mutation
<222> LOCATION: (932)..(932)
<223> OTHER INFORMATION: T311I, c to t
<220> FEATURE:
<221> NAME/KEY: gene
<222> LOCATION: (1290)..(2324)
<223> OTHER INFORMATION: asd coding region

<400> SEQUENCE: 23
gtggccctgg tcgtacagaa atatggcggt tcctcgcttg agagtgcgga acgcattaga    60

```
aacgtcgctg aacggatcgt tgccaccaag aaggctggaa atgatgtcgt ggttgtctgc    120
tccgcaatgg gagacaccac ggatgaactt ctagaacttg cagcggcagt gaatcccgtt    180
ccgccagctc gtgaaatgga tatgctcctg actgctggtg agcgtatttc taacgctctc    240
gtcgccatgg ctattgagtc ccttggcgca gaagcccaat cttttcacggg ctctcaggct    300 ggtgtgctca ccaccgagcg ccacggaaac gcacgcattg ttgatgtcac tccaggtcgt    360
gtgcgtgaag cactcgatga gggcaagatc tgcattgttg ctggtttcca gggtgttaat    420
aaagaaaccc gcgatgtcac cacgttgggt cgtggtggtt ctgacaccac tgcagttgcg    480
ttggcagctg ctttgaacgc tgatgtgtgt gagatttact cggacgttga cggtgtgtat    540
accgctgacc cgcgcatcgt tcctaatgca cagaagctgg aaaagctcag cttcgaagaa    600
atgctggaac ttgctgctgt tggctccaag attttggtgc tgcgcagtgt tgaatacgct    660
cgtgcattca atgtgccact tcgcgtacgc tcgtcttata gtaatgatcc cggcactttg    720
attgccggct ctatggagga tattcctgtg aagaagcag tccttaccgg tgtcgcaacc     780
gacaagtccg aagccaaagt aaccgttctg ggtatttccg ataagccagg cgaggctgcg    840
aaggttttcc gtgcgttggc tgatgcagaa atcaacattg acatggttct gcagaacgtc    900
tcttctgtag aagacggcac caccgacatc atcttcacct gccctcgttc cgacggccgc    960
cgcgcgatgg agatcttgaa gaagcttcag gttcagggca actggaccaa tgtgctttac   1020
gacgaccagg tcggcaaagt ctccctcgtg ggtgctggca tgaagtctca cccaggtgtt   1080
accgcagagt tcatggaagc tctgcgcgat gtcaacgtga acatcgaatt gatttccacc   1140
tctgagattc gtatttccgt gctgatccgt gaagatgatc tggatgctgc tgcacgtgca   1200
ttgcatgagc agttccagct gggcggcgaa gacgaagccg tcgtttatgc aggcaccgga   1260
cgctaaagtt ttaaaggagt agttttacaa tgaccaccat cgcagttgtt ggtgcaaccg   1320
gccaggtcgg ccaggttatg cgcacccttt tggaagagcg caatttccca gctgacactg   1380
ttcgtttctt tgcttcccca cgttccgcag gccgtaagat tgaattccgt ggcacggaaa   1440
tcgaggtaga agacattact caggcaaccg aggagtccct caaggacatc gacgttgcgt   1500
tgttctccgc tggaggcacc gcttccaagc agtacgctcc actgttcgct gctgcaggcg   1560
cgactgttgt ggataactct tctgcttggc gcaaggacga cgaggttcca ctaatcgtct   1620
ctgaggtgaa cccttccgac aaggattccc tggtcaaggg cattattgcg aaccctaact   1680
gcaccaccat ggctgcgatg ccagtgctga agccacttca cgatgccgct ggtcttgtaa   1740
agcttcacgt ttcctcttac caggctgttt ccggttctgg tcttgcaggt gtggaaacct   1800
tggcaaagca ggttgctgca gttggagacc acaacgttga gttcgtccat gatggacagg   1860
ctgctgacgc aggcgatgtc ggaccttatg tttcaccaat cgcttacaac gtgctgccat   1920
tcgccggaaa cctcgtcgat gacggcacct tcgaaaccga tgaagagcag aagctgcgca   1980
acgaatcccg caagattctc ggtctcccag acctcaaggt ctcaggcacc tgcgtccgcg   2040
tgccggtttt caccggccac acgctgacca ttcacgccga attcgacaag gcaatcaccg   2100
tggaccaggc gcaggagatc ttgggtgccg cttcaggcgt caagcttgtc gacgtcccaa   2160
ccccacttgc agctgccggc attgacgaat ccctcgttgg acgcatccgt caggactcca   2220
ctgtcgacga taaccgcggt ctggttctcg tcgtatctgg cgacaacctc cgcaagggtg   2280
ctgcgctaaa caccatccag atcgctgagc tgctggttaa gtaa                   2324
```

<210> SEQ ID NO 24

```
<211> LENGTH: 1266
<212> TYPE: DNA
<213> ORGANISM: Corynebacterium glutamicum
<220> FEATURE:
<221> NAME/KEY: mutation
<222> LOCATION: (1)..(1)
<223> OTHER INFORMATION: guanine (g) nucleobase to adenine (a)
<220> FEATURE:
<221> NAME/KEY: gene
<222> LOCATION: (1)..(1266)
<223> OTHER INFORMATION: lysC coding region
<220> FEATURE:
<221> NAME/KEY: mutation
<222> LOCATION: (932)..(932)
<223> OTHER INFORMATION: T311I mutation; cytosine (c) nucleobase to
      thymine (t)
<220> FEATURE:
<221> NAME/KEY: mutation
<222> LOCATION: (1265)..(1265)
<223> OTHER INFORMATION: adenine (a) nucleobase to guanine (g)

<400> SEQUENCE: 24
atggccctgg tcgtacagaa atatggcggt tcctcgcttg agagtgcgga acgcattaga      60
aacgtcgctg aacggatcgt tgccaccaag aaggctggaa atgatgtcgt ggttgtctgc     120
tccgcaatgg gagacaccac ggatgaactt ctagaacttg cagcggcagt gaatcccgtt     180
ccgccagctc gtgaaatgga tatgctcctg actgctggtg agcgtatttc taacgctctc     240
gtcgccatgg ctattgagtc ccttggcgca gaagcccaat cttcacgggc tctcaggct      300 ggtgtgctca ccaccgagcg ccacggaaac gcacgcattg ttgatgtcac tccaggtcgt     360
gtgcgtgaag cactcgatga gggcaagatc tgcattgttg ctggtttcca gggtgttaat     420
aaagaaaccc gcgatgtcac cacgttgggt cgtggtggtt ctgacaccac tgcagttgcg     480
ttggcagctg ctttgaacgc tgatgtgtgt gagatttact cggacgttga cggtgtgtat     540
accgctgacc cgcgcatcgt tcctaatgca cagaagctgg aaaagctcag cttcgaagaa     600
atgctggaac ttgctgctgt tggctccaag atttggtgc tgcgcagtgt tgaatacgct     660
cgtgcattca atgtgccact tcgcgtacgc tcgtcttata gtaatgatcc cggcactttg     720
attgccggct ctatggagga tattcctgtg aagaagcag tccttaccgg tgtcgcaacc     780
gacaagtccg aagccaaagt aaccgttctg ggtatttccg ataagccagg cgaggctgcg     840
aaggttttcc gtgcgttggc tgatgcagaa atcaacattg acatggttct gcagaacgtc     900
tcttctgtag aagacggcac caccgacatc atcttcacct gccctcgttc cgacggccgc     960
cgcgcgatgg agatcttgaa gaagcttcag gttcagggca actggaccaa tgtgctttac    1020
gacgaccagg tcgcaaagt ctccctcgtg gtgctggca tgaagtctca cccaggtgtt    1080
accgcagagt tcatggaagc tctgcgcgat gtcaacgtga acatcgaatt gatttccacc    1140
tctgagattc gtatttccgt gctgatccgt gaagatgatc tggatgctgc tgcacgtgca    1200
ttgcatgagc agttccagct gggcggcgaa gacgaagccg tcgtttatgc aggcaccgga    1260
cgctga                                                             1266

<210> SEQ ID NO 25
<211> LENGTH: 2808
<212> TYPE: DNA
<213> ORGANISM: Corynebacterium glutamicum
<220> FEATURE:
<221> NAME/KEY: misc_feature
<222> LOCATION: (1)..(6)
<223> OTHER INFORMATION: Region of the NsiI cleavage site
<220> FEATURE:
<221> NAME/KEY: promoter
<222> LOCATION: (7)..(467)
```

```
<223> OTHER INFORMATION: Pgap3 promoter according to SEQ ID No. 3
<220> FEATURE:
<221> NAME/KEY: misc_feature
<222> LOCATION: (468)..(488)
<223> OTHER INFORMATION: gap RBS according to SEQ ID No. 16
<220> FEATURE:
<221> NAME/KEY: gene
<222> LOCATION: (489)..(1754)
<223> OTHER INFORMATION: lysC coding region with T311I mutation, atg
      start and tga stop according to SEQ ID No. 24
<220> FEATURE:
<221> NAME/KEY: misc_feature
<222> LOCATION: (1755)..(1773)
<223> OTHER INFORMATION: RBS gap according to SEQ ID No. 26
<220> FEATURE:
<221> NAME/KEY: gene
<222> LOCATION: (1774)..(2808)
<223> OTHER INFORMATION: asd coding region

<400> SEQUENCE: 25
atgcattgaa gcctaaaaac gaccgagcct attgggatta ccattgaagc cagtgtgagt      60
tgcatcacat tggcttcaaa tctgagactt taatttgtgg attcacgggg gtgtaatgta     120
gttcataatt aaccccattc gggggagcag atcgtagtgc gaacgatttc aggttcgttc     180
cctgcaaaaa ctatttagcg caagtgttgg aaatgccccc gtttgggggtc aatgtccatt     240 tttgaatgtg tctgtatgat tttgcatctg ctgcgaaatc tttgtttccc cgctaaagtt     300
gaggacaggt tgacacggag ttgactcgac gaattatcca atgtgagtag gtttggtgcg     360
tgagttgaaa aaattcgcca tactcgccct tgggttctgt cagctcaaga attcttgagt     420
gaccgatgct ctgattgacc taactgcttg acacattgca tttcctacaa tcggagagga     480
gacacaacat ggccctggtc gtacagaaat atggcggttc ctcgcttgag agtgcggaac     540
gcattagaaa cgtcgctgaa cggatcgttg ccaccaagaa ggctggaaat gatgtcgtgg     600
ttgtctgctc cgcaatggga gacaccacgg atgaacttct ggaacttgca gcggcagtga     660
atcccgttcc gccagctcgt gaaatggata tgctcctgac tgctggtgag cgtatttcta     720
acgctctcgt cgccatggct attgagtccc ttggcgcaga gcccaatct ttcacgggct     780 ctcaggctgg tgtgctcacc accgagcgcc acggaaacgc acgcattgtt gatgtcactc     840
caggtcgtgt gcgtgaagca ctcgatgagg gcaagatctg cattgttgct ggtttccagg     900
gtgttaataa agaaacccgc gatgtcacca cgttgggtcg tggtggttct gacaccactg     960
cagttgcgtt ggcagctgct ttgaacgctg atgtgtgtga atttactcg gacgttgacg    1020 gtgtgtatac cgctgacccg cgcatcgttc ctaatgcaca gaagctggaa agctcagct    1080 tcgaagaaat gctggaactt gctgctgttg gctccaagat tttggtgctg cgcagtgttg    1140
aatacgctcg tgcattcaat gtgccacttc gcgtacgctc gtcttatagt aatgatcccg    1200
gcactttgat tgccggctct atggaggata ttcctgtgga agaagcagtc cttaccggtg    1260
tcgcaaccga caagtccgaa gccaaagtaa ccgttctggg tatttccgat aagccaggcg    1320
aggctgcgaa ggttttccgt gcgttggctg atgcagaaat caacattgac atggttctgc    1380
agaacgtctc ttctgtagaa gacggcacca ccgacatcat cttcacctgc cctcgttccg    1440
acggccgccg cgcgatggag atcttgaaga agcttcaggt tcagggcaac tggaccaatg    1500
tgctttacga cgaccaggtc ggcaaagtct ccctcgtggg tgctggcatg aagtctcacc    1560
caggtgttac cgcagagttc atggaagctc tgcgcgatgt caacgtgaac atcgaattga    1620
tttccaccct cgagattcgt atttccgtgc tgatccgtga agatgatctg gatgctgctg    1680
cacgtgcatt gcatgagcag ttccagctgg gcggcgaaga cgaagccgtc gtttatgcag    1740
```

```
gcaccggacg ctgacgtcta gaggagacac aacatgacca ccatcgcagt tgttggtgca    1800
accggccagg tcggccaggt tatgcgcacc cttttggaag agcgcaattt cccagctgac    1860
actgttcgtt tctttgcttc cccacgttcc gcaggccgta agattgaatt ccgtggcacg    1920
gaaatcgagg tagaagacat tactcaggca accgaggagt ccctcaagga catcgacgtt    1980
gcgttgttct ccgctggagg caccgcttcc aagcagtacg ctccactgtt cgctgctgca    2040
ggcgcgactg ttgtggataa ctcttctgct tggcgcaagg acgacgaggt tccactaatc    2100
gtctctgagg tgaacccttc cgacaaggat tccctggtca agggcattat tgcgaaccct    2160
aactgcacca ccatggctgc gatgccagtg ctgaagccac ttcacgatgc cgctggtctt    2220
gtaaagcttc acgtttcctc ttaccaggct gtttccggtt ctggtcttgc aggtgtggaa    2280
accttggcaa gcaggttgc tgcagttgga gaccacaacg ttgagttcgt ccatgatgga    2340
caggctgctg acgcaggcga tgtcggacct tatgtttcac caatcgctta caacgtgctg    2400
ccattcgccg gaaacctcgt cgatgacggc accttcgaaa ccgatgaaga gcagaagctg    2460
cgcaacgaat cccgcaagat tctcggtctc ccagacctca aggtctcagg cacctgcgtc    2520
cgcgtgccgg ttttcaccgg ccacacgctg accattcacg ccgaattcga caaggcaatc    2580
accgtggacc aggcgcagga gatcttgggt gccgcttcag gcgtcaagct tgtcgatgtc    2640 ccaacccccac ttgcagctgc cggcattgac gaatccctcg ttggacgcat ccgtcaggac    2700
tccactgtcg acgataaccg cggtctggtt ctcgtcgtat ctggcgacaa cctccgcaag    2760
ggtgctgcgc taaacaccat ccagatcgct gagctgctgg ttaagtaa                2808
```

```
<210> SEQ ID NO 26
<211> LENGTH: 22
<212> TYPE: DNA
<213> ORGANISM: Corynebacterium glutamicum
<220> FEATURE:
<221> NAME/KEY: misc_feature
<222> LOCATION: (2)..(7)
<223> OTHER INFORMATION: AatII cleavage site
<220> FEATURE:
<221> NAME/KEY: misc_feature
<222> LOCATION: (6)..(11)
<223> OTHER INFORMATION: XbaI cleavage site
<220> FEATURE:
<221> NAME/KEY: RBS
<222> LOCATION: (11)..(16)
<223> OTHER INFORMATION: Ribosome binding site of the gap gene

<400> SEQUENCE: 26
tgacgtctag aggagacaca ac                                              22

<210> SEQ ID NO 27
<211> LENGTH: 4496
<212> TYPE: DNA
<213> ORGANISM: Corynebacterium glutamicum
<220> FEATURE:
<221> NAME/KEY: misc_feature
<222> LOCATION: (1)..(207)
<223> OTHER INFORMATION: Part of the coding region for a
      serine/threonine protein kinase (cg0057)
<220> FEATURE:
<221> NAME/KEY: gene
<222> LOCATION: (322)..(594)
<223> OTHER INFORMATION: Coding region for a putative protein (septation
      inhibitor protein, cg0055)
<220> FEATURE:
<221> NAME/KEY: misc_feature
<222> LOCATION: (812)..(817)
<223> OTHER INFORMATION: Region of the NsiI cleavage site
<220> FEATURE:
<221> NAME/KEY: promoter
```

```
<222> LOCATION: (818)..(1278)
<223> OTHER INFORMATION: Pgap3 promoter according to SEQ ID No. 3
<220> FEATURE:
<221> NAME/KEY: misc_feature
<222> LOCATION: (1279)..(1299)
<223> OTHER INFORMATION: gap RBS according to SEQ ID No. 16
<220> FEATURE:
<221> NAME/KEY: gene
<222> LOCATION: (1300)..(2565)
<223> OTHER INFORMATION: lysC coding region with T311I mutation, atg
      start and tga stop according to SEQ ID No. 24
<220> FEATURE:
<221> NAME/KEY: misc_feature
<222> LOCATION: (2566)..(2584)
<223> OTHER INFORMATION: RBS gap according to SEQ ID No. 26
<220> FEATURE:
<221> NAME/KEY: gene
<222> LOCATION: (2585)..(3619)
<223> OTHER INFORMATION: asd coding region
<220> FEATURE:
<221> NAME/KEY: terminator
<222> LOCATION: (3623)..(3667)
<223> OTHER INFORMATION: gap terminator
<220> FEATURE:
<221> NAME/KEY: misc_feature
<222> LOCATION: (3674)..(3679)
<223> OTHER INFORMATION: Bereich der AvrII-Schnittstelle
<220> FEATURE:
<221> NAME/KEY: misc_feature
<222> LOCATION: (3834)..(4496)
<223> OTHER INFORMATION: Part of the coding region for an iron-chelator
      utilization protein (cg0054)

<400> SEQUENCE: 27
accgaacagg ccatcagtgc cctccgcgct gctggctgga ccgccccaga tcaatccctg      60
atcgtcggcg accccatcca caccgcagcc ctcgtggatc aaaacaaaat cggattccaa     120
tccccaaccc ctgcaacccc cttccgcaaa gacgcccaag tgcaagtgcg actcttcgaa     180
ttcgatctcg ctgcactcgt gcaatagcca acaaggaaac cgtcaaggta gctggcccgg     240
caactgatac gttaagctca acaagataa gtaccagttg ctggggtttt tccaagacaa      300
taaattatga aggtgtgaac aatgccaaag gcaagagtaa ctaaaaacga gaccgcaccg     360
gtttcaagca acccaagcgc aaaccgcacc ccggttaaga tcaattccgc cggaacccca     420
atgtggtaca aggtcatcat gtttgccttc atgatcgtcg gcctagcctg gttgatcatt     480
aactacctcg tgggcccaca gatcccattc atggctgatc ttggtgcatg gaactatggc     540
atcggcttcg gtctgatgat catcggccta ctcatgacca tgggttggcg ttaatccttc     600
aaaaaagtga ctgccgcagc acagcgttga ttcgttgtgc tgcggcagtt gttttgtgcg     660
ggcggatcca gatttagccc ctcatgggca ctctcgtttg gcagttcggg gcactcaaaa     720
aggtaaaacc agactagcgt gcccaagaac tgaacttttt gccagccgtg ggcactcctg     780
ttcggtttga gagccgagaa accagacagg catgcattga agcctaaaaa cgaccgagcc     840
tattgggatt accattgaag ccagtgtgag ttgcatcaca ttggcttcaa atctgagact     900
ttaatttgtg gattcacggg ggtgtaatgt agttcataat taccccattc ggggggagca     960
gatcgtagtg cgaacgattt caggttcgtt ccctgcaaaa actatttagc gcaagtgttg    1020
gaaatgcccc cgtttggggt caatgtccat ttttgaatgt gtctgtatga ttttgcatct    1080
gctgcgaaat ctttgtttcc ccgctaaagt tgaggacagg ttgacacgga gttgactcga    1140
cgaattatcc aatgtgagta ggtttggtgc gtgagttgaa aaaattcgcc atactcgccc    1200
ttgggttctg tcagctcaag aattcttgag tgaccgatgc tctgattgac ctaactgctt    1260
gacacattgc atttcctaca atcggagagg agacacaaca tggccctggt cgtacagaaa    1320
```

```
tatggcggtt cctcgcttga gagtgcggaa cgcattagaa acgtcgctga acggatcgtt    1380
gccaccaaga aggctggaaa tgatgtcgtg gttgtctgct ccgcaatggg agacaccacg    1440
gatgaacttc tggaacttgc agcggcagtg aatcccgttc cgccagctcg tgaaatggat    1500
atgctcctga ctgctggtga gcgtatttct aacgctctcg tcgccatggc tattgagtcc    1560
cttggcgcag aagcccaatc tttcacgggc tctcaggctg gtgtgctcac caccgagcgc    1620 cacgaaacg cacgcattgt tgatgtcact ccaggtcgtg tgcgtgaagc actcgatgag    1680
ggcaagatct gcattgttgc tggttttccag ggtgttaata agaaacccg cgatgtcacc    1740 acgttgggtc gtggtggttc tgacaccact gcagttgcgt tggcagctgc tttgaacgct    1800
gatgtgtgtg agatttactc ggacgttgac ggtgtgtata ccgctgaccc gcgcatcgtt    1860
cctaatgcac agaagctgga aaagctcagc ttcgaagaaa tgctggaact tgctgctgtt    1920
ggctccaaga ttttggtgct gcgcagtgtt gaatacgctc gtgcattcaa tgtgccactt    1980
cgcgtacgct cgtcttatag taatgatccc ggcactttga ttgccggctc tatggaggat    2040
attcctgtgg aagaagcagt ccttaccggt gtcgcaaccg acaagtccga agccaaagta    2100
accgttctgg gtatttccga taagccaggc gaggctgcga aggttttccg tgcgttggct    2160
gatgcagaaa tcaacattga catggttctg cagaacgtct cttctgtaga agacggcacc    2220
accgacatca tcttcacctg ccctcgttcc gacggccgcc gcgcgatgga gatcttgaag    2280
aagcttcagg ttcagggcaa ctggaccaat gtgcttacg acgaccaggt cggcaaagtc    2340
tccctcgtgg gtgctggcat gaagtctcac ccaggtgtta ccgcagagtt catggaagct    2400
ctgcgcgatg tcaacgtgaa catcgaattg atttccacct tgagattcg tatttccgtg    2460 ctgatccgtg aagatgatct ggatgctgct gcacgtgcat tgcatgagca gttccagctg    2520
ggcggcgaag acgaagccgt cgtttatgca ggcaccggac gctgacgtct agaggagaca    2580
caacatgacc accatcgcag ttgttggtgc aaccggccag gtcggccagg ttatgcgcac    2640
ccttttggaa gagcgcaatt cccagctgaa cactgttcgt ttctttgctt ccccacgttc    2700
cgcaggccgt aagattgaat ccgtggcac ggaaatcgag gtagaagaca ttactcaggc    2760
aaccgaggag tccctcaagg acatcgacgt tgcgttgttc tccgctggag caccgcttc    2820 caagcagtac gctccactgt tcgctgctgc aggcgcgact gttgtggata actcttctgc    2880
ttggcgcaag gacgacgagg ttccactaat cgtctctgag gtgaacccct tccgacaagga    2940 ttccctggtc aagggcatta ttgcgaaccc taactgcacc accatggctg cgatgccagt    3000
gctgaagcca cttcacgatg ccgctggtct tgtaaagctt cacgtttcct cttaccaggc    3060
tgtttccggt tctggtcttg caggtgtgga aaccttggca aagcaggttg ctgcagttgg    3120
agaccacaac gttgagttcg tccatgatgg acaggctgct gacgcaggcg atgtcggacc    3180
ttatgtttca ccaatcgctt acaacgtgct gccattcgcc ggaaacctcg tcgatgacgg    3240
caccttcgaa accgatgaag agcagaagct gcgcaacgaa tcccgcaaga ttctcggtct    3300
cccagacctc aaggtctcag gcacctgcgt ccgcgtgccg gttttcaccg ccacacgct    3360 gaccattcac gccgaattcg acaaggcaat caccgtggac caggcgcagg agatcttggg    3420
tgccgcttca ggcgtcaagc ttgtcgatgt cccaaccca cttgcagctg ccggcattga    3480
cgaatccctc gttggacgca tccgtcagga ctccactgtc gacgataacc gcggtctggt    3540
tctcgtcgta tctggcgaca acctccgcaa gggtgctgcg ctaaacacca tccagatcgc    3600
tgagctgctg gttaagtaat attcccaata gcccggggtg tgcctcggcg caccccgggc    3660
tattttgata tcacctagga ctgaagacac gacatttggg cacgccagtc tggttccccc    3720
```

-continued

```
aaaatcagtc cacattcagc tccgaatccc aaaaatcatg ccctcccaga atcgcttcta      3780
agagctcatc agacgccaat caatgcaaac acccattcta aaaactcgac cccttaaatc      3840
tccaatgaga ggtcgtcgaa gttttccagc tgtagcccct cagagagcat cttcatgtag      3900
ttttctttgc ggactgcatc gatctgagtg ttggtggtgt tgtatttcca gtacccaaac      3960
acggccactg catcttttc caatcccacc tgcttgcgga agtgcctgcg gatggatttt      4020
atttcatctc gctcgccggc tgcccacacc acgtaagttt ctgggttttc caggtcatat      4080
gcctgttggg caagtggctg aacagttgga tctgatcccg gcgcgagcag gttcagttcc      4140
agtccgtcga tgctgggtag ttcatcgaag gctgcgggat cgtcagtgac aacccatcct      4200
ttgccacgaa gatctgttgg ccattgatcc aaaatagcgg cgagagcggg gatggcggtg      4260
tcatcaagga agagtgctgc ttgttcgcct tcggggatga caaagtgtgg gcggggtccg      4320
gtgagcacga gggtgtcgtt gattttacg gtgtctgacc agcgcatcat ggggctttcg      4380
tggtggtgtt gaaccacatc caccacgatg ctttcagttg cggcatcaaa ggatcggacg      4440
gtgtagacgc gggtggcgtc gtcgaattct tcgctgaggt aaagcctgat tgccac         4496
```

<210> SEQ ID NO 28
<211> LENGTH: 2531
<212> TYPE: DNA
<213> ORGANISM: Corynebacterium glutamicum
<220> FEATURE:
<221> NAME/KEY: misc_feature
<222> LOCATION: (1)..(1013)
<223> OTHER INFORMATION: Upstream region of the hom coding region
<220> FEATURE:
<221> NAME/KEY: misc_feature
<222> LOCATION: (1012)..(1017)
<223> OTHER INFORMATION: Region of the NsiI cleavage site
<220> FEATURE:
<221> NAME/KEY: promoter
<222> LOCATION: (1018)..(1478)
<223> OTHER INFORMATION: Pgap3 promoter according to SEQ ID No. 3
<220> FEATURE:
<221> NAME/KEY: misc_feature
<222> LOCATION: (1479)..(1500)
<223> OTHER INFORMATION: gap RBS according to SEQ ID No. 17
<220> FEATURE:
<221> NAME/KEY: misc_feature
<222> LOCATION: (1482)..(1487)
<223> OTHER INFORMATION: Region of the NruI cleavage site
<220> FEATURE:
<221> NAME/KEY: gene
<222> LOCATION: (1501)..(2531)
<223> OTHER INFORMATION: hom coding region

<400> SEQUENCE: 28

```
ctgcagtcga ggcttcagag gttttattgc tcgacttcac gtgtgctgac ttcgcgtgct       60
caacttctca tgaggcgaca tcagtcgaaa agccggtcat tgtcgtatga agtctgcgca      120
cgagaagttg agcggaagaa gtcggtgtta agaagtcgac cgcgtgaagt cgcccttag       180 gagaattctg actaactgga gccaaaactt gatccactcg agagctgtgc agtctctttt      240
tccttcaatt ctgcctgctc gagctcgtag aagtagaggt ctacttcagt tggttcacct      300
tgcacacaag catgaagtag tgggtaggtc gagttgttaa atgcggtgta gaagggagt      360 agttcgctag caaaggttaa tttggagtcg ctgtactgcg ggtctcggg tggagtattc      420 ccggaggatt caagaaatct tgacgcatct tgatgaggt atgtttggaa ttcgtcggca      480
ccttcctcgc cggagaggta gtaggagttg tcgtaatttg gaaccagat ggcaaatcgt      540 gcgttttcga ttgcgtccag gagttcctct acgttgtatc tcgcacttgt tgcagcggaa      600
```

```
gcgactcggt tgccgatgtc tccgtatgca gtgagcgtgg cgtttccgag gggaacttga    660
tcagaggaat acaccatgga gccgatgtca gaggcgactg cgggcagatc cttttgaagc    720
tgtttcacaa tttctttgcc cagttcgcgg cggatctgga accacttttg catgcgatcg    780
tcgtcagagt ggttcatgtg aaaaatacac tcaccatctc aatggtcatg gtgaaggcct    840
gtactggctg cgacagcatg gaactcagtg caatggctgt aaggcctgca ccaacaatga    900
ttgagcgaag ctccaaaatg tcctccccgg gttgatatta gatttcataa atatactaaa    960
aatcttgaga gttttccgt tgaaaactaa aaagctggga aggtgaatcg aatgcattga    1020
agcctaaaaa cgaccgagcc tattgggatt accattgaag ccagtgtgag ttgcatcaca   1080
ttggcttcaa atctgagact ttaatttgtg gattcacggg ggtgtaatgt agttcataat   1140 taacccatt cggggagca gatcgtagtg cgaacgattt caggttcgtt ccctgcaaaa     1200
actatttagc gcaagtgttg gaaatgcccc cgtttggggt caatgtccat ttttgaatgt   1260
gtctgtatga ttttgcatct gctgcgaaat ctttgtttcc ccgctaaagt tgaggacagg   1320
ttgacacgga gttgactcga cgaattatcc aatgtgagta ggtttggtgc gtgagttgaa   1380
aaaattcgcc atactcgccc ttgggttctg tcagctcaag aattcttgag tgaccgatgc   1440
tctgattgac ctaactgctt gacacattgc atttcctaca atcgcgagag gagacacaac   1500
atgacctcag catctgcccc aagctttaac cccggcaagg gtcccggctc agcagtcgga   1560
attgcccttt taggattcgg aacagtcggg actgaggtga tgcgtctgat gaccgagtac   1620
ggtgatgaac ttgcgcaccg cattggtggc ccactggagg ttcgtggcat tgctgttttct  1680 gatatctcaa agccacgtga aggcgttgca cctgagctgc tcactgagga cgcttttgca   1740
ctcatcgagc gcgaggatgt tgacatcgtc gttgaggtta tcggcggcat tgagtaccca   1800
cgtgaggtag ttctcgcagc tctgaaggcc ggcaagtctg ttgttaccgc caataaggct   1860
cttgttgcag ctcactctgc tgagcttgct gatgcagcgg aagccgcaaa cgttgacctg   1920
tacttcgagg ctgctgttgc aggcgcaatt ccagtggttg gcccactgcg tcgctccctg   1980
gctggcgatc agatccagtc tgtgatgggc atcgttaacg gcaccaccaa cttcatcttg   2040
gacgccatgg attccaccgg cgctgactat gcagattctt tggctgaggc aactcgtttg   2100
ggttacgccg aagctgatcc aactgcagac gtcgaaggcc atgacgccgc atccaaggct   2160
gcaattttgg catccatcgc tttccacacc cgtgttaccg cggatgatgt gtactgcgaa   2220
ggtatcagca acatcagcgc tgccgacatt gaggcagcac agcaggcagg ccacaccatc   2280
aagttgttgg ccatctgtga aagttcacc aacaaggaag gaaagtcggc tatttctgct   2340
cgcgtgcacc cgactctatt acctgtgtcc cacccactgg cgtcggtaaa caagtccttt   2400
aatgcaatct tgttgaagc agaagcagct ggtcgcctga tgttctacgg aaacggtgca   2460
ggtggcgcgc caaccgcgtc tgctgtgctt ggcgacgtcg ttggtgccgc acgaaacaag   2520
gtgcacggtg g                                                        2531
```

<210> SEQ ID NO 29
<211> LENGTH: 2722
<212> TYPE: DNA
<213> ORGANISM: Corynebacterium glutamicum
<220> FEATURE:
<221> NAME/KEY: misc_feature
<222> LOCATION: (2)..(7)
<223> OTHER INFORMATION: SphI restriction cleavage site
<220> FEATURE:
<221> NAME/KEY: promoter
<222> LOCATION: (10)..(470)
<223> OTHER INFORMATION: Pgap3 promoter according to SEQ ID No. 3

```
<220> FEATURE:
<221> NAME/KEY: gene
<222> LOCATION: (529)..(1695)
<223> OTHER INFORMATION: argJ coding region
<220> FEATURE:
<221> NAME/KEY: gene
<222> LOCATION: (1741)..(2694)
<223> OTHER INFORMATION: argB coding region
<220> FEATURE:
<221> NAME/KEY: gene
<222> LOCATION: (2695)..(2708)
<223> OTHER INFORMATION: Part of the argD coding region
<220> FEATURE:
<221> NAME/KEY: misc_feature
<222> LOCATION: (2716)..(2721)
<223> OTHER INFORMATION: BlnI restriction cleavage site

<400> SEQUENCE: 29
ggcatgcatt gaagcctaaa aacgaccgag cctattggga ttaccattga agccagtgtg      60
agttgcatca cattggcttc aaatctgaga ctttaatttg tggattcacg ggggtgtaat     120
gtagttcata attaaccccca ttcgggggag cagatcgtag tgcgaacgat ttcaggttcg    180
ttccctgcaa aaactatttta gcgcaagtgt tggaaatgcc cccgtttggg gtcaatgtcc    240
atttttgaat gtgtctgtat gattttgcat ctgctgcgaa atctttgttt ccccgctaaa     300
gttgaggaca ggttgacacg gagttgactc gacgaattat ccaatgtgag taggtttggt    360
gcgtgagttg aaaaaattcg ccatactcgc ccttgggttc tgtcagctca agaattcttg     420
agtgaccgat gctctgattg acctaactgc ttgacacatt gcatttccta caatcgactc    480
cctaaccagc aaacacaaca aacacatcta attcagtagg agttccacat ggcagaaaaa     540
ggcattaccg cgccgaaagg cttcgttgct tctgcaacga ccgcgggtat taaagcttct    600
ggcaatcctg acatggcgtt ggtggttaac cagggtccag agttttccgc agcggccgtg     660
tttacacgta accgagtttt cgcagcgcct gtgaaggtga gccgagagaa cgttgctgat    720
ggccagatca gggctgtttt gtacaacgct ggtaatgcta atgcgtgtaa tggtctgcag    780
ggtgagaagg atgctcgtga gtctgtttct catctagctc aaaatttggg cttggaggat    840
tccgatattg gtgtgtgttc cactggtctt attggtgagt tgcttccgat ggataagctc    900
aatgcaggta ttgatcagct gaccgctgag ggcgctttgg gtgacaatgg tgcagctgct    960
gccaaggcga tcatgaccac tgacacggtg gataaggaaa ccgtcgtgtt tgctgatggt   1020
tggactgtcg gcggaatggg caaggcgtg ggcatgatgg cgccgtctct tgccaccatg    1080
ctggtctgct tgaccactga tgcatccgtt actcaggaaa tggctcagat cgcgctggct    1140
aatgctacgg ccgttacgtt tgacccctg gatattgatg gatcaacctc caccaatgac    1200
accgtgttcc tgctggcatc tggcgctagc ggaatcaccc caactcagga tgaactcaac    1260
gatgcggtgt acgcagcttg ttctgatatc gcagcgaagc ttcaggctga tgcagagggt    1320
gtgaccaagc gcgttgctgt gacagtggtg ggaaccacca caacgagca ggcgattaat    1380 gcggctcgca ctgttgctcg tgacaatttg ttcaagtgcg caatgtttgg atctgatcca    1440
aactggggtc gcgtgttggc tgcagtcggc atggctgatg ctgatatgga accagagaag    1500
atttctgtgt tcttcaatgg tcaagcagta tgccttgatt ccactggcgc tcctggtgct    1560
cgtgaggtgg atctttccgg cgctgacatt gatgtccgaa ttgatttggg caccagtggg    1620
gaaggccagg caacagttcg aaccactgac ctgagcttct cctacgtgga gatcaactcc    1680
gcgtacagct cttaaaaaga aacagcactc caactaacaa gcagggaaaa gggcacaggc    1740
atgaatgact tgatcaaaga tttaggctct gaggtgcgcg caaatgtcct cgctgaggcg    1800
```

-continued

```
ttgccatggt tgcagcactt ccgcgacaag attgttgtcg tgaaatatgg cggaaacgcc    1860
atggtggatg atgatctcaa ggctgctttt gctgccgaca tggtcttctt gcgcaccgtg    1920
ggcgcaaaac cagtggtggt gcacggtggt ggacctcaga tttctgagat gctaaaccgt    1980
gtgggtctcc agggcgagtt caaggggtggt ttccgtgtga ccactcctga ggtcatggac    2040
attgtgcgca tggtgctctt tggtcaggtc ggtcgcgatt tagttggttt gatcaactct    2100
catggccctt acgctgtggg aacctccggt gaggatgccg gcctgtttac cgcgcagaag    2160
cgcatggtca acatcgatgg cgtacccact gatattggtt tggtcggaga catcattaat    2220
gtcgatgcct cttccttgat ggatatcatc gaggccggtc gcattcctgt ggtctctacg    2280
attgctccag gcgaagacgg ccagatttac aacattaacg ccgataccgc agcaggtgct    2340
ttggctgcag cgattggtgc agaacgcctg ctggttctca ccaatgtgga aggtctgtac    2400
accgattggc ctgataagag ctcactggtg tccaagatca aggccaccga gctggaggcc    2460
attcttccgg gacttgattc cggcatgatt ccaaagatgg agtcttgctt gaacgcggtg    2520
cgtgggggag taagcgctgc tcatgtcatt gacggccgca tcgcgcactc ggtgttgctg    2580
gagcttttga ccatgggtgg aattggcacg atggtgctgc cggatgtttt tgatcgggag    2640
aattatcctg aaggcaccgt ttttagaaaa gacgacaagg atggggaact gtaaatgagc    2700
acgctggaat attggcctag ga                                             2722
```

<210> SEQ ID NO 30
<211> LENGTH: 2005
<212> TYPE: DNA
<213> ORGANISM: Corynebacterium glutamicum
<220> FEATURE:
<221> NAME/KEY: misc_feature
<222> LOCATION: (379)..(379)
<223> OTHER INFORMATION: Guanine (g) nucleobase
<220> FEATURE:
<221> NAME/KEY: gene
<222> LOCATION: (501)..(1505)
<223> OTHER INFORMATION: gap coding region

<400> SEQUENCE: 30

```
gaagaaattt agatgattga agcctaaaaa cgaccgagcc tattgggatt accattgaag      60
ccagtgtgag ttgcatcaca ttggcttcaa atctgagact ttaatttgtg gattcacggg     120
ggtgtaatgt agttcataat taaccccatt cggggagca gatcgtagtg cgaacgattt      180
caggttcgtt ccctgcaaaa actatttagc gcaagtgttg gaaatgcccc cgtttggggt     240
caatgtccat ttttgaatgt gtctgtatga ttttgcatct gctgcgaaat ctttgtttcc     300
ccgctaaagt tgaggacagg ttgacacgga gttgactcga cgaattatcc aatgtgagta     360
ggtttggtgc gtgagttgga aaaattcgcc atactcgccc ttgggttctg tcagctcaag     420
aattcttgag tgaccgatgc tctgattgac ctaactgctt gacacattgc atttcctaca     480
atctttagag gagacacaac atgaccattc gtgttggtat aacggatttt ggccgtatcg     540
gacgtaactt cttccgcgca gttctggagc gcagcgacga tctcgaggta gttgcagtca     600
acgacctcac cgacaacaag acccttccca ccttctcaa gttcgactcc atcatgggcc     660
gccttggcca ggaagttgaa tacgacgatg actccatcac cgttggtggc aagcgcatcg     720
ctgtttacgc agagcgcgat ccaaagaacc tggactgggc tgcacacaac gttgacatcg     780
tgatcgagtc caccggcttc ttcaccgatg caaacgcggc taaggctcac atcgaagcag     840
gtgccaagaa ggtcatcatc tccgcaccag caagcaacga agacgcaacc ttcgtttacg     900
gtgtgaacca cgagtcctac gatcctgaga accacaacgt gatctccggc gcatcttgca     960
```

```
ccaccaactg cctcgcacca atggcaaagg tcctaaacga caagttcggc atcgagaacg    1020
gcctcatgac caccgttcac gcatacactg gcgaccagcg cctgcacgat gcacctcacc    1080
gcgacctgcg tcgtgcacgt gcagcagcag tcaacatcgt tcctacctcc accggtgcag    1140
ctaaggctgt tgctctggtt ctcccagagc tcaagggcaa gcttgacggc tacgcacttc    1200
gcgttccagt tatcaccggt tccgcaaccg acctgacctt caacaccaag tctgaggtca    1260
ccgttgagtc catcaacgct gcaatcaagg aagctgcagt cggcgagttc ggcgagaccc    1320
tggcttactc cgaagagcca ctggtttcca ccgacatcgt ccacgattcc cacggctcca    1380
tcttcgacgc tggcctgacc aaggtctccg gcaacaccaa gggttgtt cctggtacg       1440 acaacgagtg gggctacacc tgccagctcc tgcgtctgac cgagctcgta gcttccaagc    1500
tctaattagt tcacatcgct aacgtgggcg atcgatgctc acggtgatgt gtcatcccaa    1560
tagcccgggg tgtgcctcgg cgcaccccgg gctattttgt gtctttaatc aatacaattg    1620
aataccggtg ccagcgccac acaatgtgtg gcaatctggg acagtgcatc acattgcacc    1680
agaagaattt tttaaacaat caaatctcca aggagtacgg catggctgtt aagaccctca    1740
aggacttgct cgacgaaggc gtagacggac gccacgtcat cgttcgatct gacttcaatg    1800
ttcccctcaa cgatgaccgc gagatcaccg ataagggccg aatcattgcc tccctaccaa    1860
cccttaaagc actgagcgaa ggtggcgcaa aggtcatcgt catggctcac cttggccgcc    1920
caaagggcga ggtcaacgag aagtactccc tcgcacctgt cgctgaggca ctctccgatg    1980
agcttggcca gtacgttgca cttgc                                          2005

<210> SEQ ID NO 31
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer Pgap3-1

<400> SEQUENCE: 31
cgtttggggt caatgtccat                                                 20

<210> SEQ ID NO 32
<211> LENGTH: 18
<212> TYPE: DNA
<213> ORGANISM: Corynebacterium glutamicum

<400> SEQUENCE: 32
cccagtccag gttctttg                                                   18

<210> SEQ ID NO 33
<211> LENGTH: 2005
<212> TYPE: DNA
<213> ORGANISM: Corynebacterium glutamicum
<220> FEATURE:
<221> NAME/KEY: mutation
<222> LOCATION: (379)..(379)
<223> OTHER INFORMATION: Adenine (a) nucleobase
<220> FEATURE:
<221> NAME/KEY: gene
<222> LOCATION: (501)..(1505)
<223> OTHER INFORMATION: gap coding region

<400> SEQUENCE: 33
gaagaaattt agatgattga agcctaaaaa cgaccgagcc tattgggatt accattgaag    60
```

| | |
|---|---|
| ccagtgtgag ttgcatcaca ttggcttcaa atctgagact ttaatttgtg gattcacggg | 120 |
| ggtgtaatgt agttcataat taaccccatt cggggagca gatcgtagtg cgaacgattt | 180 |
| caggttcgtt ccctgcaaaa actatttagc gcaagtgttg gaaatgcccc cgtttggggt | 240 |
| caatgtccat ttttgaatgt gtctgtatga ttttgcatct gctgcgaaat ctttgtttcc | 300 |
| ccgctaaagt tgaggacagg ttgacacgga gttgactcga cgaattatcc aatgtgagta | 360 |
| ggtttggtgc gtgagttgaa aaaattcgcc atactcgccc ttgggttctg tcagctcaag | 420 |
| aattcttgag tgaccgatgc tctgattgac ctaactgctt gacacattgc atttcctaca | 480 |
| atctttagag gagacacaac atgaccattc gtgttggtat taacggattt ggccgtatcg | 540 |
| gacgtaactt cttccgcgca gttctggagc gcagcgacga tctcgaggta gttgcagtca | 600 |
| acgacctcac cgacaacaag acccttttcca cccttctcaa gttcgactcc atcatgggcc | 660 |
| gccttggcca ggaagttgaa tacgacgatg actccatcac cgttggtggc aagcgcatcg | 720 |
| ctgtttacgc agagcgcgat ccaaagaacc tggactgggc tgcacacaac gttgacatcg | 780 |
| tgatcgagtc caccggcttc ttcaccgatg caaacgcggc taaggctcac atcgaagcag | 840 |
| gtgccaagaa ggtcatcatc tccgcaccag caagcaacga agacgcaacc ttcgtttacg | 900 |
| gtgtgaacca cgagtcctac gatcctgaga accacaacgt gatctccggc gcatcttgca | 960 |
| ccaccaactg cctcgcacca atggcaaagg tcctaaacga caagttcggc atcgagaacg | 1020 |
| gcctcatgac caccgttcac gcatacactg gcgaccagcg cctgcacgat gcacctcacc | 1080 |
| gcgacctgcg tcgtgcacgt gcagcagcag tcaacatcgt tcctacctcc accggtgcag | 1140 |
| ctaaggctgt tgctctggtt ctcccagagc tcaagggcaa gcttgacggc tacgcacttc | 1200 |
| gcgttccagt tatcaccggt tccgcaaccg acctgacctt caacaccaag tctgaggtca | 1260 |
| ccgttgagtc catcaacgct gcaatcaagg aagctgcagt cggcgagttc ggcgagaccc | 1320 |
| tggcttactc cgaagagcca ctggtttcca ccgacatcgt ccacgattcc cacggctcca | 1380 |
| tcttcgacgc tggcctgacc aaggtctccg gcaacaccgt caaggttgtt cctggtacg | 1440 |
| acaacgagtg gggctacacc tgccagctcc tgcgtctgac cgagctcgta gcttccaagc | 1500 |
| tctaattagt tcacatcgct aacgtgggcg atcgatgctc acggtgatgt gtcatcccaa | 1560 |
| tagcccgggg tgtgcctcgg cgcacccgg gctattttgt gtctttaatc aatacaattg | 1620 |
| aataccggtg ccagcgccac acaatgtgtg gcaatctggg acagtgcatc acattgcacc | 1680 |
| agaagaattt tttaaacaat caaatctcca aggagtacgg catggctgtt aagaccctca | 1740 |
| aggacttgct cgacgaaggc gtagacggac gccacgtcat cgttcgatct gacttcaatg | 1800 |
| ttcccctcaa cgatgaccgc gagatcaccg ataagggccg aatcattgcc tccctaccaa | 1860 |
| cccttaaagc actgagcgaa ggtggcgcaa aggtcatcgt catggctcac cttggccgcc | 1920 |
| caaagggcga ggtcaacgag aagtactccc tcgcacctgt cgctgaggca ctctccgatg | 1980 |
| agcttggcca gtacgttgca cttgc | 2005 |

```
<210> SEQ ID NO 34
<211> LENGTH: 461
<212> TYPE: DNA
<213> ORGANISM: Corynebacterium glutamicum
<220> FEATURE:
<221> NAME/KEY: promoter
<222> LOCATION: (1)..(461)
<223> OTHER INFORMATION: Pg3N3 promoter
<220> FEATURE:
<221> NAME/KEY: mutation
<222> LOCATION: (265)..(265)
<223> OTHER INFORMATION: Thymine (t) nucleobase
```

```
<220> FEATURE:
<221> NAME/KEY: mutation
<222> LOCATION: (269)..(269)
<223> OTHER INFORMATION: Cytosine (c) nucleobase
<220> FEATURE:
<221> NAME/KEY: mutation
<222> LOCATION: (290)..(290)
<223> OTHER INFORMATION: Thymine (t) nucleobase
<220> FEATURE:
<221> NAME/KEY: mutation
<222> LOCATION: (292)..(292)
<223> OTHER INFORMATION: Adenine (a) nucleobase
<220> FEATURE:
<221> NAME/KEY: mutation
<222> LOCATION: (362)..(362)
<223> OTHER INFORMATION: Adenine (a) nucleobase

<400> SEQUENCE: 34
tgaagcctaa aaacgaccga gcctattggg attaccattg aagccagtgt gagttgcatc      60
acattggctt caaatctgag actttaattt gtggattcac gggggtgtaa tgtagttcat     120
aattaacccc attcggggga gcagatcgta gtgcgaacga tttcaggttc gttccctgca     180
aaaactattt agcgcaagtg ttggaaatgc cccgtttgg ggtcaatgtc cattttgaa       240 tgtgtctgta tgattttgca tctgttgcca aatctttgtt tccccgctat aattgaggac     300
aggttgacac ggagttgact cgacgaatta tccaatgtga gtaggtttgg tgcgtgagtt     360
gaaaaaattc gccatactcg cccttgggtt ctgtcagctc aagaattctt gagtgaccga     420
tgctctgatt gacctaactg cttgacacat tgcatttcct a                         461

<210> SEQ ID NO 35
<211> LENGTH: 1660
<212> TYPE: DNA
<213> ORGANISM: Corynebacterium glutamicum

<400> SEQUENCE: 35
gccaattgcg tggcaatcag gctttacctc agcgaagaat tcgacgacgc cacccgcgtc      60
tacaccgtcc gatcctttga tgccgcaact gaaagcatcg tggtggatgt ggttcaacac     120
caccacgaaa gccccatgat gcgctggtca gacaccgtaa aaatcaacga caccctcgtg     180
ctcaccggac cccgcccaca ctttgtcatc cccgaaggcg aacaagcagc actcttcctt     240
gatgacaccg ccatcccgc tctcgccgct attttggatc aatggccaac agatcttcgt      300
ggcaaaggat gggttgtcac tgacgatccc gcagccttcg atgaactacc cagcatcgac     360
ggactggaac tgaacctgct cgcgccggga tcagatccaa ctgttcagcc acttgcccaa     420
caggcatatg acctggaaaa cccagaaact tacgtggtgt gggcagccgg cgagcgagat     480
gaaataaaat ccatccgcag gcacttccgc aagcaggtgg gattggaaaa agatgcagtg     540
gccgtgtttg ggtactggaa atacaacacc accaacactc agatcgatgc agtccgcaaa     600
gaaaactaca tgaagatgct ctctgaaggg ctacagctgg aaaacttcga cgacctctca     660
ttggagattt aaggggtcga gtttttagaa tgggtgtttg cattgattgg cgtctgatga     720
gctcttagaa gcgattctgg gagggcatga ttttttggat tcggagctga atgtggactg     780
attttggggg aaccagactg gcgtgcccaa atgtcgtgtc ttcagtccta ggcgatgcat     840
gcctgtctgt tttctcggct ctcaaaccga acaggagtgc ccacggctgg caaaaagttc     900
agttcttggg cacgctagtc tggttttacc tttttgagtg ccccgaactg ccaaacgaga     960
gtgcccatga ggggctaaat ctggatccgc ccgcacaaaa caactgccgc agcacaacga    1020
atcaacgctg tgctgcggca gtcacttttt tgaaggatta acgccaaccc atggtcatga    1080
```

-continued

| | |
|---|---|
| gtaggccgat gatcatcaga ccgaagccga tgccatagtt ccatgcacca agatcagcca | 1140 |
| tgaatgggat ctgtgggccc acgaggtagt taatgatcaa ccaggctagg ccgacgatca | 1200 |
| tgaaggcaaa catgatgacc ttgtaccaca ttggggttcc ggcggaattg atcttaaccg | 1260 |
| gggtgcggtt tgcgcttggg ttgcttgaaa ccggtgcggt ctcgttttta gttactcttg | 1320 |
| cctttggcat tgttcacacc ttcataattt attgtcttgg aaaaacccca gcaactggta | 1380 |
| cttatcttgt ttgagcttaa cgtatcagtt gccgggccag ctaccttgac ggtttccttg | 1440 |
| ttggctattg cacgagtgca gcgagatcga attcgaagag tcgcacttgc acttgggcgt | 1500 |
| ctttgcggaa gagggttgca ggggttgggg attggaatcc gattttgttt tgatccacga | 1560 |
| gggctgcggt gtggatgggg tcgccgacga tcagggattg atctgggggcg gtccagccag | 1620 |
| cagcgcggag ggcactgatg gcctgttcgg tgaagcttgc | 1660 |

```
<210> SEQ ID NO 36
<211> LENGTH: 2872
<212> TYPE: DNA
<213> ORGANISM: Corynebacterium glutamicum
<220> FEATURE:
<221> NAME/KEY: misc_feature
<222> LOCATION: (3)..(8)
<223> OTHER INFORMATION: restriction site NsiI
<220> FEATURE:
<221> NAME/KEY: promoter
<222> LOCATION: (9)..(469)
<223> OTHER INFORMATION: gap promoter according to SEQ ID NO. 2
<220> FEATURE:
<221> NAME/KEY: RBS
<222> LOCATION: (470)..(490)
<223> OTHER INFORMATION: RBS gap according to SEQ ID No. 16
<220> FEATURE:
<221> NAME/KEY: gene
<222> LOCATION: (491)..(1756)
<223> OTHER INFORMATION: coding sequence lysC
<220> FEATURE:
<221> NAME/KEY: RBS
<222> LOCATION: (1754)..(1775)
<223> OTHER INFORMATION: RBS gap according to SEQ ID No. 26
<220> FEATURE:
<221> NAME/KEY: gene
<222> LOCATION: (1776)..(2810)
<223> OTHER INFORMATION: coding sequence asd
<220> FEATURE:
<221> NAME/KEY: terminator
<222> LOCATION: (2814)..(2858)
<223> OTHER INFORMATION: gap terminator
<220> FEATURE:
<221> NAME/KEY: misc_feature
<222> LOCATION: (2865)..(2870)
<223> OTHER INFORMATION: restriction site AvrII

<400> SEQUENCE: 36
```

| | |
|---|---|
| cgatgcattg aagcctaaaa acgaccgagc ctattgggat taccattgaa gccagtgtga | 60 |
| gttgcatcac attggcttca aatctgagac tttaatttgt ggattcacgg gggtgtaatg | 120 |
| tagttcataa ttaaccccat tcgggggagc agatcgtagt gcgaacgatt tcaggttcgt | 180 |
| tccctgcaaa aactatttag cgcaagtgtt ggaaatgccc ccgtttgggg tcaatgtcca | 240 |
| tttttgaatg tgtctgtatg attttgcatc tgctgcgaaa tctttgtttc cccgctaaag | 300 |
| ttgaggacag gttgacacgg agttgactcg acgaattatc caatgtgagt aggtttggtg | 360 |
| cgtgagttgg aaaaattcgc catactcgcc cttgggttct gtcagctcaa gaattcttga | 420 |
| gtgaccgatg ctctgattga cctaactgct tgacacattg catttcctac aatcggagag | 480 |
| gagacacaac atgccctggt cgtacagaa atatggcggt tcctcgcttg agagtgcgga | 540 |
| acgcattaga aacgtcgctg aacggatcgt tgccaccaag aaggctggaa atgatgtcgt | 600 |

```
ggttgtctgc tccgcaatgg gagacaccac ggatgaactt ctggaacttg cagcggcagt    660
gaatcccgtt ccgccagctc gtgaaatgga tatgctcctg actgctggtg agcgtatttc    720
taacgctctc gtcgccatgg ctattgagtc ccttggcgca aagcccaat ctttcacggg     780
ctctcaggct ggtgtgctca ccaccgagcg ccacggaaac gcacgcattg ttgatgtcac    840
tccaggtcgt gtgcgtgaag cactcgatga gggcaagatc tgcattgttg ctggtttcca    900
gggtgttaat aaagaaaccc gcgatgtcac cacgttgggt cgtggtggtt ctgacaccac    960
tgcagttgcg ttggcagctg cttttgaacgc tgatgtgtgt gagatttact cggacgttga   1020
cggtgtgtat accgctgacc cgcgcatcgt tcctaatgca cagaagctgg aaaagctcag   1080
cttcgaagaa atgctggaac ttgctgctgt tggctccaag attttggtgc tgcgcagtgt   1140
tgaatacgct cgtgcattca atgtgccact tcgcgtacgc tcgtcttata gtaatgatcc   1200
cggcactttg attgccggct ctatggagga tattcctgtg aagaagcag tccttaccgg    1260
tgtcgcaacc gacaagtccg aagccaaagt aaccgttctg ggtatttccg ataagccagg   1320
cgaggctgcg aaggttttcc gtgcgttggc tgatgcagaa atcaacattg acatggttct   1380
gcagaacgtc tcttctgtag aagacggcac caccgacatc atcttcacct gccctcgttc   1440
cgacggccgc cgcgcgatgg agatcttgaa gaagcttcag gttcagggca actggaccaa   1500
tgtgctttac gacgaccagg tcggcaaagt ctccctcgtg ggtgctggca tgaagtctca   1560
cccaggtgtt accgcagagt tcatggaagc tctgcgcgat gtcaacgtga acatcgaatt   1620
gatttccacc tctgagattc gtatttccgt gctgatccgt gaagatgatc tggatgctgc   1680
tgcacgtgca ttgcatgagc agttccagct gggcggcgaa gacgaagccg tcgtttatgc   1740
aggcaccgga cgctgacgtc tagaggagac acaacatgac caccatcgca gttgttggtg   1800
caaccggcca ggtcggccag gttatgcgca cccttttgga agagcgcaat ttcccagctg   1860
acactgttcg tttctttgct tccccacgtt ccgcaggccg taagattgaa ttccgtggca   1920
cggaaatcga ggtagaagac attactcagg caaccgagga gtccctcaag gacatcgacg   1980
ttgcgttgtt ctccgctgga ggcaccgctt ccaagcagta cgctccactg ttcgctgctg   2040
caggcgcgac tgttgtggat aactcttctg cttggcgcaa ggacgacgag gttccactaa   2100
tcgtctctga ggtgaaccct tccgacaagg attccctggt caagggcatt attgcgaacc   2160
ctaactgcac caccatggct gcgatgccag tgctgaagcc acttcacgat gccgctggtc   2220
ttgtaaagct tcacgtttcc tcttaccagg ctgtttccgg ttctggtctt gcaggtgtgg   2280
aaaccttggc aaagcaggtt gctgcagttg agaccacaa cgttgagttc gtccatgatg   2340
gacaggctgc tgacgcaggc gatgtcggac cttatgtttc accaatcgct tacaacgtgc   2400
tgccattcgc cggaaacctc gtcgatgacg gcaccttcga aaccgatgaa gagcagaagc   2460
tgcgcaacga atcccgcaag attctcggtc tcccagacct caaggtctca ggcacctgcg   2520
tccgcgtgcc ggtttccacc ggccacacgc tgaccattca cgccgaattc gacaaggcaa   2580
tcaccgtgga ccaggcgcag gagatcttgg gtgccgcttc aggcgtcaag cttgtcgatg   2640
tcccaacccc acttgcagct gccggcattg acgaatccct cgttggacgc atccgtcagg   2700
actccactgt cgacgataac cgcggtctgg ttctcgtcgt atctggcgac aacctccgca   2760
agggtgctgc gctaaacacc atccagatcg ctgagctgct ggttaagtaa tattcccaat   2820
agcccggggt gtgcctcggc gcaccccggg ctattttgat atcacctagg cg           2872
```

<210> SEQ ID NO 37

```
<211> LENGTH: 2872
<212> TYPE: DNA
<213> ORGANISM: Corynebacterium glutamicum
<220> FEATURE:
<221> NAME/KEY: misc_feature
<222> LOCATION: (3)..(8)
<223> OTHER INFORMATION: restriction site NsiI
<220> FEATURE:
<221> NAME/KEY: promoter
<222> LOCATION: (9)..(469)
<223> OTHER INFORMATION: gap promoter according to SEQ ID NO. 3
<220> FEATURE:
<221> NAME/KEY: RBS
<222> LOCATION: (470)..(490)
<223> OTHER INFORMATION: RBS gap according to SEQ ID No. 16
<220> FEATURE:
<221> NAME/KEY: gene
<222> LOCATION: (491)..(1756)
<223> OTHER INFORMATION: coding sequence lysC
<220> FEATURE:
<221> NAME/KEY: RBS
<222> LOCATION: (1754)..(1775)
<223> OTHER INFORMATION: RBS gap according to SEQ ID No. 26
<220> FEATURE:
<221> NAME/KEY: gene
<222> LOCATION: (1776)..(2810)
<223> OTHER INFORMATION: coding sequence asd
<220> FEATURE:
<221> NAME/KEY: terminator
<222> LOCATION: (2814)..(2858)
<223> OTHER INFORMATION: gap terminator
<220> FEATURE:
<221> NAME/KEY: misc_feature
<222> LOCATION: (2865)..(2870)
<223> OTHER INFORMATION: restriction site AvrII

<400> SEQUENCE: 37
```

| | | | | | |
|---|---|---|---|---|---|
| cgatgcattg | aagcctaaaa | acgaccgagc | ctattgggat | taccattgaa | gccagtgtga | 60 |
| gttgcatcac | attggcttca | aatctgagac | tttaatttgt | ggattcacgg | gggtgtaatg | 120 |
| tagttcataa | ttaaccccat | tcggggagc | agatcgtagt | gcgaacgatt | tcaggttcgt | 180 |
| tccctgcaaa | aactatttag | cgcaagtgtt | ggaaatgccc | ccgtttgggg | tcaatgtcca | 240 |
| tttttgaatg | tgtctgtatg | attttgcatc | tgctgcgaaa | tctttgtttc | cccgctaaag | 300 |
| ttgaggacag | gttgacacgg | agttgactcg | acgaattatc | caatgtgagt | aggtttggtg | 360 |
| cgtgagttga | aaaaattcgc | catactcgcc | cttgggttct | gtcagctcaa | gaattcttga | 420 |
| gtgaccgatg | ctctgattga | cctaactgct | tgacacattg | catttcctac | aatcggagag | 480 |
| gagacacaac | atggccctgg | tcgtacagaa | atatggcggt | tcctcgcttg | agagtgcgga | 540 |
| acgcattaga | aacgtcgctg | aacggatcgt | tgccaccaag | aaggctggaa | atgatgtcgt | 600 |
| ggttgtctgc | tccgcaatgg | gagacaccac | ggatgaactt | ctggaacttg | cagcggcagt | 660 |
| gaatcccgtt | ccgccagctc | gtgaaatgga | tatgctcctg | actgctggtg | agcgtatttc | 720 |
| taacgctctc | gtcgccatgg | ctattgagtc | ccttggcgca | gaagcccaat | ctttcacggg | 780 |
| ctctcaggct | ggtgtgctca | ccaccgagcg | ccacggaaac | gcacgcattg | ttgatgtcac | 840 |
| tccaggtcgt | gtgcgtgaag | cactcgatga | gggcaagatc | tgcattgttg | ctggtttcca | 900 |
| gggtgttaat | aaagaaaccc | gcgatgtcac | cacgttgggt | cgtggtggtt | ctgacaccac | 960 |
| tgcagttgcg | ttggcagctg | ctttgaacgc | tgatgtgtgt | gagatttact | cggacgttga | 1020 |
| cggtgtgtat | accgctgacc | cgcgcatcgt | tcctaatgca | cagaagctgg | aaaagctcag | 1080 |
| cttcgaagaa | atgctggaac | ttgctgctgt | tggctccaag | attttggtgc | tgcgcagtgt | 1140 |
| tgaatacgct | cgtgcattca | atgtgccact | tcgcgtacgc | tcgtcttata | gtaatgatcc | 1200 |
| cggcactttg | attgccggct | ctatggagga | tattcctgtg | gaagaagcag | tccttaccgg | 1260 |

```
tgtcgcaacc gacaagtccg aagccaaagt aaccgttctg ggtatttccg ataagccagg    1320
cgaggctgcg aaggttttcc gtgcgttggc tgatgcagaa atcaacattg acatggttct    1380
gcagaacgtc tcttctgtag aagacggcac caccgacatc atcttcacct gccctcgttc    1440
cgacggccgc cgcgcgatgg agatcttgaa gaagcttcag gttcagggca actgaccaa     1500 tgtgctttac gacgaccagg tcggcaaagt ctccctcgtg ggtgctggca tgaagtctca    1560
cccaggtgtt accgcagagt tcatggaagc tctgcgcgat gtcaacgtga acatcgaatt    1620
gatttccacc tctgagattc gtatttccgt gctgatccgt gaagatgatc tggatgctgc    1680
tgcacgtgca ttgcatgagc agttccagct gggcggcgaa gacgaagccg tcgtttatgc    1740
aggcaccgga cgctgacgtc tagaggagac acaacatgac caccatcgca gttgttggtg    1800
caaccggcca ggtcggccag gttatgcgca ccctttggga agagcgcaat tcccagctg    1860 acactgttcg tttctttgct tccccacgtt ccgcaggccg taagattgaa ttccgtggca    1920
cggaaatcga ggtagaagac attactcagg caaccgagga gtccctcaag gacatcgacg    1980
ttgcgttgtt ctccgctgga ggcaccgctt ccaagcagta cgctccactg ttcgctgctg    2040
caggcgcgac tgttgtggat aactcttctg cttggcgcaa ggacgacgag gttccactaa    2100
tcgtctctga ggtgaaccct tccgacaagg attccctggt caagggcatt attgcgaacc    2160
ctaactgcac caccatggct gcgatgccag tgctgaagcc acttcacgat gccgctggtc    2220
ttgtaaagct tcacgtttcc tcttaccagg ctgtttccgg ttctggtctt gcaggtgtgg    2280
aaaccttggc aaagcaggtt gctgcagttg agaccacaa cgttgagttc gtccatgatg     2340
gacaggctgc tgacgcaggc gatgtcggac cttatgtttc accaatcgct acaacgtgc     2400 tgccattcgc cggaaacctc gtcgatgacg gcaccttcga accgatgaa gagcagaagc     2460 tgcgcaacga atcccgcaag attctcggtc tcccagacct caaggtctca ggcacctgcg    2520
tccgcgtgcc ggttttcacc ggccacacgc tgaccattca cgccgaattc gacaaggcaa    2580
tcaccgtgga ccaggcgcag gagatcttgg gtgccgcttc aggcgtcaag cttgtcgatg    2640
tcccaacccc acttgcagct gccggcattg acgaatccct cgttggacgc atccgtcagg    2700
actccactgt cgacgataac cgcggtctgg ttctcgtcgt atctggcgac aacctccgca    2760
agggtgctgc gctaaacacc atccagatcg ctgagctgct ggttaagtaa tattcccaat    2820
agcccggggt gtgcctcggc gcaccccggg ctattttgat atcacctagg cg            2872
```

<210> SEQ ID NO 38
<211> LENGTH: 2872
<212> TYPE: DNA
<213> ORGANISM: Corynebacterium glutamicum
<220> FEATURE:
<221> NAME/KEY: misc_feature
<222> LOCATION: (3)..(8)
<223> OTHER INFORMATION: restriction site NsiI
<220> FEATURE:
<221> NAME/KEY: promoter
<222> LOCATION: (9)..(469)
<223> OTHER INFORMATION: gap promoter according to SEQ ID NO. 34
<220> FEATURE:
<221> NAME/KEY: RBS
<222> LOCATION: (470)..(490)
<223> OTHER INFORMATION: RBS gap according to SEQ ID No. 16
<220> FEATURE:
<221> NAME/KEY: gene
<222> LOCATION: (491)..(1756)
<223> OTHER INFORMATION: coding sequence lysC
<220> FEATURE:
<221> NAME/KEY: RBS
<222> LOCATION: (1754)..(1775)

<223> OTHER INFORMATION: RBS gap according to SEQ ID No. 26
<220> FEATURE:
<221> NAME/KEY: gene
<222> LOCATION: (1776)..(2810)
<223> OTHER INFORMATION: coding sequence asd
<220> FEATURE:
<221> NAME/KEY: terminator
<222> LOCATION: (2814)..(2858)
<223> OTHER INFORMATION: gap terminator
<220> FEATURE:
<221> NAME/KEY: misc_feature
<222> LOCATION: (2865)..(2870)
<223> OTHER INFORMATION: restriction site AvrII

<400> SEQUENCE: 38

```
cgatgcattg aagcctaaaa acgaccgagc ctattgggat taccattgaa gccagtgtga      60
gttgcatcac attggcttca aatctgagac tttaatttgt ggattcacgg gggtgtaatg     120
tagttcataa ttaaccccat tcgggggagc agatcgtagt gcgaacgatt tcaggttcgt     180
tccctgcaaa aactatttag cgcaagtgtt ggaaatgccc ccgtttgggg tcaatgtcca     240
tttttgaatg tgtctgtatg attttgcatc tgttgccaaa tctttgtttc cccgctataa     300
ttgaggacag gttgacacgg agttgactcg acgaattatc caatgtgagt aggtttggtg     360
cgtgagttga aaaaattcgc catactcgcc cttgggttct gtcagctcaa gaattcttga     420
gtgaccgatg ctctgattga cctaactgct tgacacattg catttcctac aatcggagag     480
gagacacaac atgccctgg tcgtacagaa atatggcggt tcctcgcttg agagtgcgga      540
acgcattaga aacgtcgctg aacggatcgt tgccaccaag aaggctggaa atgatgtcgt     600
ggttgtctgc tccgcaatgg gagacaccac ggatgaactt ctggaacttg cagcggcagt     660
gaatcccgtt ccgccagctc gtgaaatgga tatgctcctg actgctggtg agcgtatttc     720
taacgctctc gtcgccatgg ctattgagtc ccttggcgca gaagcccaat ctttcacggg     780
ctctcaggct ggtgtgctca ccaccgagcg ccacggaaac gcacgcattg ttgatgtcac     840
tccaggtcgt gtgcgtgaag cactcgatga gggcaagatc tgcattgttg ctggtttcca     900
gggtgttaat aaagaaaccc gcgatgtcac cacgttgggt cgtggtggtt ctgacaccac     960
tgcagttgcg ttggcagctg cttgaacgc tgatgtgtgt gagatttact cggacgttga    1020
cggtgtgtat accgctgacc cgcgcatcgt tcctaatgca cagaagctgg aaaagctcag    1080
cttcgaagaa atgctggaac ttgctgctgt tggctccaag attttggtgc tgcgcagtgt    1140
tgaatacgct cgtgcattca atgtgccact tcgcgtacgc tcgtcttata gtaatgatcc    1200
cggcactttg attgccggct ctatggagga tattcctgtg gaagaagcag tccttaccgg    1260
tgtcgcaacc gacaagtccg aagccaaagt aaccgttctg ggtatttccg ataagccagg    1320
cgaggctgcg aaggttttcc gtgcgttggc tgatgcagaa atcaacattg acatggttct    1380
gcagaacgtc tcttctgtag aagacggcac caccgacatc atcttcacct gccctcgttc    1440
cgacggccgc cgcgcgatgg agatcttgaa gaagcttcag gttcagggca actgaccaa     1500
tgtgctttac gacgaccagg tcggcaaagt ctccctcgtg ggtgctggca tgaagtctca    1560
cccaggtgtt accgcagagt tcatggaagc tctgcgcgat gtcaacgtga acatcgaatt    1620
gatttccacc tctgagattc gtatttccgt gctgatccgt gaagatgatc tggatgctgc    1680
tgcacgtgca ttgcatgagc agttccagct gggcggcgaa gacgaagccg tcgtttatgc    1740
aggcaccgga cgctgacgtc tagaggagac acaacatgac caccatcgca gttgttggtg    1800
caaccggcca ggtcggccag gttatgcgca cccttttgga agagcgcaat ttcccagctg    1860
acactgttcg tttctttgct tccccacgtt ccgcaggccg taagattgaa ttccgtggca    1920
```

```
cggaaatcga ggtagaagac attactcagg caaccgagga gtccctcaag gacatcgacg   1980
ttgcgttgtt ctccgctgga ggcaccgctt ccaagcagta cgctccactg ttcgctgctg   2040
caggcgcgac tgttgtggat aactcttctg cttggcgcaa ggacgacgag gttccactaa   2100
tcgtctctga ggtgaaccct tccgacaagg attccctggt caagggcatt attgcgaacc   2160
ctaactgcac caccatggct gcgatgccag tgctgaagcc acttcacgat gccgctggtc   2220
ttgtaaagct tcacgtttcc tcttaccagg ctgtttccgg ttctggtctt gcaggtgtgg   2280
aaaccttggc aaagcaggtt gctgcagttg agaccacaa cgttgagttc gtccatgatg   2340
gacaggctgc tgacgcaggc gatgtcggac cttatgtttc accaatcgct acaacgtgc   2400 tgccattcgc cggaaacctc gtcgatgacg gccttcga aaccgatgaa gagcagaagc   2460
tgcgcaacga atcccgcaag attctcggtc tcccagacct caaggtctca ggcacctgcg   2520
tccgcgtgcc ggttttcacc ggccacacgc tgaccattca cgccgaattc gacaaggcaa   2580
tcaccgtgga ccaggcgcag gagatcttgg gtgccgcttc aggcgtcaag cttgtcgatg   2640
tcccaacccc acttgcagct gccggcattg acgaatccct cgttggacgc atccgtcagg   2700
actccactgt cgacgataac cgcggtctgg ttctcgtcgt atctggcgac aacctccgca   2760
agggtgctgc gctaaacacc atccagatcg ctgagctgct ggttaagtaa tattcccaat   2820
agcccggggt gtgcctcggc gcaccccggg ctattttgat atcacctagg cg           2872
```

<210> SEQ ID NO 39
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer cg0054_9.p

<400> SEQUENCE: 39
ccacccatca ccctcacttc                                                20

<210> SEQ ID NO 40
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer cg0054_10.p

<400> SEQUENCE: 40
gcactctcgt ttggcagttc                                                20

<210> SEQ ID NO 41
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer QlysC_WT_P2

<400> SEQUENCE: 41
aagtgccggg atcattacta                                                20

<210> SEQ ID NO 42
<211> LENGTH: 2549
<212> TYPE: DNA

<213> ORGANISM: Corynebacterium glutamicum
<220> FEATURE:
<221> NAME/KEY: misc_feature
<222> LOCATION: (2)..(7)
<223> OTHER INFORMATION: BamHI cleavage site
<220> FEATURE:
<221> NAME/KEY: misc_feature
<222> LOCATION: (2543)..(2548)
<223> OTHER INFORMATION: XbaI cleavage site

<400> SEQUENCE: 42

```
gggatcccgc tgcagtcgag gcttcagagg ttttattgct cgacttcacg tgtgctgact      60
tcgcgtgctc aacttctcat gaggcgacat cagtcgaaaa gccggtcatt gtcgtatgaa     120
gtctgcgcac gagaagttga gcggaagaag tcggtgttaa gaagtcgacc gcgtgaagtc     180
gcccttagg agaattctga ctaactggag ccaaaacttg atccactcga gagctgtgca      240
gtctctttt ccttcaattc tgcctgctcg agctcgtaga agtagaggtc tacttcagtt      300
ggttcacctt gcacacaagc atgaagtagt gggtaggtcg agttgttaaa tgcggtgtag     360
aaggggagta gttcgctagc aaaggttaat ttggagtcgc tgtactgcgg ttctcgggt      420
ggagtattcc cggaggattc aagaaatctt gacgcatctt tgatgaggta tgtttggaat     480
tcgtcggcac cttcctcgcc ggagaggtag taggagttgt cgtaatttgg aacccagatg     540
gcaaatcgtg cgttttcgat tgcgtccagg agttcctcta cgttgtatct cgcacttgtt     600
gcagcggaag cgactcggtt gccgatgtct ccgtatgcag tgagcgtggc gtttccgagg     660
ggaacttgat cagaggaata caccatggag ccgatgtcag aggcgactgc gggcagatcc     720
ttttgaagct gtttcacaat ttctttgccc agttcgcggc ggatctggaa ccacttttgc     780
atgcgatcgt cgtcagagtg gttcatgtga aaaatacact caccatctca atggtcatgg     840
tgaaggcctg tactggctgc gacagcatgg aactcagtgc aatggctgta aggcctgcac     900
caacaatgat tgagcgaagc tccaaaatgt cctccccggg ttgatattag atttcataaa     960
tatactaaaa atcttgagag ttttccgtt gaaaactaaa aagctgggaa ggtgaatcga    1020
atgcattgaa gcctaaaaac gaccgagcct attgggatta ccattgaagc cagtgtgagt    1080
tgcatcacat tggcttcaaa tctgagactt taatttgtgg attcacgggg gtgtaatgta    1140
gttcataatt aaccccattc gggggagcag atcgtagtgc gaacgatttc aggttcgttc    1200
cctgcaaaaa ctatttagcg caagtgttgg aaatgccccc gtttgggtc aatgtccatt     1260
tttgaatgtg tctgtatgat tttgcatctg ctgcgaaatc tttgtttccc cgctaaagtt    1320
gaggacaggt tgacacggag ttgactcgac gaattatcca atgtgagtag gtttggtgcg    1380
tgagttgaaa aaattcgcca tactcgccct tgggttctgt cagctcaaga attcttgagt    1440
gaccgatgct ctgattgacc taactgcttg acacattgca tttcctacaa tcgcgagagg    1500
agacacaaca tgacctcagc atctgcccca agctttaacc ccggcaaggg tcccggctca    1560
gcagtcggaa ttgccctttt aggattcgga acagtcggca ctgaggtgat gcgtctgatg    1620
accgagtacg gtgatgaact tgcgcaccgc attggtggcc cactggaggt tcgtggcatt    1680
gctgtttctg atatctcaaa gccacgtgaa ggcgttgcac ctgagctgct cactgaggac    1740
gcttttgcac tcatcgagcg cgaggatgtt gacatcgtcg ttgaggttat cggcggcatt    1800
gagtacccac gtgaggtagt tctcgcagct ctgaaggccg gcaagtctgt tgttaccgcc    1860
aataaggctc ttgttgcagc tcactctgct gagcttgctg atgcagcgga agccgcaaac    1920
gttgacctgt acttcgaggc tgctgttgca ggcgcaattc cagtggttgg cccactgcgt    1980
cgctccctgg ctggcgatca gatccagtct gtgatgggca tcgttaacgg caccaccaac    2040
```

```
ttcatcttgg acgccatgga ttccaccggc gctgactatg cagattcttt ggctgaggca    2100
actcgtttgg gttacgccga agctgatcca actgcagacg tcgaaggcca tgacgccgca    2160
tccaaggctg caattttggc atccatcgct ttccacaccc gtgttaccgc ggatgatgtg    2220
tactgcgaag gtatcagcaa catcagcgct gccgacattg aggcagcaca gcaggcaggc    2280
cacaccatca agttgttggc catctgtgag aagttcacca acaaggaagg aaagtcggct    2340
atttctgctc gcgtgcaccc gactctatta cctgtgtccc acccactggc gtcggtaaac    2400
aagtccttta atgcaatctt tgttgaagca gaagcagctg tcgcctgat gttctacgga    2460 aacggtgcag gtggcgcgcc aaccgcgtct gctgtgcttg gcgacgtcgt tggtgccgca    2520
cgaaacaagg tgcacggtgg gctctagag                                     2549

<210> SEQ ID NO 43
<211> LENGTH: 2442
<212> TYPE: DNA
<213> ORGANISM: Corynebacterium glutamicum
<220> FEATURE:
<221> NAME/KEY: misc_feature
<222> LOCATION: (2)..(7)
<223> OTHER INFORMATION: BamHI cleavage site
<220> FEATURE:
<221> NAME/KEY: misc_feature
<222> LOCATION: (2436)..(2441)
<223> OTHER INFORMATION: XbaI cleavage site

<400> SEQUENCE: 43
gggatcccgc ctggttgctg atcgtatcgt tcagttcgcc aagcttgttg gccctgagaa      60
cgtcattgcg tccactgact gtggtctggg cggacgtctg cattcccaga tcgcatgggc     120
aaagctggag tccctagtag agggcgctcg cattgcatca aggaactgt tctaagctag     180 acaacgaggg ttgctagtct aagcagcaaa atgagcggct gttgttcctt caggaaaatt     240
atctgaagga acaatagccg ctcatttat gtcagtgtgc ttttaagcgt cgacgttgat     300
gccaaactgg gtgagcatgt cacgcagagt ctgcttgaac gatgggtcga cggtcaccat     360
gaaggatgct gcggtggaag caagagtggt gattgcgagc aatccctgca gtaccgcaaa     420
aggaatggca agccattctg gtggggagac aatggaacca atcactggca tttcggacaa     480
ccgatcgatc agtgcttgct gctcttcgct gatttcatcg tcatcatcgc tggtgtcttt     540
gccggaggag ctcaagcttg gggccgcagg aatgtcgcca ttgctgagca ttgagctgcc     600
ttcagagctg cctggccagg tttcgttcc atcgactgga tttccatcat catcaaggat     660
ctgtgatgag gtgatgttgt ctgagagctg tgtcagtgcg tcagaggact gagcctgggc     720
aactggagtg aacacggaca atgccacagc gcttgctgta acagggtca aagtacttcg     780 acgcaaagac aaaactttc tcctggcaat aaatatgcgg atttactatg gaaacaagat     840
agaagattgg atagcgaaag ctatcctcaa ctcgtggaaa gtgtagtgcc acaaccacag     900
tattggctag aaaacaatct atagcattgt tctacaaaga gctatgcatt gaagcctaaa     960
aacgaccgag cctattggga ttaccattga agccagtgtg agttgcatca cattggcttc    1020
aaatctgaga ctttaatttg tggattcacg ggggtgtaat gtagttcata attaacccca    1080
ttcgggggag cagatcgtag tgcgaacgat ttcaggttcg ttccctgcaa aaactattta    1140
gcgcaagtgt tggaaatgcc cccgtttggg gtcaatgtcc attttgaat gtgtctgtat    1200 gattttgcat ctgctgcgaa atctttgttt ccccgctaaa gttgaggaca ggttgacacg    1260
gagttgactc gacgaattat ccaatgtgag taggtttggt gcgtgagttg aaaaaattcg    1320
```

| | |
|---|---|
| ccatactcgc ccttgggttc tgtcagctca agaattcttg agtgaccgat gctctgattg | 1380 |
| acctaactgc ttgacacatt gcatttccta caatcgcgat ttagaggaga cacaacatga | 1440 |
| gtgaaacata cgtgtctgag aaaagtccag gagtgatggc tagcggagcg gagctgattc | 1500 |
| gtgccgccga cattcaaacg gcgcaggcac gaatttcctc cgtcattgca ccaactccat | 1560 |
| tgcagtattg ccctcgtctt tctgaggaaa ccggagcgga atctacctt aagcgtgagg | 1620 |
| atctgcagga tgttcgttcc tacaagatcc gcggtgcgct gaactctgga gcgcagctca | 1680 |
| cccaagagca gcgcgatgca ggtatcgttg ccgcatctgc aggtaaccat gcccagggcg | 1740 |
| tggcctatgt gtgcaagtcc ttgggcgttc agggacgcat ctatgttcct gtgcagactc | 1800 |
| caaagcaaaa gcgtgaccgc atcatggttc acggcggaga gtttgtctcc ttggtggtca | 1860 |
| ctggcaataa cttcgacgaa gcatcggctg cagcgcatga agatgcagag cgcaccggcg | 1920 |
| caacgctgat cgagcctttc gatgctcgca acaccgtcat cggtcagggc accgtggctg | 1980 |
| ctgagatctt gtcgcagctg acttccatgg gcaagagtgc agatcacgtg atggttccag | 2040 |
| tcggcggtgg cggacttctt gcaggtgtgg tcagctacag gctgatatg gcacctcgca | 2100 |
| ctgcgatcgt tggtatcgaa ccagcgggag cagcatccat gcaggctgca ttgcacaatg | 2160 |
| gtggaccaat cactttggag actgttgatc cctttgtgga cggcgcagca gtcaaacgtg | 2220 |
| tcggagatct caactacacc atcgtggaga agaaccaggg tcgcgtgcac atgatgagcg | 2280 |
| cgaccgaggg cgctgtgtgt actgagatgc tcgatcttta ccaaaacgaa ggcatcatcg | 2340 |
| cggagcctgc tggcgcgctg tctatcgctg ggttgaagga aatgtccttt gcacctggtt | 2400 |
| ctgtcgtggt gtgcatcatc tctggtggca acagctctag ag | 2442 |

<210> SEQ ID NO 44
<211> LENGTH: 2072
<212> TYPE: DNA
<213> ORGANISM: Corynebacterium glutamicum
<220> FEATURE:
<221> NAME/KEY: misc_feature
<222> LOCATION: (2)..(7)
<223> OTHER INFORMATION: HindIII cleavage site
<220> FEATURE:
<221> NAME/KEY: misc_feature
<222> LOCATION: (2066)..(2071)
<223> OTHER INFORMATION: BamHI cleavage site

<400> SEQUENCE: 44

| | |
|---|---|
| caagcttcac catccggcca tatcaaggtt gaccgcgtct cccgcaccaa catccccggt | 60 |
| gtgtacgcag caggtgactg tactgaccta ttcccactgg cgtccgttgc agcgatgcag | 120 |
| ggccgtatcg ccatgtatca cgcactcggt gaaggcgtga gccccatccg tttgaagact | 180 |
| gttgccaccg cagtgtttac ccgcccagag atcgcagcag taggtatcac ccatgcacaa | 240 |
| gttgattccg gcgaagtgtc tgctcgcgtg attgtgcttc ctttggctac taacccacgc | 300 |
| gccaagatgc gttccctgcg ccacggtttt gtgaagctgt tctgccgccg taactctggc | 360 |
| ctgatcatcg gtggtgtcgt ggtggcaccg accgcgtctg agctgatcct accgatcgct | 420 |
| gtggcagtga ccaaccgtct gacagttgct gatctggctg ataccttcgc ggtgtaccca | 480 |
| tcattgtcag gttcgattac tgaagcagca cgtcagctgg tcaacatgat gatctaggc | 540 |
| taatttttct gagtcttaga ttttgagaaa acccaggatt gctttgtgca ctcctgggtt | 600 |
| ttcactttgt taagcagttt tgggaaaag tgcaaagttt gcaaagttta gaaatatttt | 660 |
| aagaggtaag atgtctgcag gtggaagcgt ttaaatgcgt taaacttggc caaatgtggc | 720 |
| aacctttgca aggtgaaaaa ctggggcggg gttagatcct ggggggttta tttcattcac | 780 |

```
tttggcttga agtcgtgcag gatactatgc attgaagcct aaaaacgacc gagcctattg    840
ggattaccat tgaagccagt gtgagttgca tcacattggc ttcaaatctg agactttaat    900
ttgtggattc acgggggtgt aatgtagttc ataattaacc ccattcgggg gagcagatcg    960
tagtgcgaac gatttcaggt tcgttccctg caaaaactat ttagcgcaag tgttggaaat   1020
gcccccgttt ggggtcaatg tccattttg aatgtgtctg tatgattttg catctgctgc    1080
gaaatctttg tttccccgct aaagttgagg acaggttgac acggagttga ctcgacgaat   1140
tatccaatgt gagtaggttt ggtgcgtgag ttgaaaaaat tcgccatact cgcccttggg   1200
ttctgtcagc tcaagaattc ttgagtgacc gatgctctga ttgacctaac tgcttgacac   1260
attgcatttc ctacaatctt tagaggagac acaacatgtc gactcacaca tcttcaacgc   1320
ttccagcatt caaaaagatc ttggtagcaa accgcggcga aatcgcggtc cgtgctttcc   1380
gtgcagcact cgaaaccggt gcagccacgg tagctattta cccccgtgaa gatcggggat   1440
cattccaccg ctcttttgct tctgaagctg tccgcattgg taccgaaggc tcaccagtca   1500
aggcgtacct ggacatcgat gaaattatcg gtgcagctaa aaaagttaaa gcagatgcca   1560
tttacccggg atacggcttc ctgtctgaaa atgcccagct tgcccgcgag tgtgcggaaa   1620
acggcattac ttttattggc ccaacccag aggttcttga tctcaccggt gataagtctc    1680
gcgcggtaac cgccgcgaag aaggctggtc tgccagtttt ggcggaatcc accccgagca   1740
aaaacatcga tgagatcgtt aaaagcgctg aaggccagac ttaccccatc tttgtgaagg   1800
cagttgccgg tggtggcgga cgcggtatgc gttttgttgc ttcacctgat gagcttcgca   1860
aattagcaac agaagcatct cgtgaagctg aagcggcttt cggcgatggc gcggtatatg   1920
tcgaacgtgc tgtgattaac cctcagcata ttgaagtgca gatccttggc gatcacactg   1980
gagaagttgt acacctttat gaacgtgact gctcactgca gcgtcgtcac caaaaagttg   2040
tcgaaattgc gccagcacag catttggatc cc                                2072
```

<210> SEQ ID NO 45
<211> LENGTH: 28
<212> TYPE: DNA
<213> ORGANISM: Corynebacterium glutamicum
<220> FEATURE:
<221> NAME/KEY: misc_feature
<222> LOCATION: (1)..(28)
<223> OTHER INFORMATION: Primer Hom_X1-A1

<400> SEQUENCE: 45
gatctagacg tccaggagtt cctctacg                                       28

<210> SEQ ID NO 46
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer LC-hom2

<400> SEQUENCE: 46
tggcgtccaa gatgaagttg                                                20

<210> SEQ ID NO 47
<211> LENGTH: 33
<212> TYPE: DNA
<213> ORGANISM: Corynebacterium glutamicum
<220> FEATURE:

```
<221> NAME/KEY: misc_feature
<222> LOCATION: (1)..(33)
<223> OTHER INFORMATION: Primer Pgap3_1.p

<400> SEQUENCE: 47
cgagtactat gcattgaagc ctaaaaacga ccg                                    33

<210> SEQ ID NO 48
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer ilvA-int-rev2

<400> SEQUENCE: 48
accgcggatc ttgtaggaac                                                   20

<210> SEQ ID NO 49
<211> LENGTH: 18
<212> TYPE: DNA
<213> ORGANISM: Corynebacterium glutamicum
<220> FEATURE:
<221> NAME/KEY: misc_feature
<222> LOCATION: (1)..(18)
<223> OTHER INFORMATION: Primer pycUP_3.p

<400> SEQUENCE: 49
agcacgtcag ctggttca                                                     18

<210> SEQ ID NO 50
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer 2xpyc-1

<400> SEQUENCE: 50
aggtacgcct tgactggtga                                                   20
```

US 8,912,313 B2

VARIANTS OF THE PROMOTER OF THE GAP GENE CODING FOR GLYCERALDEHYDE-3-PHOSPHATE DEHYDROGENASE

CROSS-REFERENCE TO RELATED APPLICATIONS

This application claims the benefit DE1020111180119.6 filed Jun. 28, 2011 and U.S. provisional application Ser. No. 61/502,675 filed Jun. 29, 2011, each of which are incorporated herein by reference in their entirety.

FIELD OF THE INVENTION

The present invention relates to a process for preparing fine chemicals with the use of genetically modified microorganisms in which variants of the promoter of the gap gene coding for glyceraldehyde-3-phosphate dehydrogenase enable various genes to be overexpressed.

DESCRIPTION OF THE RELATED ART

Fine chemicals, meaning in particular amino acids, organic acids, vitamins, nucleosides and nucleotides, are employed in human medicine, in the pharmaceutical, cosmetic and food industries and in animal nutrition.

Many of these compounds are prepared by fermenting strains of coryneform bacteria, in particular *Corynebacterium glutamicum*. Due to the great importance, continuous efforts are made to improve the production processes. Said processes may be improved with respect to fermentation-related measures such as, for example, stirring and oxygen supply, or the composition of nutrient media, such as, for example, sugar concentration during fermentation, or the work-up into the product form, for example by means of ion exchange chromatography, or the intrinsic performance characteristics of the microorganism itself.

The performance characteristics of these microorganisms are improved by employing methods of mutagenesis, selection and choice of mutants. In this way strains are obtained which are resistant to anti-metabolites such as, for example, the lysine analogue S-(2-aminoethyl)-cysteine or the valine analogue 2-thiazolalanine, and produce chemical compounds, for example L-amino acids such as L-lysine or L-valine.

For some years now, methods of recombinant DNA technology have likewise been used in order to improve L-amino acid-producing *Corynebacterium glutamicum* strains by enhancing or attenuating individual amino acid biosynthesis genes, for example, and studying the effect on production of said chemical compound.

Summaries regarding the biology, genetics and biotechnology of *Corynebacterium glutamicum* can be found in "Handbook of *Corynebacterium glutamicum*" (Eds.: L. Eggeling and M. Bott, CRC Press, Taylor & Francis, 2005), in the Journal of Biotechnology special issue (Chief Editor: A. Pühler) entitled "A New Era in *Corynebacterium glutamicum* Biotechnology" (Journal of Biotechnology 104/1-3, (2003)), and in the book by T. Scheper (Managing Editor) "Microbial Production of L-Amino Acids" (Advances in Biochemical Engineering/Biotechnology 79, Springer Verlag, Berlin, Germany, 2003).

The nucleotide sequence of the *Corynebacterium glutamicum* genome is described in Ikeda and Nakagawa (Applied Microbiology and Biotechnology 62, 99-109 (2003)), in EP 1 108 790 and in Kalinowski et al. (Journal of Biotechnology 104/1-3, (2003)).

The nucleotide sequences of the *Corynebacterium glutamicum* genome are also available in the database of the National Center for Biotechnology Information (NCBI) of the National Library of Medicine (Bethesda, Md., USA), in the DNA Data Bank of Japan (DDBJ, Mishima, Japan), or in the nucleotide sequence database of the European Molecular Biologies Laboratories (EMBL, Heidelberg, Germany, and Cambridge, UK).

The natural promoter of the *Corynebacterium glutamicum* gap gene coding for glyceraldehyde-3-phosphate dehydrogenase has been described and analysed by Patek et al (Journal of Biotechnology 104, 311-323 (2003)).

In US 2008/0050786, SEQ ID NO:20 depicts a 484 bp DNA molecule referred to as seqP-RBS_20 which comprises the promoter of the gap gene including the ribosome binding site. This promoter may be utilized advantageously for expressing various genes such as the lysC gene coding for aspartate kinase, for example. For better clarity, the sequence is listed under SEQ ID NO:1.

SUMMARY OF THE INVENTION

It was an object of the invention to provide variants of the promoter and/or the expression unit of the gap gene coding for glyceraldehyde-3-phosphate dehydrogenase, it being possible for various genes such as, for example, the lysC gene coding for aspartate kinase to be expressed advantageously under the control of said variants.

DETAILED DESCRIPTION OF THE PREFERRED EMBODIMENTS

Figure 1:
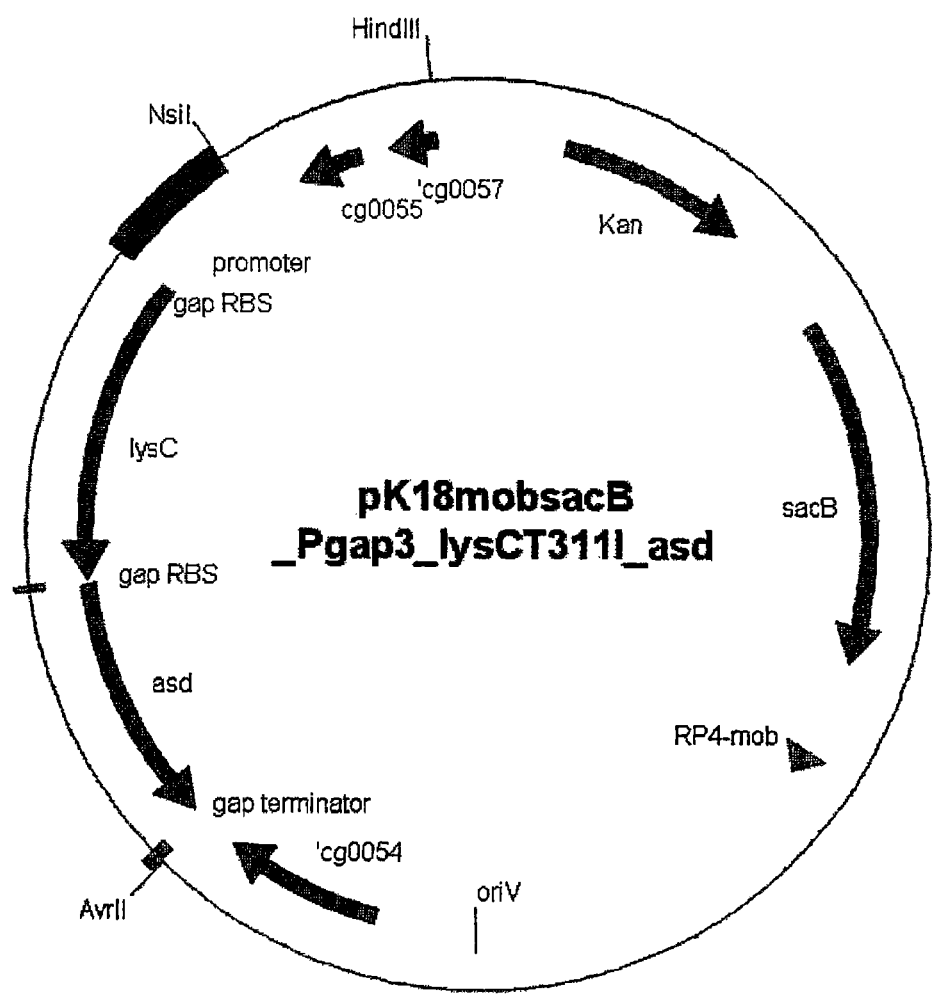
FIG. 1: Plasmid pK18mobsacB_Pgap3_lysCT311I_asd
Figure 2:
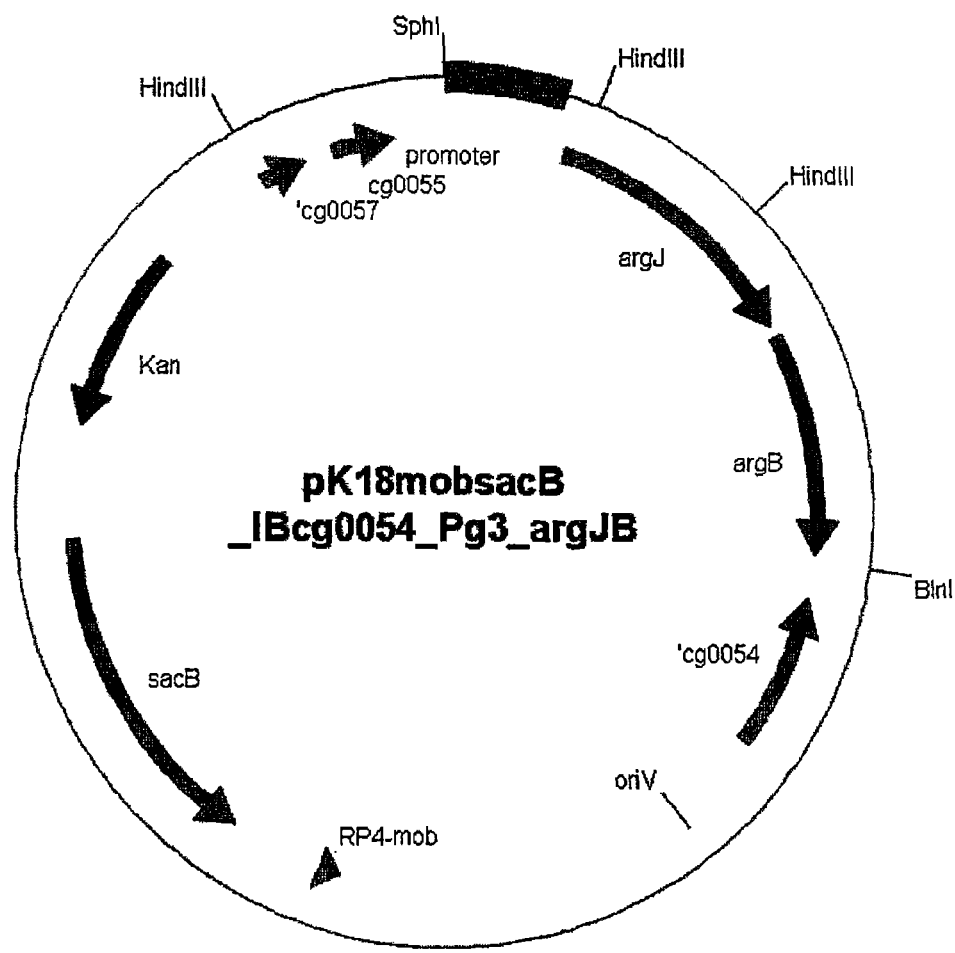
FIG. 2: Plasmid pK18mobsacB_IBcg0054_Pg3_argJB
Figure 3:
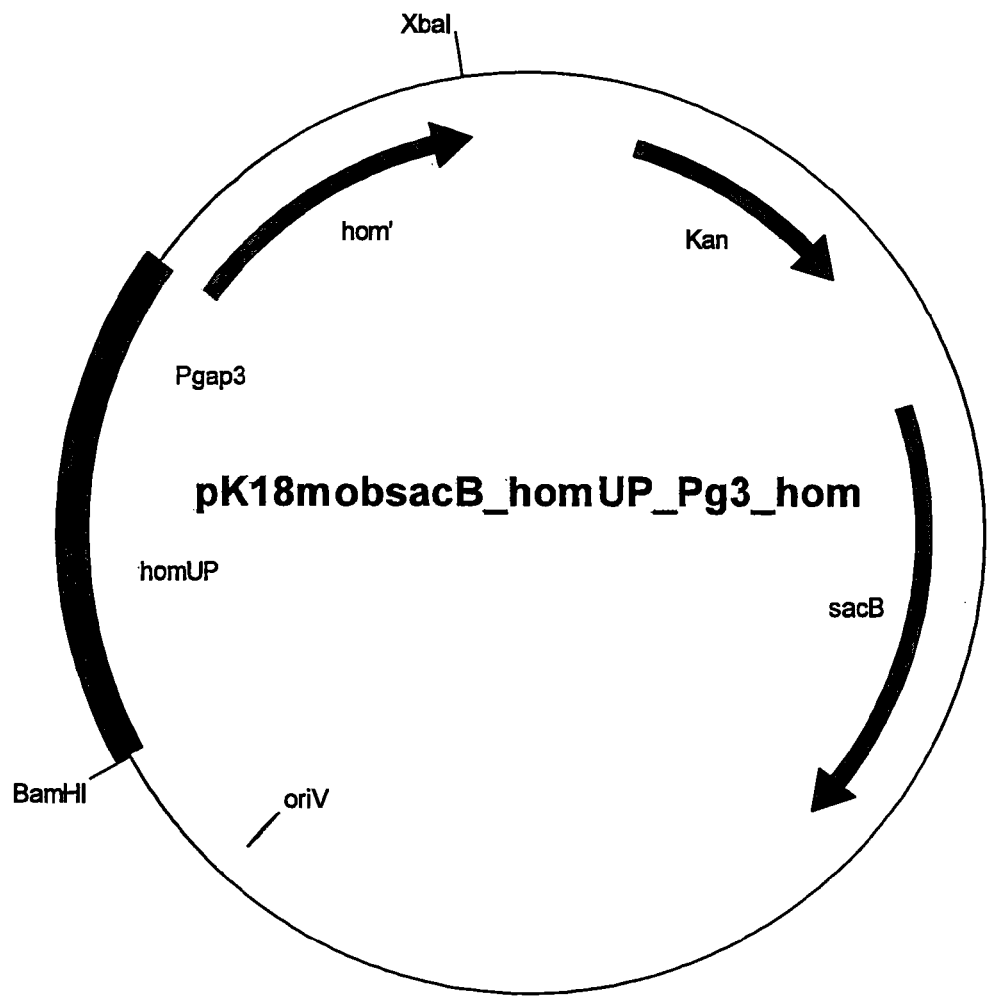
FIG. 3: Map of the plasmid pK18mobsacB_homUP_Pg3_hom
Figure 4:
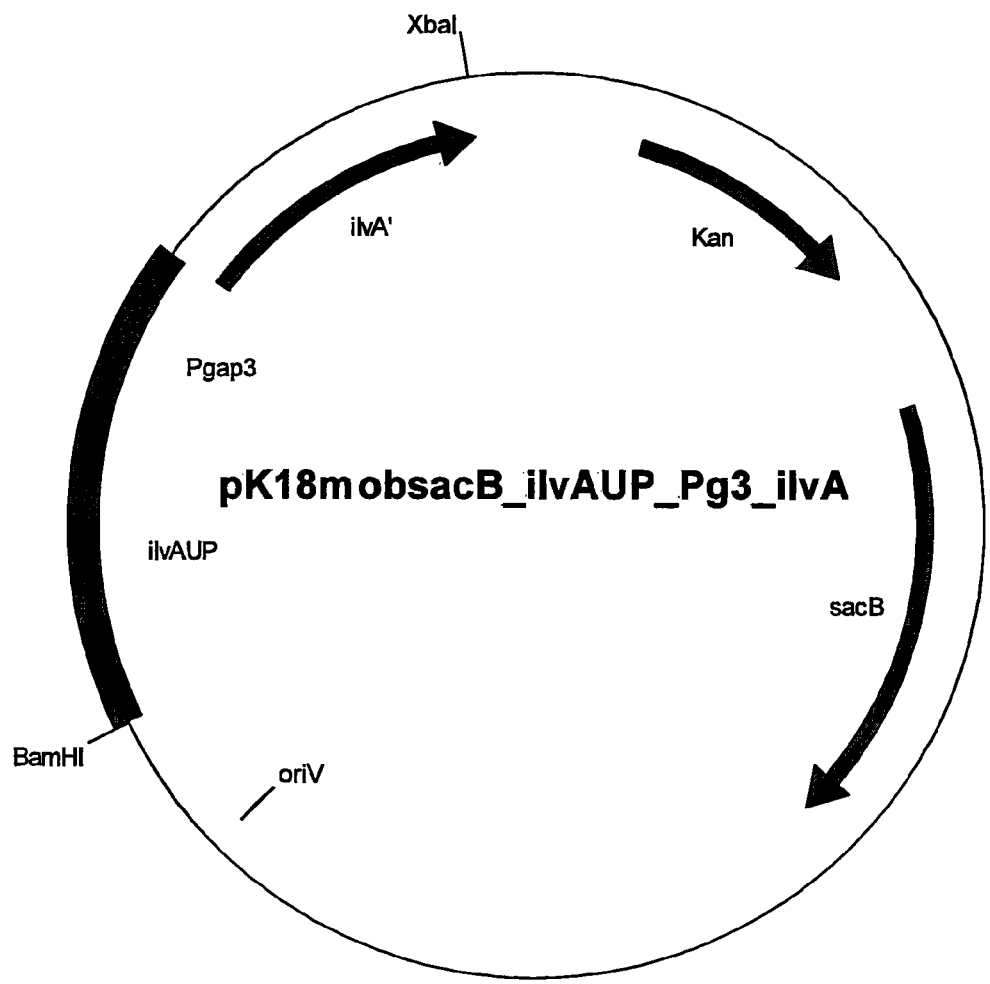
FIG. 4: Map of the plasmid pK18mobsacB_ilvAUP_Pg3_ilvA
Figure 5:
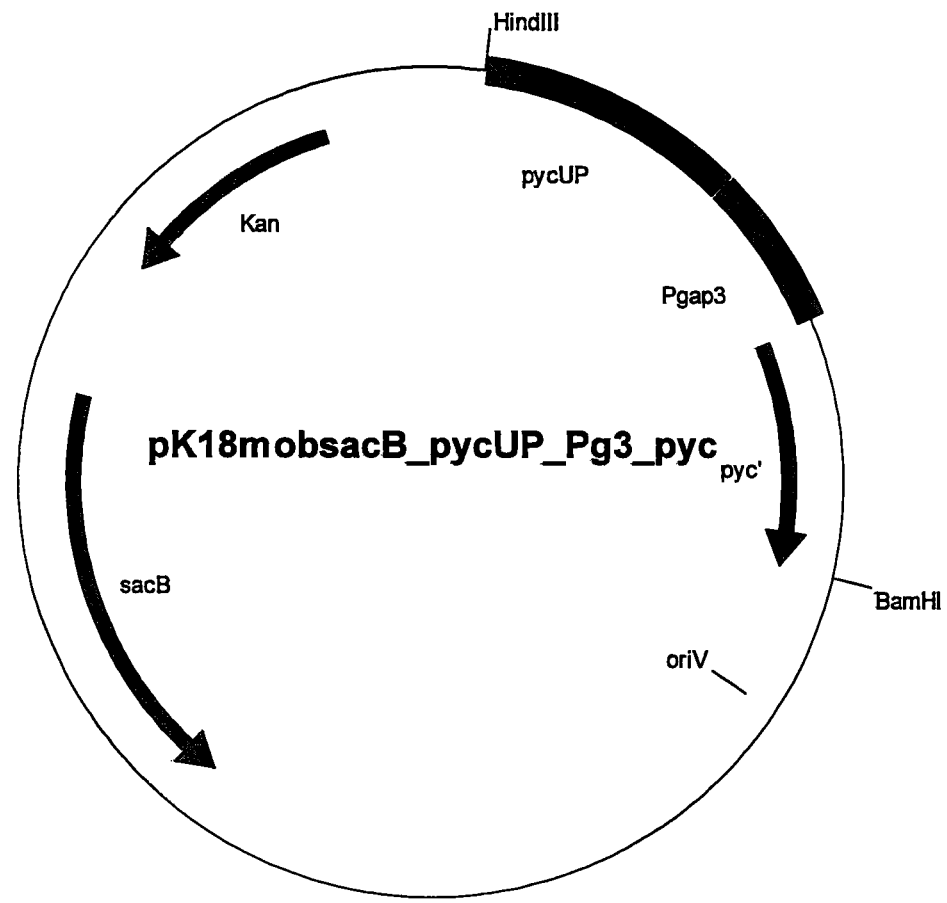
FIG. 5: Map of the plasmid pK18mobsacBpycUP_Pg3_pyc

During the work on the present invention, the activity of the promoter of the *Corynebacterium glutamicum* ATCC13032 gap gene, depicted in SEQ ID NO:2, was found to have increased after replacement of the nucleobase guanine in position 362 of said promoter with the nucleobase adenine.

A further increase in promoter activity was found after additional replacement of the nucleobases:
Cytosine in position 265 with thymine,
Guanin in position 269 with cytosine,
Adenine in position 290 with thymine, and
Guanine in position 292 with adenine,
in the promoter of the *Corynebacterium glutamicum* ATCC13032 gap gene, depicted in SEQ ID NO:2.

The invention therefore relates to an isolated polynucleotide having promoter activity, which comprises a polynucleotide having the nucleotide sequence depicted in SEQ ID NO:3 or SEQ ID NO:34.

The invention also relates to an isolated polynucleotide having promoter activity, which essentially consists of a polynucleotide having the nucleotide sequence depicted in SEQ ID NO:3 or SEQ ID NO:34. The term "essentially" in this context means that a polynucleotide of no more than (≤)1000, no more than (≤)800, no more than (≤)700, no more than (≤)600, no more than (≤)500 or no more than (≤)400 nucleotides in length and a polynucleotide of no more than (≤)15000, no more than (≤)10000, no more than (≤)7500, no more than (≤)5000, no more than (≤)2500, no more than (≤)1000, no more than (≤)800, no more than (≤)700, no more than (≤)600, no more than (≤)500 or no more than 400 nucleotides in length have been added to the 5' end and 3' end, respectively, of the polynucleotides of SEQ ID NO:3 or SEQ ID NO:34.

Any useful combination of the features from the two lists is in accordance with the invention here.

"Useful combination" means, for example, a combination of features which results in an efficient recombination being carried out. The use of additions of the same length flanking a DNA region to be replaced facilitates the transfer of the region by homologous recombination in the experimental procedure. Relatively long flanking homologous regions are advantageous for efficient recombination between circular DNA molecules but cloning of the replacement vector is made more difficult with increasing length of the flanks (Wang et al., Molecular Biotechnology 32:43-53 (2006)). Therefore preference is given to the specific combination of additions of in each case 600 to no more than (≤)1000 nucleotides, with additions of in each case 750 to 850 nucleotides being particularly preferred.

The invention furthermore relates to an isolated polynucleotide having promoter activity, which consists of the nucleotide sequence depicted in SEQ ID NO:3 or SEQ ID NO:34.

Details regarding the biochemistry and chemical structure of polynucleotides as present in living things such as microorganisms, for example, can be found inter alia in the text book "Biochemie" [Biochemistry] by Berg et al (Spektrum Akademischer Verlag Heidelberg•Berlin, Germany, 2003; ISBN 3-8274-1303-6).

Polynucleotides consisting of deoxyribonucleotide monomers containing the nucleobases or bases adenine (A), guanine (G), cytosine (C) and thymine (T) are referred to as deoxyribo-polynucleotides or deoxyribonucleic acid (DNA). Polynucleotides consisting of ribonucleotide monomers containing the nucleobases or bases adenine (A), guanine (G), cytosine (C) and uracil (U) are referred to as ribo-polynucleotides or ribonucleic acid (RNA). The monomers in said polynucleotides are covalently linked to one another by a 3',5'-phosphodiester bond.

A "polynucleotide having promoter activity" or a "promoter" means a polynucleotide, preferably deoxyribo-polynucleotide, or a nucleic acid, preferably deoxyribonucleic acid (DNA), which is functionally linked to a polynucleotide to be transcribed and determines the point and frequency of initiation of transcription of said polynucleotide, thereby enabling the strength of expression of the controlled polynucleotide to be influenced.

Owing to the double-stranded structure of DNA, the strand complementary to the strand in SEQ ID NO:3 or SEQ ID NO:34 of the sequence listing is likewise a subject of the invention.

"Transcription" means the process by which a complementary RNA molecule is produced starting from a DNA template. This process involves proteins such as RNA polymerase, "sigma factors" and transcriptional regulatory proteins. The synthesized RNA (messenger RNA, m-RNA) then serves as template in the process of translation which subsequently yields the polypeptide or protein.

From a chemical point of view, a gene is a polynucleotide. A polynucleotide encoding a protein/polypeptide is used herein synonymously with the term "gene". Accordingly, the two terms "gene" and "coding region" are used synonymously as are the two terms "protein" and "polypeptide".

"Functionally linked" means in this context the sequential arrangement of the polynucleotide having promoter activity according to the invention with a further oligo- or polynucleotide, resulting in transcription of said further polynucleotide.

If the further polynucleotide is a polynucleotide, referred to as second polynucleotide hereinbelow, which codes for a polypeptide/protein and consists of the coding region for a polypeptide, starting with a start codon, including the stop codon and, where appropriate, including a transcription termination sequence, "functionally linked" then means the sequential arrangement of the polynucleotide having promoter activity according to the invention with the second polynucleotide, resulting in transcription of said second polynucleotide and translation of the synthesized RNA.

The second polynucleotide codes for one or more polypeptide(s). A polynucleotide coding for a protein/polypeptide essentially consists of a start codon selected from the group consisting of ATG, GTG and TTG, preferably ATG or GTG, particularly preferably ATG, a protein-encoding sequence and one or more stop codon(s) selected from the group consisting of TAA, TAG and TGA.

If the second polynucleotide codes for a plurality of proteins/polypeptides, each gene may be preceded by a ribosome-binding site. Where appropriate, a termination sequence is located downstream of the last gene.

The second polynucleotide preferably codes for one or more polypeptides or proteins of the biosynthetic pathway of fine chemicals, preferably selected from the group of proteinogenic amino acids, non-proteinogenic amino acids, vitamins, nucleosides, nucleotides and organic acids. Particular preference is given to proteinogenic amino acids, non-proteinogenic amino acids, and organic acids.

The second polynucleotide preferably consists of one or more of the polynucleotides listed in Table 1 of EP 1 108 790 A2 which is hereby incorporated by reference.

The second polynucleotide preferably consists of one or more of the genes or polynucleotides coding for enzymes of the pentosephosphate pathway, selected from the group consisting of:
a) Polynucleotide (zwf gene) coding for the Zwf subunit of glucose-6-phosphate 1-dehydrogenase (Zwf, EC NO.: 1.1.1.49),
b) Polynucleotide (opcA gene) coding for the OpcA subunit of glucose-6-phosphate 1-dehydrogenase (OpcA, EC NO.: 1.1.1.49),
c) Polynucleotide (devB gene) coding for a 6-phosphogluconolactonase (DevB, EC NO.: 3.1.1.31),
d) Polynucleotide (tkt gene) coding for a transketolase (Tkt, EC NO.: 2.2.1.1),
e) Polynucleotide (tal gene) coding for a transaldolase (Tal, EC NO.: 2.2.1.2),
f) Polynucleotide (gnd gene) coding for a 6-phosphogluconate dehydrogenase (Gnd, EC NO.: 1.1.1.44),
g) Polynucleotide (rpe gene) coding for a ribulose-phosphate 3-epimerase (Rpe, EC NO.: 5.1.3.1), and
h) Polynucleotide (rpi gene) coding for a ribose-5-phosphate isomerase B (Rpi, EC NO.: 5.3.1.6),
with particular preference being given to the genes zwf and opcA.

The second nucleotide further preferably consists of one or more of the genes or polynucleotides coding for enzymes of anaplerosis and gluconeogenesis, selected from the group consisting of:
i) Polynucleotide (ppc gene) coding for a phosphoenolpyruvate carboxylase (Ppc, EC NO.: 4.1.1.31), j) Polynucleotide (fbp gene) coding for a fructose 1,6-bisphosphatase (Fbp, EC NO.: 3.1.3.11), and
k) Polynucleotide (pyc gene) coding for a pyruvate carboxylase (Pyc, EC NO.: 6.4.1.1),
with particular preference being given to the pyc gene.

In connection with the preparation of L-lysine, the second polynucleotide preferably consists of one or more of the genes or polynucleotides coding for enzymes of L-lysine biosynthesis, selected from the group consisting of:
l) Polynucleotide (dapA gene) coding for a dihydrodipicolinate synthase (DapA, EC No.: 4.2.1.52),
m) Polynucleotide (asd gene) coding for an aspartate-semialdehyde dehydrogenase (Asd, EC No.: 1.2.1.11),
n) Polynucleotide (ddh gene) coding for a meso-diaminopimelate dehydrogenase (Ddh, EC No.: 1.4.1.16),
o) Polynucleotide (lysA gene) coding for a diaminopimelate decarboxylase (LysA, EC No.: 4.1.1.20),
p) Polynucleotide (aat gene) coding for an aspartate aminotransferase (Aat, EC No.: 2.6.1.1),
q) Polynucleotide (lysE gene) coding for a polypeptide having L-lysine-export activity (LysE, lysine efflux permease),
r) Polynucleotide (dapB gene) coding for a dihydrodipicolinate reductase (DapB, EC No.: 1.3.1.26),
s) Polynucleotide (lysC gene) coding for an aspartate kinase (LysC, EC NO.: 2.7.2.4),
t) Polynucleotide (dapC gene) coding for a succinyldiaminopimelate aminotransferase, AT class I (DapC, EC No.: 2.6.1.17),
u) Polynucleotide (dapD gene) coding for a tetrahydrodipicolinate succinylase (DapD, EC NO.: 2.3.1.117),
v) Polynucleotide (dapE gene) coding for a succinyl-diaminopimelate desuccinylase (DapE, EC NO.: 3.5.1.18), and
w) Polynucleotide (dapF gene) coding for a diaminopimelate epimerase (DapF, EC NO.: 5.1.1.7),
with particular preference being given to the genes dapA, asd, ddh, lysA, lysE, dapB and lysC and very particular preference being given to the genes asd and lysC, since a particular additional enhancement of L-lysine production is achieved using the two latter genes in particular.

In connection with the preparation of L-valine, L-isoleucine, α-ketoisovaleric acid, α-keto-β-methylvaleric acid or α-ketoisocaproic acid, the second polynucleotide preferably consists of one or more of the genes or polynucleotides coding for enzymes of the biosynthesis of L-valine, L-isoleucine, α-ketoisovaleric acid, α-keto-β-methylvaleric acid or α-ketoisocaproic acid, selected from the group consisting of:
x) Polynucleotides (ilvB gene and ilvN gene) coding for the subunits of an acetolactate synthase (IlvBN, EC No.: 4.1.3.18),
y) Polynucleotide (ilvC gene) coding for an isomeroreductase (IlvC, EC No.: 1.1.1.86),
z) Polynucleotide (ilvD gene) coding for a dihydroxy-acid dehydratase (IlvD, EC No.: 4.2.1.9),
aa) Polynucleotide (ilvE gene) coding for a transaminase (IlvE, EC No.: 2.6.1.42),
bb) Polynucleotide (ilvA gene) coding for a threonine dehydratase (IlvA, EC No.: 4.3.1.19),
cc) Polynucleotide (hom gene) coding for a homoserine dehydrogenase (Hom, EC-No.: 1.2.1.11),
dd) Polynucleotide (thrB gene) coding for a homoserine kinase (ThrB, EC-No.: 2.7.1.39),
ee) Polynucleotide (thrC gene) coding for a threonine synthase (ThrC, EC-No.: 4.2.3.1),
ff) Polynucleotide (leuA gene) coding for an isopropylmalate synthase (LeuA, EC-No.: 2.3.3.13),
gg) Polynucleotide (leuB gene) coding for an isopropylmalate dehydrogenase (LeuB, EC-No.: 1.1.1.85),
hh) Polynucleotide (leuC gene) coding for the large subunit of an isopropylmalate isomerase (LeuC, EC-No.: 4.2.1.33),
ii) Polynucleotide (leuD gene) coding for the small subunit of an isopropylmalate isomerase (LeuD, EC-No.: 4.2.1.33),
with particular preference being given to the genes ilvBN, hom, ilvA, ilvC, ilvD and ilvE for isoleucine and valine, with particular preference being given to the genes ilvBN, ilvC and ilvD for α-ketovaleric acid (KIV) and α-keto-β-methylvaleric acid (KMV), and particular preference being given to the genes ilvBN, ilvC, ilvD, leuA, leuB, leuC and leuD for α-ketoisocaproic acid (KIC).

In connection with the preparation of L-ornithine, the second polynucleotide preferably consists of one or more of the genes or polynucleotides coding for enzymes of L-ornithine biosynthesis, selected from the group consisting of:
jj) Polynucleotide (lysE gene) coding for a lysine/ornithine transporter (DE application number 102010003419.3),
kk) Polynucleotide (argB gene) coding for an N-acetylglutamate kinase (ArgB, EC-NO.: 2.7.2.8),
ll) Polynucleotide (gdh gene) coding for a glutamate dehydrogenase (Gdh, EC-No.: 1.4.1.3),
mm) Polynucleotide (argJ gene) coding for a glutamate N-acetyltransferase (ArgJ, EC-No.: 2.3.1.35 and EC-No.: 2.3.1.1),
nn) Polynucleotide (argC gene) coding for an N-acetyl-gamma-glutamyl-phosphate reductase (ArgC, EC-No.: 1.2.1.38), and
oo) Polynucleotide (argD gene) coding for an acetylornithine aminotransferase (ArgD, EC-No.: 2.6.1.11),
with particular preference being given to the genes lysE and argB.

The promoter according to the invention can thus be used in each case for (over)expressing the second polynucleotide in *Corynebacterium glutamicum*.

The second polynucleotide is positioned downstream of the promoter according to the invention, i.e. at the 3' end, such that both polynucleotides are functionally linked to one another either directly or by means of a linker oligonucleotide or linker polynucleotide. Preference is given to both polynucleotides being functionally linked to one another by means of a linker oligonucleotide or linker polynucleotide.

Said linker oligonucleotide or linker polynucleotide consists of deoxyribonucleotides.

In this context, the expression "functionally linked to one another directly" means that the nucleotide via the adenosine nucleotide in position 461 at the 3' end of SEQ ID NO:3 or SEQ ID NO:34 is linked directly to the first nucleotide of the start codon of a coding region. This results in "leaderless" mRNAs which start immediately with the 5'-terminal AUG start codon and therefore do not have any other translation initiation signals.

In this context, the expression "functionally linked to one another by means of a linker oligonucleotide" means that the nucleotide via the adenosine nucleotide in position 461 at the 3' end of SEQ ID NO:3 or SEQ ID NO:34 is linked by an oligonucleotide of 1, 2, 3, 4 or 5 nucleotides in length to the first nucleotide of the start codon of a coding region.

In this context, the expression "functionally linked to one another by means of a linker polynucleotide" means that the nucleotide via the adenosine nucleotide in position 461 at the 3' end of SEQ ID NO:3 or SEQ ID NO:34 is linked by a polynucleotide of from 6 to no more than (≤)00 nucleotides in length to the first nucleotide of the start codon of a coding region.

In this context, the expression "functionally linked to one another" means that the second polynucleotide is bound to the polynucleotide having promoter activity according to the invention in such a way that transcription of the second polynucleotide and translation of the synthesized RNA are ensured.

Depending on the technical requirement, the linker polynucleotide is
6-600, 6-500, 6-400, 6-300, 6-200, 6-180, 6-160, 6-140, 6-120, 6-100, 6-80, 6-60, 6-50, 6-40, 6-30, 6-28, 6-27, 6-26, 6-25 or
8-600, 8-500, 8-400, 8-300, 8-200, 8-180, 8-160, 8-140, 8-120, 8-100, 8-80, 8-60, 8-50, 8-40, 8-30, 8-28, 8-27, 8-26, 8-25 or
10-600, 10-500, 10-400, 10-300, 10-200, 10-180, 10-160, 10-140, 10-120, 10-100, 10-80, 10-60, 10-50, 10-40, 10-30, 10-28, 10-27, 10-26, 10-25 or
12-600, 12-500, 12-400, 12-300, 12-200, 12-180, 12-160, 12-140, 12-120, 12-100, 12-80, 12-60, 12-50, 12-40, 12-30, 12-28, 12-27, 12-26, 12-25 or
14-600, 14-500, 14-400, 14-300, 14-200, 14-180, 14-160, 14-140, 14-120, 14-100, 14-80, 14-60, 14-50, 14-40, 14-30, 14-28, 14-27, 14-26, 14-25 or
16-600, 16-500, 16-400, 16-300, 16-200, 16-180, 16-160, 16-140, 16-120, 16-100, 16-80, 16-60, 16-50, 16-40, 16-30, 16-28, 16-27, 16-26, 16-25 or
18-600, 18-500, 18-400, 18-300, 18-200, 18-180, 18-160, 18-140, 18-120, 18-100, 18-80, 18-60, 18-50, 18-40, 18-30, 18-28, 18-27, 18-26, 18-25 or
20-600, 20-500, 20-400, 20-300, 20-200, 20-180, 20-160, 20-140, 20-120, 20-100, 20-80, 20-60, 20-50, 20-40, 20-30, 20-28, 20-27, 20-26, 20-25 nucleotides in length.

In particularly preferred embodiments, the linker polynucleotide is 20, 21, 22, 23, 24 or 25 nucleotides in length because this produces preferably functional constructs, as can be seen also in examples 3 to 5.

The linker polynucleotide is preferably a polynucleotide which comprises a nucleotide sequence which ensures translation of the synthesized RNA. Such a sequence is referred to in the art also as ribosome-binding site (RBS) or else Shine Dalgarno sequence.

The invention further relates accordingly to an isolated polynucleotide, essentially consisting of a polynucleotide of SEQ ID NO:3 or SEQ ID NO:34, which, via the adenosine nucleotide in position 461 at its 3' end, is functionally linked, directly or by means of a linker polynucleotide which ensures translation of RNA, to a second polynucleotide which contains at its 5' end an ATG or GTG start codon and codes for one or more polypeptide(s). Preference is given to both polynucleotides being functionally linked to one another by means of a linker polynucleotide.

The invention furthermore also relates to an isolated polynucleotide, essentially consisting of a polynucleotide of SEQ ID NO:3 or SEQ ID NO:34, which, via the adenosine nucleotide in position 461 at its 3' end, is functionally linked to a linker oligonucleotide.

In addition, the invention furthermore relates to an isolated polynucleotide, essentially consisting of a polynucleotide of SEQ ID NO:3 or SEQ ID NO:34, which, via the adenosine nucleotide in position 461 at its 3' end, is functionally linked to a linker polynucleotide which ensures translation of RNA.

In this context, the term "essentially" means that a polynucleotide of no more than (≤)1000, no more than (≤)800, no more than (≤)700, no more than (≤)600, no more than (≤)500 or no more than (≤)400 nucleotides in length has been added to the 5' end of the polynucleotide of SEQ ID NO:3 or SEQ ID NO:34 and a polynucleotide of no more than (≤)1000, no more than (≤)800, no more than (≤)700, no more than (≤)600, no more than (≤)500 or no more than (≤)400 nucleotides in length has been added to the 3' end of the second polynucleotide, or a polynucleotide of no more than (≤)15000, no more than (≤)10000, no more than (≤)7500, no more than (≤)5000, no more than (≤)2500, no more than (≤)1000, no more than (≤)800, no more than (≤)700, no more than (≤)600, no more than (≤)500 or no more than (≤)400 nucleotides in length has been added to the 3' end of the linker oligo- or polynucleotide.

Any useful combination of the features from the two lists is in accordance with the invention here.

"Useful combination" means, for example, a combination of features which results in an efficient recombination being carried out. The use of additions of the same length flanking a DNA region to be replaced facilitates the transfer of the region by homologous recombination in the experimental procedure. Relatively long flanking homologous regions are advantageous for efficient recombination between circular DNA molecules but cloning of the replacement vector is made more difficult with increasing length of the flanks (Wang et al., Molecular Biotechnology 32:43-53 (2006)).

Therefore preference is given to the specific combination of additions of in each case 600 to no more than (≤)1000 nucleotides, with additions of in each case 750 to 850 nucleotides being particularly preferred.

In addition, the flank at the 3' end of the linker oligo- or polynucleotide increases in length to no more than (≤)15000 nucleotides when the 3' end is functionally linked to a second polynucleotide which contains at its 5' end an ATG or GTG start codon and codes for one or more polypeptide(s).

The ribosome-binding sites of the genus *Corynebacterium*, preferably of the species *Corynebacterium glutamicum*, are well-described. Von Amador et al. (Microbiology, 145, 915-924 (1999)) have determined the Anti-Shine Dalgarno sequence of the 16S rRNA of *Corynebacterium glutamicum*, which is depicted in SEQ ID NO:4. The sequence reported by Martin et al. (Journal of Biotechnology 104, 41-53 (2003)) is depicted in SEQ ID NO:5.

Other examples of suitable ribosome-binding sites are inter alia
the ribosome-binding site of the ppc gene of *C. glutamicum* ATCC13032 (O'Regan et al., Gene 77, 237-251 (1989)), depicted in SEQ ID NO:6;
the ribosome-binding site of the aceA gene of *C. glutamicum* ATCC13032 (Reinscheid et al., Journal of Bacteriology 176 (12), 3474-3483 (1994)), depicted in SEQ ID NO:7;
the ribosome-binding site of the thiX gene of *C. glutamicum* ATCC13032 (Reinscheid et al., Journal of Bacteriology 176 (12), 3474-3483 (1994)), depicted in SEQ ID NO:8;
the ribosome-binding site of the sod gene of *C. glutamicum* ATCC13032 (WO2005/059144), depicted in SEQ ID NO:9;
the ribosome-binding site of the tuf gene of *C. glutamicum* ATCC13032 (WO2005/059093), depicted in SEQ ID NO:10;
the ribosome-binding site of SEQ ID NO:44 of EP 1918378, depicted in SEQ ID NO:11;
the ribosome-binding site of the fbp gene of *C. glutamicum* ATCC13032, depicted in SEQ ID NO:12;
the ribosome-binding site of the gap gene of *C. glutamicum* ATCC13032 (Eikmanns, Journal of Bacteriology 174 (19), 6076-6086 (1992)), depicted in SEQ ID NO:13.

Preferably the linker polynucleotide contains the ribosome-binding site of the gap gene, depicted in SEQ ID NO:13, or of the fbp gene, depicted in SEQ ID NO:12.

Particularly preferred embodiments of the linker polynucleotide which contain the ribosome-binding site of the gap gene are depicted in SEQ ID NO:14, SEQ ID NO:15, SEQ ID NO:16 and SEQ ID NO:17.

A particularly preferred embodiment of the linker polynucleotide, which contains the ribosome-binding site of the fbp gene, is depicted in SEQ ID NO:18.

These particularly preferred embodiments of the linker polynucleotide ensure translation of RNA in an advantageous manner.

To facilitate chemical linking between the polynucleotide according to the invention having the nucleotide sequence of SEQ ID NO:3 or SEQ ID NO:34, the linker polynucleotide which ensures translation of RNA, and the second polynucleotide coding for one or more polypeptide(s), which has an ATG or GTG start codon at its 5' end, functional nucleotide sequences required for cloning may be incorporated into said polynucleotides at their 5' and 3' ends and are at least partially retained even after said cloning.

The term "functional nucleotide sequence required for cloning" here represents any REII (type II restriction endonuclease) cleavage site present, whose sequence normally consists of from 4 to 8 nucleotides.

In addition, it should be mentioned here that site-specific mutagenesis by means of mutagenesis primers or a de novo gene synthesis (e.g. by GENEART AG (Regensburg, Germany)) of the nucleotide sequences to remove cleavage sites for restriction endonucleases may introduce silent mutations into the sequence in order to enable said cleavage sites to be used advantageously for subsequent cloning steps.

The polynucleotide resulting from the promoter according to the invention being functionally linked to the linker polynucleotide which ensures translation of RNA is also referred to as expression unit hereinbelow.

The invention furthermore relates to the use of the promoter according to the invention or of the expression unit according to the invention for expressing desired genes or polynucleotides in microorganisms. The promoter according to the invention or the expression unit according to the invention ensures transcription and translation of the synthesized RNA, preferably mRNA, into a polypeptide.

Expression is preferably carried out in microorganisms of the genus *Corynebacterium*. Preference is given to strains within the genus *Corynebacterium* which are based on the following species: *Corynebacterium efficiens*, with the deposited type strain being DSM44549, *Corynebacterium glutamicum*, with the deposited type strain being ATCC13032, and *Corynebacterium ammoniagenes*, with the deposited type strain being ATCC6871. Very particular preference is given to the species *Corynebacterium glutamicum*.

In this way it is possible to express polynucleotides that code for polypeptides having a property, preferably enzyme activity, which are not present or detectable in the corresponding host. Thus, for example, Yukawa et al. describe expression of *Escherichia coli* genes for utilizing D-xylose in *Corynebacterium glutamicum* R under the control of the constitutive Ptrc promoter (Applied Microbiology and Biotechnology 81, 691-699 (2008)).

The promoter according to the invention or the expression unit according to the invention is furthermore used for overexpressing desired genes or polynucleotides in microorganisms (overexpression).

Overexpression generally means an increase in the intracellular concentration or activity of a ribonucleic acid, a protein (polypeptide) or an enzyme in comparison with the starting strain (parent strain) or wild-type strain, if the latter is the starting strain. A starting strain (parent strain) means the strain that has been subjected to the measure resulting in overexpression.

For overexpression, preference is given to the methods of recombinant overexpression. These include all methods in which a microorganism is produced using a DNA molecule provided in vitro. Such DNA molecules comprise, for example, promoters, expression cassettes, genes, alleles, coding regions, etc. They are introduced into the desired microorganisms by methods of transformation, conjugation, transduction or similar methods.

In the case of the present invention, the promoters are preferably a polynucleotide of SEQ ID NO:3 or SEQ ID NO:34 and the expression cassettes are preferably a polynucleotide of SEQ ID NO:3 or SEQ ID NO:34 which, via the adenosine nucleotide in position 461 at its 3' end, is functionally linked to a linker polynucleotide which ensures translation of RNA.

The measures of overexpression using the promoter according to the invention or the expression unit according to the invention increase the activity or concentration of the corresponding polypeptide usually by at least 10%, 25%, 50%, 75%, 100%, 150%, 200%, 300%, 400% or 500%, preferably by no more than 1000%, 2000%, 4000%, 10000% or 20000%, based on the activity or concentration of said polypeptide in the strain prior to the measure resulting in overexpression.

The extent of expression or overexpression may be established by measuring the amount of mRNA transcribed from the gene, by determining the amount of polypeptide and by determining enzyme activity.

The amount of mRNA may be determined inter alia by using the methods of "Northern Blotting" and of quantitative RT-PCR. Quantitative RT-PCR involves reverse transcription which precedes the polymerase chain reaction. For this, the LightCycler™ System from Roche Diagnostics (Boehringer Mannheim GmbH, Roche Molecular Biochemicals, Mannheim, Germany) may be used, as described in Jungwirth et al. (FEMS Microbiology Letters 281, 190-197 (2008)), for example. The concentration of the protein may be determined via 1- and 2-dimensional protein gel fractionation and subsequent optical identification of the protein concentration using appropriate evaluation software in the gel. A customary method of preparing protein gels for coryneform bacteria and of identifying said proteins is the procedure described by Hermann et al. (Electrophoresis, 22:1712-23 (2001)). The protein concentration may likewise be determined by Western-Blot hybridization using an antibody specific for the protein to be detected (Sambrook et al., Molecular cloning: a laboratory manual. $2^{nd}$ Ed. Cold Spring Harbor Laboratory Press, Cold Spring Harbor, N.Y., 1989) and subsequent optical evaluation using appropriate software for concentration determination (Lohaus and Meyer (1998) Biospektrum 5:32-39; Lottspeich, Angewandte Chemie 321: 2630-2647 (1999)). The statistical significance of the data collected is determined by means of a T test (Gosset, Biometrika 6(1): 1-25 (1908)).

The measure of overexpressing desired genes using the promoter according to the invention may be combined in a suitable manner with further overexpression measures.

Overexpression is achieved by a multiplicity of methods available in the prior art. These include increasing the copy number in addition to modifying the nucleotide sequences which direct or control expression of the gene.

The copy number may be increased by means of plasmids which replicate in the cytoplasm of the microorganism. To this end, an abundance of plasmids are described in the prior art for very different groups of microorganisms, which plasmids can be used for setting the desired increase in the copy number of the gene. Plasmids suitable for the genus *Corynebacterium* are described, for example, in Tauch et al. (Journal of Biotechnology 104 (1-3), 27-40, (2003)), or in Stansen et al. (Applied and Environmental Microbiology 71, 5920-5928 (2005)).

The copy number may furthermore be increased by at least one (1) copy by introducing further copies into the chromosome of the microorganism. Methods suitable for the genus *Corynebacterium* are described, for example, in the patents WO 03/014330, WO 03/040373 and WO 04/069996.

Gene expression may furthermore be increased by positioning a plurality of promoters upstream of the desired gene or functionally linking them to the gene to be expressed and achieving increased expression in this way. Examples of this are described in the patent WO 2006/069711.

Transcription of a gene is controlled, where appropriate, by proteins which suppress (repressor proteins) or promote (activator proteins) transcription. Accordingly, overexpression can likewise be achieved by increasing the expression of activator proteins or reducing or switching off the expression of repressor proteins or else eliminating the binding sites of the repressor proteins.

The rate of elongation is influenced by the codon usage, it being possible to enhance translation by utilizing codons for t(transfer)RNAs which are frequent in the starting strain. Moreover, replacing a start codon with the ATG codon most frequent in many microorganisms (77% in *Escherichia coli*) may considerably improve translation, since, at the RNA level, the AUG codon is two to three times more effective than the codons GUG and UUG, for example (Khudyakov et al., FEBS Letters 232(2):369-71 (1988); Reddy et al., Proceedings of the National Academy of Sciences of the USA 82(17): 5656-60 (1985)). It is also possible to optimize the sequences surrounding the start codon because synergistic effects between the start codon and the flanking regions have been described (Stenstrom et al., Gene 273(2):259-65 (2001); Hui et al., EMBO Journal 3(3):623-9 (1984)).

Instructions for handling DNA, digestion and ligation of DNA, transformation and selection of transformants can be found inter alia in the known manual by Sambrook et al. "Molecular Cloning: A Laboratory Manual, Second Edition (Cold Spring Harbor Laboratory Press, 1989).

The invention also relates to vectors comprising the polynucleotide according to the invention.

Kirchner and Tauch (Journal of Biotechnology 104:287-299 (2003)) describe a selection of vectors to be used in *Corynebacterium glutamicum*.

Homologous recombination using the vectors according to the invention allows DNA segments on the chromosome to be replaced with polynucleotides according to the invention which are transported into the cell by the vector. For efficient recombination between the circular DNA molecule of the vector and the target DNA on the chromosome, the DNA region to be replaced with the polynucleotide according to the invention is provided at the ends with nucleotide sequences homologous to the target site which determine the site of integration of the vector and of replacement of the DNA.

Thus the polynucleotide having promoter activity according to the invention may
1. be replaced with the native promoter at the native gene locus of the second polynucleotide in the chromosome, or
2. be integrated with the second polynucleotide at the native gene locus of the latter or at another gene locus.

"Replacement of the native promoter at the native gene locus of the second polynucleotide" means the fact that the naturally occurring promoter of the gene which usually is naturally present by way of a single copy at its gene locus in the corresponding wild type or corresponding starting organism in the form of its nucleotide sequence is replaced.

"Another gene locus" means a gene locus whose nucleotide sequence is different from the sequence of the second polynucleotide. Said other gene locus or the nucleotide sequence at said other gene locus is preferably located within the chromosome and normally is not essential for growth and for production of the desired chemical compounds. It is furthermore possible to use intergenic regions within the chromosome, i.e. nucleotide sequences without coding function.

Expression or overexpression is preferably carried out in microorganisms of the genus *Corynebacterium*. Within the genus *Corynebacterium*, preference is given to strains based on the following species: *Corynebacterium efficiens*, with the deposited type strain being DSM44549, *Corynebacterium glutamicum*, with the deposited type strain being ATCC13032, and *Corynebacterium ammoniagenes*, with the deposited type strain being ATCC6871. Very particular preference is given to the species *Corynebacterium glutamicum*.

Some representatives of the species *Corynebacterium glutamicum* are also known in the prior art under different names. These include, for example: strain ATCC13870 referred to as *Corynebacterium acetoacidophilum*, strain DSM20137 referred to as *Corynebacterium lilium*, strain ATCC17965 referred to as *Corynebacterium melassecola*, strain ATCC14067 referred to as *Brevibacterium flavum*, strain ATCC13869 referred to as *Brevibacterium lactofermentum*, and strain ATCC14020 referred to as *Brevibacterium divaricatum*.

The term "*Micrococcus glutamicus*" has also been in use for *Corynebacterium glutamicum*. Some representatives of the species *Corynebacterium efficiens* have also been referred to as *Corynebacterium thermoaminogenes* in the prior art, such as the strain FERM BP-1539, for example.

The microorganisms or strains (starting strains) employed for the expression or overexpression measures according to the invention preferably already possess the ability to secrete a desired fine chemical into the surrounding nutrient medium and accumulate there. The expression "to produce" is also used for this hereinbelow. More specifically, the strains employed for the overexpression measures possess the ability to accumulate the desired fine chemical in concentrations of ≥(at least) ≥0.10 g/l, 0.25 g/l, ≥0.5 g/l, ≥1.0 g/l, ≥1.5 g/l, ≥2.0 g/l, ≥4 g/l or ≥10 g/l in ≤(no more than) 120 hours, ≤96 hours, ≤48 hours, ≤36 hours, ≤24 hours or ≤12 hours in the cell or in the nutrient medium. The starting strains are preferably strains prepared by mutagenesis and selection, by recombinant DNA technologies or by a combination of both methods.

A person skilled in the art understands that a microorganism suitable for the measures of the invention may also be obtained by firstly employing the promoter according to the invention of SEQ ID NO:3 or SEQ ID NO:34 for overexpression of the desired genes in a wild strain such as, for example, the *Corynebacterium glutamicum* type strain ATCC 13032 or the strain ATCC 14067, and then, by means of further genetic measures described in the prior art, causing the microorganism to produce the desired fine chemical(s).

The term "fine chemicals" means with regard to the measures of the invention amino acids, organic acids, vitamins, nucleosides and nucleotides. Particular preference is given to proteinogenic amino acids, non-proteinogenic amino acids, and organic acids.

"Proteinogenic amino acids" mean the amino acids which occur in natural proteins, i.e. in proteins of microorganisms, plants, animals and humans. They serve as structural units for proteins in which they are linked to one another via peptide bonds.

The terms protein and polypeptide are interchangeable.

The mentioning of proteinogenic L-amino acids hereinbelow refers to one or more of the amino acids, including their salts, selected from the group consisting of L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline, and, where appropriate, L-selenocystein and L-pyrrolysine. Particular preference is given to the L-amino acids L-lysine, L-tryptophan, L-methionine, L-valine, L-isoleucine and L-proline. Very particular preference is given to L-lysine and L-valine.

The mentioning of L-lysine or lysine hereinbelow refers to not only the bases but also the salts such as, for example, lysine monohydrochloride or lysine sulphate.

The non-proteinogenic amino acids include inter alia L-ornithine and L-homoserine.

The organic acids include inter alia α-keto acids, with particular preference being given to α-ketoisocaproic acid (KIC), α-ketovaleric acid (KIV) and α-keto-β-methylvaleric acid (KMV).

Examples of L-lysine-secreting or -producing strains of the species Corynebacterium glutamicum are:
  Corynebacterium glutamicum MH20-22B (=DSM16835) described in Menkel et al. (Applied and Environmental Microbiology 55(3), 684-688 (1989)) and deposited as DSM16835,
  Corynebacterium glutamicum DM1729 described in Georgi et al. (Metabolic Engineering 7, 291-301 (2005)) and in EP 1 717 616 A2 and deposited as DSM17576,
  Corynebacterium glutamicum DSM13994 described in U.S. Pat. No. 6,783,967, and
  Corynebacterium glutamicum DM1933 described in Blombach et al. (Appl Environ Microbiol. 2009 January; 75(2):419-27).

An example of an L-lysine-secreting or -producing strain of the species Corynebacterium efficiens is:
  Corynebacterium thermoaminogenes AJ12521 (=FERM BP-3304) described in U.S. Pat. No. 5,250,423.

L-lysine-producing microorganisms typically possess a "feedback"-resistant or densensitized aspartate kinase. "Feedback"-resistant aspartate kinases mean aspartate kinases (LysC) which, in comparison with the wild form (wild type), are less sensitive to inhibition by mixtures of lysine and threonine or mixtures of AEC (aminoethylcysteine) and threonine or lysine alone or AEC alone. The genes or alleles coding for these, compared to the wild type, desensitized aspartate kinases are also referred to as lysC$^{FBR}$ alleles. The wild type suitable in the case of the aspartate kinases of the species Corynebacterium glutamicum is the strain ATCC13032. The prior art describes numerous lysC$^{FBR}$ alleles which code for aspartate kinase variants which have amino acid substitutions in comparison with the wild-type protein. The lysC gene in bacteria of the genus Corynebacterium is also referred to as ask gene. The lysC gene-encoded aspartate kinase in Enterobacteriaceae is also referred to as aspartokinase III.

A detailed list with information about amino acid substitutions in the Corynebacterium glutamicum aspartate kinase protein that result in densensitization is included inter alia in WO2009141330A1 (page 10, line 21 to page 13, line 17) which is incorporated herein by reference. Preference is given to aspartate kinase variants carrying the following amino acid substitutions selected from the group consisting of: L-isoleucine for L-threonine in position 380 of the amino acid sequence and optionally L-phenylalanine for L-serine in position 381, L-isoleucine for L-threonine in position 311 and L-threonine for L-alanine in position 279.

An example of an L-methionine-secreting or -producing strain of the species Corynebacterium glutamicum is
  Corynebacterium glutamicum M1179 (=DSM 17322) described in WO 2007/011939.

Examples of known representatives of L-tryptophan-producing or -secreting strains of coryneform bacteria are:
  Corynebacterium glutamicum K76 (=Ferm BP-1847) described in U.S. Pat. No. 5,563,052,
  Corynebacterium glutamicum BPS13 (=Ferm BP-1777) described in U.S. Pat. No. 5,605,818, and
  Corynebacterium glutamicum Ferm BP-3055 described in U.S. Pat. No. 5,235,940.

Examples of known representatives of L-valine-producing or -secreting strains of coryneform bacteria are:
  Brevibacterium lactofermentum FERM BP-1763 described in U.S. Pat. No. 5,188,948,
  Brevibacterium lactofermentum FERM BP-3007 described in U.S. Pat. No. 5,521,074,
  Corynebacterium glutamicum FERM BP-3006 described in U.S. Pat. No. 5,521,074, and
  Corynebacterium glutamicum FERM BP-1764 described in U.S. Pat. No. 5,188,948.

L-valine-producing microorganisms typically possess a "feedback"-resistant or densensitized acetolactate synthase (AHAS, EC 4.1.3.18) which is the first enzyme of the parallel metabolic pathways for synthesizing isoleucine, valine and leucine (Umbarger, H. E. 1987. Biosynthesis of the branched-chain amino acids, p. 352-367. In F. C. Neidhardt, J. L. Ingraham, K. B. Low, B. Magasanik, M. Schaechter, and H. E. Umbarger (ed.), Escherichia coli and Salmonella typhimurium: Cellular and Molecular Biology. American Society for Microbiology, Washington, D.C.). The holoenzyme always consists of two large and two small subunits. The large AHAS subunit forms the catalytic domain and is encoded by ilvB, with the small subunit which acts as regulatory domain being encoded by ilvN. "Feedback"-resistant acetolactate synthases mean acetolactate synthases which, compared to the wild form (wild type), are less sensitive to inhibition by the branched-chain amino acids valine, leucine and isoleucine or mixtures thereof. The wild type suitable in the case of the acetolactate synthases of the species Corynebacterium glutamicum is the strain ATCC13032, and the wild type suitable within the species Brevibacterium flavum is the strain ATCC14067.

The ilvBN genes coding for acetolactate synthase in Corynebacterium glutamicum have been described, for example, by Keilhauer et al. (Journal of Bacteriology 175 (17):5595-603 (1993)) or in EP1108790. Access number L09232 depicts the sequence of said genes.

AHAS variant enzymes which are no longer subject to feedback inhibition by the branched-chain amino acids (leucine, valine, isoleucine) are described, for example, in Mendel et al. (Journal of Molecular Biology 325, 275-284 (2003)), Elisakova et al. (Applied and Environmental Microbiology 71, 207-213 (2005)), Wada et al. (Bioscience Biotechnology & Biochemistry, 72 (11), 2959-2965, (2008)) and in EP1491634. Preference is given to variants of a "feedback"-resistant acetolactate synthase which carry one or more of the following amino acid substitutions in the ilvN-encoded small subunit, selected from the group consisting of: L-aspartic acid for glycine in position 20 of the amino acid sequence, L-aspartic acid for L-isoleucine in position 21 of the amino acid sequence, L-phenylalanine for L-isoleucine in position 22 of the amino acid sequence, any proteinogenic amino acid except L-alanine, preferably L-valine, L-isoleucine and L-leucine, particularly preferably L-valine in position 42 and optionally L-leucine in position 47 for L-histidine.

Examples of known representatives of L-isoleucine-producing or -secreting strains of coryneform bacteria are:
- *Brevibacterium flavum* FERM BP-760 described in U.S. Pat. No. 4,656,135,
- *Brevibacterium flavum* FERM BP-2215 described in U.S. Pat. No. 5,294,547, and
- *Corynebacterium glutamicum* FERM BP-758 described in U.S. Pat. No. 4,656,135.

Examples of known representatives of L-homoserine-producing or -secreting strains of coryneform bacteria are:
- *Micrococcus glutamicus* ATCC 14296 described in U.S. Pat. No. 3,189,526 and
- *Micrococcus glutamicus* ATCC 14297 described in U.S. Pat. No. 3,189,526.

Examples of known representatives of L-ornithine-secreting or -producing strains of the species *Corynebacterium glutamicum* are:
- *Brevibacterium lactofermentum* FERM-BP 2344 described in U.S. Pat. No. 5,188,947 and
- *Corynebacterium glutamicum* FERM-BP 2345 described in U.S. Pat. No. 5,188,947.

α-keto acid-secreting or -producing strains are based on, for example:
- *Corynebacterium glutamicum*, strain ATCC13032,
- *Brevibacterium flavum*, strain ATCC 14067 and
- *Brevibacterium lactofermentum*, strain ATCC 13869.

The present invention provides a microorganism which produces a fine chemical, said microorganism having increased expression of one or more genes in comparison to the particular starting strain by using the promoter according to the invention of SEQ ID NO:3 or SEQ ID NO:34.

The present invention furthermore provides a process for fermentative preparation of a fine chemical, comprising the steps of:
a) Culturing the above-described microorganism according to the present invention in a suitable medium, resulting in a fermentation broth, and
b) Concentrating the fine chemical in the fermentation broth of a) and/or in the cells of the microorganism.

Preference is given here to obtaining from the fine chemical-containing fermentation broth the fine chemical or a liquid or solid fine chemical-containing product.

The microorganisms produced may be cultured continuously—as described, for example, in WO 05/021772—or discontinuously in a batch process (batch cultivation) or in a fed-batch or repeated fed-batch process for the purpose of producing the desired organic-chemical compound. A summary of a general nature about known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium or fermentation medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981). The terms culture medium and fermentation medium or medium are interchangeable.

It is possible to use, as carbon source, sugars and carbohydrates such as, for example, glucose, sucrose, lactose, fructose, maltose, molasses, sucrose-containing solutions from sugar beet or sugar cane processing, starch, starch hydrolysate and cellulose, oils and fats such as, for example, soybean oil, sunflower oil, groundnut oil and coconut fat, fatty acids such as, for example, palmitic acid, stearic acid and linoleic acid, alcohols such as, for example, glycerol, methanol and ethanol, and organic acids such as, for example, acetic acid or lactic acid.

It is possible to use, as nitrogen source, organic nitrogen-containing compounds such as peptones, yeast extract, meat extract, malt extract, corn steep liquor, soybean flour and urea, or inorganic compounds such as ammonium sulphate, ammonium chloride, ammonium phosphate, ammonium carbonate and ammonium nitrate. The nitrogen sources can be used individually or as a mixture.

It is possible to use, as phosphorus source, phosphoric acid, potassium dihydrogen phosphate or dipotassium hydrogen phosphate or the corresponding sodium-containing salts.

The culture medium must additionally comprise salts, for example in the form of chlorides or sulphates of metals such as, for example, sodium, potassium, magnesium, calcium and iron, such as, for example, magnesium sulphate or iron sulphate, which are necessary for growth. Finally, essential growth factors such as amino acids, for example homoserine and vitamins, for example thiamine, biotin or pantothenic acid, may be employed in addition to the abovementioned substances.

Said starting materials may be added to the culture in the form of a single batch or be fed in during the cultivation in a suitable manner.

The pH of the culture can be controlled by employing basic compounds such as sodium hydroxide, potassium hydroxide, ammonia or aqueous ammonia, or acidic compounds such as phosphoric acid or sulphuric acid in a suitable manner. The pH is generally adjusted to a value of from 6.0 to 8.5, preferably 6.5 to 8. To control foaming, it is possible to employ antifoams such as, for example, fatty acid polyglycol esters. To maintain the stability of plasmids, it is possible to add to the medium suitable selective substances such as, for example, antibiotics. The fermentation is preferably carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired organic-chemical compound sufficient for being recovered has formed. This aim is normally achieved within 10 hours to 160 hours. In continuous processes, longer cultivation times are possible. The activity of the microorganisms results in a concentration (accumulation) of the organic-chemical compound in the fermentation medium and/or in the cells of said microorganisms.

Examples of suitable fermentation media can be found inter alia in the U.S. Pat. No. 5,770,409, U.S. Pat. No. 5,990,350, U.S. Pat. No. 5,275,940, WO 2007/012078, U.S. Pat. No. 5,827,698, WO 2009/043803, U.S. Pat. No. 5,756,345 and U.S. Pat. No. 7,138,266.

Analysis of L-amino acids to determine the concentration at one or more time(s) during the fermentation can take place by separating the L-amino acids by means of ion exchange chromatography, preferably cation exchange chromatography, with subsequent post-column derivatization using ninhydrin, as described in Spackman et al. (Analytical Chemistry 30: 1190-1206 (1958)). It is also possible to employ orthophthaldialdehyde rather than ninhydrin for post-column derivatization. An overview article on ion exchange chromatography can be found in Pickering (LC•GC (Magazine of Chromatographic Science) 7(6), 484-487 (1989)).

It is likewise possible to carry out a pre-column derivatization, for example using ortho-phthadialdehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51: 1167-1174 (1979)).

Detection is carried out photometrically (absorption, fluorescence).

A review regarding amino acid analysis can be found inter alia in the textbook "Bioanalytik" from Lottspeich and Zorbas (Spektrum Akademischer Verlag, Heidelberg, Germany 1998).

The analysis of determining the concentration of α-keto acids at one or more point(s) in the course of the fermentation may be carried out by separating the keto acids and other secreted products by means of ion exchange chromatography, preferably cation exchange chromatography, on a sulphonated styrene-divinylbenzene polymer in the H+ form, for example by means of 0.025 M sulphuric acid with subsequent UV detection at 215 nm (alternatively also at 230 or 275 nm). Preferably, a REZEK RFQ—Fast Fruit H+ column (Phenomenex) may be employed, but other suppliers for the separating phase (e.g. Aminex from BioRad) are feasible. Similar separations are described in corresponding application examples by the suppliers.

The performance of the processes or fermentation processes containing the promoter variant according to the invention, in terms of one or more of the parameters selected from the group of concentration (compound formed per unit volume), yield (compound formed per unit carbon source consumed), formation (compound formed per unit volume and time) and specific formation (compound formed per unit dry cell matter or dry biomass and time or compound formed per unit cellular protein and time) or else other process parameters and combinations thereof, is increased by at least 0.5%, at least 1%, at least 1.5% or at least 2%, based on processes or fermentation processes using microorganisms not containing the promoter variant according to the invention. This is considered to be very worthwhile in terms of a large-scale industrial process.

The fermentation measures result in a fermentation broth which contains the desired fine chemical, preferably amino acid or organic acid.

A product containing the fine chemical is then provided or produced or recovered in liquid or solid form.

A fermentation broth means a fermentation medium or nutrient medium in which a microorganism has been cultivated for a certain time and at a certain temperature. The fermentation medium or the media employed during fermentation comprise(s) all the substances or components which ensure production of the desired compound and typically propagation and viability.

When the fermentation is complete, the resulting fermentation broth accordingly comprises
a) the biomass (cell mass) of the microorganism, said biomass having been produced due to propagation of the cells of said microorganism,
b) the desired fine chemical formed during the fermentation,
c) the organic byproducts possibly formed during the fermentation, and
d) the constituents of the fermentation medium employed or of the starting materials, such as, for example, vitamins such as biotin or salts such as magnesium sulphate, which have not been consumed in the fermentation.

The organic byproducts include substances which are produced by the microorganisms employed in the fermentation in addition to the particular desired compound and are optionally secreted.

The fermentation broth is removed from the culture vessel or fermentation tank, collected where appropriate, and used for providing a product containing the fine chemical in liquid or solid form. The expression "recovering the fine chemical-containing product" is also used for this. In the simplest case, the fine chemical-containing fermentation broth itself, which has been removed from the fermentation tank, constitutes the recovered product.

One or more of the measures selected from the group consisting of
a) partial (>0% to <80%) to complete (100%) or virtually complete (≥80%, ≥90%, ≥95%, ≥96%, ≥97%, ≥98%, ≥99%) removal of the water,
b) partial (>0% to <80%) to complete (100%) or virtually complete (≥80%, ≥90%, ≥95%, ≥96%, ≥97%, ≥98%, ≥99%) removal of the biomass, the latter being optionally inactivated before removal,
c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic byproducts formed during fermentation, and
d) partial (>0%) to complete (100%) or virtually complete (≥80%, ≥90%, ≥95%, ≥96%, ≥97%, ≥98%, ≥99%, ≥99.3%, ≥99.7%) removal of the constituents of the fermentation medium employed or of the starting materials, which have not been consumed in the fermentation,
from the fermentation broth achieves concentration or purification of the desired organic-chemical compound. Products having a desired content of said compound are isolated in this way.

The partial (>0% to <80%) to complete (100%) or virtually complete (≥80% to <100%) removal of the water (measure a)) is also referred to as drying.

In one variant of the process, complete or virtually complete removal of the water, of the biomass, of the organic byproducts and of the unconsumed constituents of the fermentation medium employed results in pure (≥80% by weight, ≥90% by weight) or high-purity (≥95% by weight, ≥97% by weight, ≥99% by weight) product forms of the desired organic-chemical compound, preferably L-amino acids. An abundance of technical instructions for measures a), b), c) and d) are available in the prior art.

In the case of the amino acid L-lysine, essentially four different product forms are known in the prior art.

One group of L-lysine-containing products includes concentrated aqueous alkaline solutions of purified L-lysine (EP-B-0534865). A further group, as described for example in U.S. Pat. No. 6,340,486 and U.S. Pat. No. 6,465,025, includes aqueous acidic biomass-containing concentrates of L-lysine-containing fermentation broths. The best-known group of solid products includes pulverulent or crystalline forms of purified or pure L-lysine, which is typically in the form of a salt such as, for example, L-lysine monohydrochloride. A further group of solid product forms is described for example in EP-B-0533039. The product form described therein comprises besides L-lysine most of the starting materials used during the fermentative production and not consumed and, where appropriate, the biomass of the microorganism employed with a proportion of >0%-100%.

A wide variety of processes appropriate for the various product forms are known for producing the L-lysine-containing product or the purified L-lysine from the fermentation broth.

The methods essentially used to produce pure solid L-lysine are those of ion exchange chromatography, where appropriate with use of activated carbon, and methods of crystallization. The corresponding base or a corresponding salt such as, for example, the monohydrochloride (Lys-HCl) or the lysine sulphate ($Lys_2$-$H_2SO_4$) is obtained in this way.

EP-B-0534865 describes a process for producing aqueous basic L-lysine-containing solutions from fermentation broths. In the process described therein, the biomass is separated from the fermentation broth and discarded. A base such as, for example, sodium hydroxide, potassium hydroxide or ammonium hydroxide is used to set a pH of between 9 to 11. The mineral constituents (inorganic salts) are removed from the broth by crystallization after concentration and cooling and are either used as fertilizer or discarded.

In processes for producing lysine by using bacteria of the genus *Corynebacterium*, preferred processes are those resulting in products which comprise constituents of the fermentation broth. These are used in particular as animal feed additives.

Depending on requirements, the biomass can be removed wholly or partly from the fermentation broth by separation methods such as, for example, centrifugation, filtration, decantation or a combination thereof, or be left completely therein. Where appropriate, the biomass or the biomass-containing fermentation broth is inactivated during a suitable process step, for example by thermal treatment (heating) or by addition of acid.

In one procedure, the biomass is completely or virtually completely removed so that no (0%) or at most 30%, at most 20%, at most 10%, at most 5%, at most 1% or at most 0.1% biomass remains in the prepared product. In a further procedure, the biomass is not removed, or is removed only in small proportions, so that all (100%) or more than 70%, 80%, 90%, 95%, 99% or 99.9% biomass remains in the product prepared. In one process according to the invention, accordingly, the biomass is removed in proportions of from ≥0% to ≤100%.

Finally, the fermentation broth obtained after the fermentation can be adjusted, before or after the complete or partial removal of the biomass, to an acidic pH with an inorganic acid such as, for example, hydrochloric acid, sulphuric acid or phosphoric acid, or organic acid such as, for example, propionic acid, so as to improve the handling properties of the final product (GB 1,439,728 or EP 1 331 220). It is likewise possible to acidify the fermentation broth with the complete content of biomass. Finally, the broth can also be stabilized by adding sodium bisulphite ($NaHSO_3$, GB 1,439,728) or another salt, for example ammonium, alkali metal or alkaline earth metal salt of sulphurous acid.

During the removal of the biomass, any organic or inorganic solids present in the fermentation broth are partially or completely removed. The organic byproducts dissolved in the fermentation broth, and the dissolved unconsumed constituents of the fermentation medium (starting materials), remain at least partly (>0%), preferably to an extent of at least 25%, particularly preferably to an extent of at least 50% and very particularly preferably to an extent of at least 75% in the product. Where appropriate, they also remain completely (100%) or virtually completely, meaning >95% or >98% or greater than 99%, in the product. If a product in this sense comprises at least part of the constituents of the fermentation broth, this is also described by the term "product based on fermentation broth".

Subsequently, water is removed from the broth, or said broth is thickened or concentrated, by known methods such as, for example, using a rotary evaporator, thin-film evaporator, falling-film evaporator, by reverse osmosis or by nanofiltration. This concentrated fermentation broth can then be worked up to free-flowing products, in particular to a fine powder or preferably coarse granules, by methods of freeze drying, spray drying, spray granulation or by other processes such as in the circulating fluidized bed, as described for example according to PCT/EP2004/006655. A desired product is isolated where appropriate from the resulting granules by screening or dust removal.

It is likewise possible to dry the fermentation broth directly, i.e. without previous concentration by spray drying or spray granulation.

"Free-flowing" means powders which, from a series of glass orifice vessels with orifices of different sizes, flow unimpeded at least out of the vessel with a 5 mm (millimeters) orifice (Klein: Seifen, Öle, Fette, Wachse 94, 12 (1968)).

"Fine" means a powder predominantly (>50%) having a particle size of diameter from 20 to 200 μm.

"Coarse" means a product predominantly (>50%) of a particle size of diameter from 200 to 2000 μm.

The particle size determination can be carried out by methods of laser diffraction spectrometry. Corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, fine powder can in turn be converted by suitable compaction or granulation processes into a coarse, very free-flowing, storable and substantially dust-free product.

The term "dust-free" means that the product comprises only small proportions (<50) of particle sizes below 100 μm in diameter.

"Storable" in the sense of this invention means a product which can be stored for at least one (1) year or longer, preferably at least 1.5 years or longer, particularly preferably two (2) years or longer, in a dry and cool environment without any substantial loss of the respective amino acid occurring. "Substantial loss" means a loss of >5%.

The invention further relates to a process described in principle in WO 2007/042363 A1. To this end, a process is carried out which uses the fermentation broth obtained according to the invention, from which the biomass has been removed completely or partially, where appropriate, and which comprises the following steps:

a) the pH is reduced to 4.0 to 5.2, in particular 4.9 to 5.1, by adding sulphuric acid and a molar sulphate/L-lysine ratio of from 0.85 to 1.2, preferably 0.9 to 1.0, particularly preferably >0.9 to <0.95, is established in the broth, where appropriate by adding one or more further sulphate-containing compound(s), and b) the mixture obtained in this way is concentrated by removal of water, and granulated where appropriate, where one or both of the following measures is/are carried out where appropriate before step a):

c) measurement of the molar sulphate/L-lysine ratio to ascertain the required amount of sulphate-containing compound(s)

d) addition of a sulphate-containing compound selected from the group of ammonium sulphate, ammonium bisulphate and sulphuric acid in appropriate ratios.

Where appropriate, also before step b), a salt of sulphurous acid, preferably alkali metal bisulphite, particularly preferably sodium bisulphite, is added in a concentration of from 0.01 to 0.5% by weight, preferably 0.1 to 0.3% by weight, particularly preferably 0.1 to 0.2% by weight, based on the fermentation broth.

Preferred sulphate-containing compounds which should be mentioned in the context of the abovementioned process steps are in particular ammonium sulphate and/or ammonium bisulphate or appropriate mixtures of ammonia and sulphuric acid and sulphuric acid itself.

The molar sulphate/L-lysine ratio V is calculated by the formula: $V=2\times[SO_4^{2-}]/[L\text{-lysine}]$. This formula takes account of the fact that the $SO_4^{2-}$ anion and sulphuric acid are divalent. A ratio of V=1 means that a stoichiometric composition $Lys_{2-}$ ($H_2SO_4$) is present, whereas the finding with a ratio of V=0.9 is a 10% sulphate deficit and with a ratio of V=1.1 is a 10% sulphate excess.

It is advantageous to employ during the granulation or compaction the usual organic or inorganic auxiliaries or carriers such as starch, gelatine, cellulose derivatives or similar substances, as normally used in the processing of food products or feeds as binders, gelling agents or thickeners, or further substances such as, for example, silicas, silicates (EP0743016A) and stearates.

It is further advantageous to treat the surface of the resulting granules with oils or fats as described in WO 04/054381. Oils which can be used are mineral oils, vegetable oils or mixtures of vegetable oils. Examples of such oils are soybean oil, olive oil, soybean oil/lecithin mixtures. In the same way, silicone oils, polyethylene glycols or hydroxyethylcellulose are also suitable. Treatment of the surfaces with said oils achieves an increased abrasion resistance of the product and a reduction in the dust content. The oil content in the product is 0.02 to 2.0% by weight, preferably 0.02 to 1.0% by weight, and very particularly preferably 0.2 to 1.0% by weight, based on the total amount of the feed additive.

Preferred products have a proportion of ≥97% by weight with a particle size of from 100 to 1800 μm or a proportion of ≥95% by weight with a particle size of diameter 300 to 1800 μm. The proportion of dust, i.e. particles with a particle size <100 μm, is preferably >0 to 1% by weight, particularly preferably not exceeding 0.5% by weight.

However, alternatively, the product may also be absorbed on an organic or inorganic carrier known and customary in the processing of feeds, such as, for example, silicas, silicates, meals, brans, flours, starches, sugars or others, and/or be mixed and stabilized with customary thickeners or binders. Examples of use and processes therefor are described in the literature (Die Mühle+Mischfuttertechnik 132 (1995) 49, page 817).

Finally, the product can also be brought, by coating processes with film-formers such as, for example, metal carbonates, silicas, silicates, alginates, stearates, starches, gums and cellulose ethers, as described in DE-C-4100920, into a state which is stable to digestion by animal stomachs, especially the stomach of ruminants.

To establish a desired L-lysine concentration in the product it is possible, depending on requirements, to add the L-lysine during the process in the form of a concentrate or, where appropriate, of a substantially pure substance or its salt in liquid or solid form. These can be added singly or as mixtures to the resulting or concentrated fermentation broth, or else during the drying or granulation process.

The invention further relates to a combination with a process for preparing a solid lysine-containing product, which process is described in principle in US 20050220933. This involves carrying out a process which uses the fermentation broth obtained according to the invention and which comprises the following steps:

a) filtration of the fermentation broth, preferably with a membrane filter, to result in a biomass-containing slurry and a filtrate,
b) concentration of the filtrate, preferably so as to result in a solids content of from 48 to 52% by weight,
c) granulation of the concentrate obtained in step b), preferably at a temperature of from 50° C. to 62° C., and
d) coating of the granules obtained in c) with one or more of the coating agent(s).

The coating agents preferably used for the coating in step d) are selected from the group consisting of
d1) the biomass obtained in step a),
d2) an L-lysine-containing compound, preferably selected from the group of L-lysine hydrochloride or L-lysine sulphate,
d3) an essentially L-lysine-free substance with an L-lysine content of <1% by weight, preferably <0.5% by weight, preferably selected from the group of starch, carrageenan, agar, silicas, silicates, meals, brans and flours, and
d4) a water-repellent substance, preferably selected from the group of oils, polyethylene glycols and liquid paraffins.

The L-lysine content is adjusted to a desired value by the measures corresponding to steps d1) to d4), in particular d1) to d3).

In the production of L-lysine-containing products, the ratio of the ions is preferably adjusted so that the molar ion ratio corresponding to the following formula

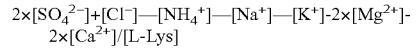

gives 0.68 to 0.95, preferably 0.68 to 0.90, particularly preferably 0.68 to 0.86, as described by Kushiki et al. in US 20030152633.

In the case of L-lysine, the solid product produced in this way has, based on the fermentation broth, a lysine content (as lysine base) of from 10% by weight to 70% by weight or 20% by weight to 70% by weight, preferably 30% by weight to 70% by weight and very particularly preferably from 40% by weight to 70% by weight, based on the dry matter of the product. Maximum lysine base contents of 71% by weight, 72% by weight, 73% by weight are likewise possible.

The water content of the L-lysine-containing solid product is up to 5% by weight, preferably up to 4% by weight, and particularly preferably less than 3% by weight.

Example 1

Sequencing of the Promoter Region of the DM1547 Gap Gene

The *Corynebacterium glutamicum* strain DM1547 was prepared by multiple, non-directed mutagenesis, selection and mutant choice from *C. glutamicum* ATCC13032. The strain is resistant to the lysine analogue S-(2-aminoethyl)-L-cysteine.

A pure culture of the DM1547 strain was deposited with the Deutsche Sammlung für Mikroorganismen und Zellkulturen (DSMZ, Braunschweig, Germany) as DSM 13994 in accordance with the Budapest Treaty on 16 Jan. 2001. The strain DSM 13994 is listed in EP 1 239 040.

The nucleotide sequence of the *Corynebacterium glutamicum* genome ATCC13032 is described in Ikeda and Nakagawa (Applied Microbiology and Biotechnology 62, 99-109 (2003)), in EP 1 108 790 and in Kalinowski et al.

(Journal of Biotechnology 104(1-3), (2003)). The nucleotide sequence of the *Corynebacterium glutamicum* R genome is described in Yukawa et al. (Microbiology 153(4):1042-1058 (2007)).

The nucleotide sequence of the *Corynebacterium efficiens* genome is described in Nishio et al (Genome Research. 13 (7), 1572-1579 (2003)).

The nucleotide sequences of the *Corynebacterium glutamicum* and *Corynebacterium efficiens* genomes are likewise available in the database of the National Center for Biotechnology Information (NCBI) of the National Library of Medicine (Bethesda, Md., USA), in the DNA Data Bank of Japan (DDBJ, Mishima, Japan), or in the nucleotide sequence database of the European Molecular Biologies Laboratories (EMBL, Heidelberg, Germany, and Cambridge, UK).

Chromosomal DNA was isolated from the strain DM1547 by the method of Eikmanns et al. (Microbiology 140: 1817-1828 (1994)). A DNA section containing the upstream region of the gap gene was amplified with the aid of the polymerase chain reaction. Owing to the known sequence of the *C. glutamicum* gap gene, the following oligonucleotides were used as primers:

```
Pgap3-1 (SEQ ID NO: 31):
5' cgtttggggtcaatgtccat 3'

Pgap3-2 (SEQ ID NO: 32):
5' cccagtccaggttctttg 3'
```

The primers shown were synthesized by MWG Biotech (Ebersberg, Germany). They enable a 529 bp DNA section to be amplified. The Pgap3-2 primer binds to the region corresponding to positions 742 to 759 of the strand complementary to SEQ ID NO:30 (and SEQ ID NO:33). The Pgap3-1 primer binds to the region corresponding to positions 231 to 250 of the strand of SEQ ID NO:30 (and SEQ ID NO:33).

The PCR reaction was carried out using the Phusion High Fidelity DNA polymerase (New England Biolabs, Frankfurt, Germany). The reaction mixture was prepared according to the manufacturer's information and contained in a total volume of 50 µl 10 µl of the supplied 5× Phusion HF Buffer, deoxynucleoside triphosphates at a concentration of 200 µm each, primers at a concentration of 0.5 µm, approximately 50 ng of template DNA and two units of Phusion Polymerase. The volume was adjusted to 50 µl by adding $H_2O$.

The PCR mixture was first subjected to an initial denaturation at 98° C. for 30 seconds. This was followed by 35 repeats of a denaturation step at 98° C. for 20 seconds, a step for binding the primers to the DNA presented at 60° C. for 20 seconds, and the extension step to extend the primers at 72° C. for 60 seconds. After the final extension step at 72° C. for 5 minutes, the PCR mixture was subjected to an agarose gel electrophoresis (0.8% agarose). A DNA fragment of approx. 0.53 kb in length was identified, isolated from the gel and purified using the QIAquick Gel Extraction kit from Qiagen (Hilden, Germany).

The nucleotide sequence of the amplified DNA fragment or PCR product was determined by Agowa (Berlin, Germany).

The nucleotide sequence of the promoter region of the strain DM1547 gap gene contains the nucleobase adenine in position 379 (see SEQ ID NO:33). The promoter region of the wild type (see SEQ ID NO:30) contains the nucleobase guanine in this position. This mutation is referred to as Pgap3 hereinbelow.

Example 2

Construction of the Vector pK18mobsacBIBcg0054

To characterize the mutation according to the invention, an upstream region of the gap gene, including the promoter, is used for enhancing a synthetic operon. The synthetic operon consists of a densensitized *Corynebacterium glutamicum* aspartate kinase encoded by an allele of the lysC gene, in which the wild-type nucleobase threonine has been replaced with the nucleobase isoleucine in position 311 of the encoded aspartate kinase protein (see WO 00/63388 and U.S. Pat. No. 6,893,848), and a *Corynebacterium glutamicum* aspartate-semialdehyde dehydrogenase encoded by the asd gene. Said synthetic operon is integrated via homologous recombination into an intergenic region within the *Corynebacterium glutamicum* chromosome in such a way that the insertion results in an increase in the copy number of the lysC and asd genes. A homologous DNA sequence which enables the synthetic operon to be incorporated was synthesized by Geneart AG (Regensburg, Germany). This DNA sequence is depicted in SEQ ID NO:35 and is denoted IBcg0054. The DNA sequence contains a 383 bp intergenic region flanked by a 595 bp region (cg0055 gene coding for a putative membrane protein and part of the cg0057 gene coding for a serine/threonine protein kinase) and a 663 bp region (part of the cg0054 gene coding for an iron uptake protein).

In addition to the restriction cleavage sites of the enzymes AvrII and NsiI, in a central position within the intergenic region for the insertion of various DNA sequences, flanking cleavage sites for the restriction endonucleases MunI and HindIII were generated for procedures of subcloning the entire fragment.

The 1660 bp Geneart fragment (SEQ ID NO:35) was digested with the restriction enzymes MunI and HindIII and then subcloned into the mobilizable vector pK18mobsacB described by Schäfer et al. (Gene, 145, 69-73 (1994)). For this, pK18mobsacB was digested with the restriction enzymes EcoRI and HindIII. The vector prepared in this way was mixed with the IBcg0054 fragment, and the mixture was treated with the Ready-To-Go T4 DNA Ligase Kit (Amersham-Pharmacia, Freiburg, Germany).

Subsequently, the *E. coli* strain S17-1 (Simon et al., Bio/Technologie 1: 784-791, 1993) was transformed with the ligation mixture (Hanahan, in DNA cloning. A practical approach. Vol. 1. ILR-Press, Cold Spring Harbor, N.Y., 1989). Plasmid-carrying cells were selected by plating the transformation mixture on LB agar (Sambrook et al., Molecular Cloning: a laboratory manual. $2^{nd}$ Ed. Cold Spring Harbor, N.Y., 1989) which had been supplemented with 50 mg/l kanamycin.

Plasmid DNA was isolated from a transformant with the aid of the Qiagen QIAprep Spin Miniprep Kit and checked by restriction cleavage with the enzymes EcoRI and HindIII and subsequent agarose gel elektrophoresis. The plasmid has the name pK18mobsacB_IBcg0054.

Example 3

Construction of the Replacement Vectors
pK18mobsacB_PgapWT_lysCT311I_asd,
pK18mobsacB_Pgap3_lysCT311I_asd and
pK18mobsacB_Pg3N3_lysCT311I_asd The mutation in the upstream region of the gap gene is characterized on the basis of a DNA cassette containing a synthetic operon of the lysC and asd genes under the control of the respective promoters PgapWT, Pgap3 and Pg3N3, which is inserted into the intergenic region described in example 2. The synthetic operons were synthesized by Geneart AG (Regensburg, Germany) and are named PgapWT_lysCT311I_asd, Pgap3_lysCT311I_asd and Pg3N3_lysCT311I_asd, respectively. The DNA sequences are depicted in Seq ID No:36, for PgapWT_lysCT311I_asd, in Seq ID No:37, for Pgap3_lysCT311I_asd, and in Seq ID No:38, for Pg3N3_lysCT311I_asd, respectively.

The promoter region of the gap gene comprises positions 9 to 469, the sequence of the constructs in this region corresponding in each case to the sequences depicted in Seq ID No:2 (for PgapWT), in Seq ID No:3 (for Pgap3) or Seq ID No:34 (for Pg3N3). This is followed downstream by the coding sequence of a desensitized *Corynebacterium glutamicum* aspartate kinase encoded by an allele of the lysC gene, in which the wild-type nucleobase threonine has been replaced with the nucleobase isoleucine in position 311 of the encoded aspartate kinase protein (see WO 00/63388 and U.S. Pat. No. 6,893,848). In addition, the nucleobase guanine was replaced with the nucleobase adenine within the lysC start codon. This is followed again downstream by the coding sequence of *Corynebacterium glutamicum* aspartate-semialdehyde dehydrogenase, encoding the asd gene. The ribosome-binding site of the gap gene is located upstream of the two genes lysC and asd in each case (upstream of lysC in the form of Seq ID No:16, upstream of asd in the form of Seq ID No:26), and the termination sequence of the gap gene is located downstream of asd.

Restriction cleavage sites of the enzymes AvrII and NsiI flanking the synthetic operon were generated for subcloning procedures.

The fragments were cleaved with the restriction enzymes AvrII and NsiI and then subcloned into the mobilizable vector pK18mobsacB_IBcg0054 described in example 2. For this, pK18mobsacB_IBcg0054 was digested with the restriction enzymes AvrII and NsiI. The vector prepared in this way was mixed with the PgapWT_lysCT311I_asd, Pgap3_lysCT311I_asd or Pg3N3_lysCT311I_asd fragments, and the mixture was treated with the Ready-To-Go T4 DNA Ligase Kit (Amersham-Pharmacia, Freiburg, Germany).

Subsequently, the *E. coli* strain S17-1 (Simon et al., Bio/Technologie 1: 784-791, 1993) was transformed with the ligation mixture (Hanahan, In. DNA cloning. A practical approach. Vol. 1. ILR-Press, Cold Spring Harbor, N.Y., 1989). Plasmid-carrying cells were selected by plating the transformation mixture on LB agar (Sambrock et al., Molecular Cloning: a laboratory manual. 2$^{nd}$ Ed. Cold Spring Harbor, N.Y., 1989) which had been supplemented with 50 mg/l kanamycin.

Plasmid DNA was isolated from a transformant with the aid of the Qiagen QIAprep Spin Miniprep Kit and checked by restriction cleavage with the enzymes AvrII and NsiI and subsequent agarose gel electrophoresis. Depending on the gap-promoter allele, the plasmids are named pK18mobsacB_PgapWT_lysCT311I_asd, pK18mobsacB_Pgap3_lysCT311I_asd and pK18mobsacB_Pg3N3_lysCT311I_asd, respectively. pK18mobsacB_Pgap3_lysCT311I_asd is depicted in FIG. 1 by way of example.

Example 4

Preparation of the *C. glutamicum* Strains DM1729_PgapWT_lysCT311I_asd, DM1729_Pgap3_lysCT311I_asd and DM1729_Pg3N3_lysCT311I_asd The mutations PgapWT_lysCT311I_asd, Pgap3_lysCT311I_asd and Pg3N3_lysCT311I_asd are intended to be introduced into the strain *Corynebacterium glutamicum* DM1729. The strain DM1729 is an aminoethyl-cysteine-resistant mutant of *Corynebacterium glutamicum* ATCC13032 and is described in the patent application EP 1 717 616 A2 and in Georgi et al. (Metabolic Engineering 7, 291-301 (2005)). It has been deposited under the name DSM17576 with the Deutsche Sammlung für Mikroorganismen and Zellkulturen (DSMZ, Braunschweig, Germany).

The vectors described in example 3, pK18mobsacB_PgapWT_lysCT311I_asd, pK18mobsacB_Pgap3_lysCT311I_asd and pK18mobsacB_Pg3N3_lysCT311I_asd, were transferred by conjugation into the *C. glutamicum* strain DM1729 according to the protocol by Schafer et al. (Journal of Microbiology 172: 1663-1666 (1990)). The vector cannot self-replicate in DM1729 and is retained in the cell only if it has been integrated into the chromosome as the result of a recombination event. Transconjugants, i.e. clones with integrated pK18mobsacB_PgapWT_lysCT311I_asd, pK18mobsacB_Pgap3_lysCT311I_asd or pK18mobsacB_Pg3N3_lysCT311I_asd, were selected by plating the conjugation mixture on LB agar which had been supplemented with 25 mg/l kanamycin and 50 mg/l nalidixic acid. Kanamycin-resistant transconjugants were then straightened out on kanamycin (25 mg/l)-supplemented LB agar plates and incubated at 33° C. for 24 hours. Mutants in which the plasmid had been excised due to a second recombination event were selected by culturing the clones non-selectively in LB liquid medium for 30 hours, followed by straightening them out on LB agar which had been supplemented with 10% sucrose, and incubating them at 33° C. for 24 hours.

Like the starting plasmid pK18mobsacB, the plasmids pK18mobsacB_PgapWT_lysCT311I_asd, pK18mobsacB_Pgap3_lysCT311I_asd and pK18mobsacB_Pg3N3_lysCT311I_asd include, in addition to the kanamycin-resistance gene, a copy of the sacB gene coding for *Bacillus subtilis* levansucrase. Sucrose-inducible expression of the sacB gene results in the formation of levansucrase which catalyses the synthesis of the product levan which is toxic to *C. glutamicum*. Consequently, only those clones in which the integrated pK18mobsacB_PgapWT_lysCT311I_asd, pK18mobsacB_Pgap3_lysCT311I_asd or pK18mobsacB_Pg3N3_lysCT311I_asd has been excised due to a second recombination event grow on sucrose-supplemented LB agar. Depending on the position of the second recombination event with respect to the site of mutation, excision comprises allele replacement or incorporation of the mutation, or the original copy is retained in the chromosome of the host.

Screening was then carried out in each case for a clone in which the desired replacement, i.e. incorporation of the cassette PgapWT_lysCT311I_asd, Pgap3_lysCT311I_asd or Pg3N3_lysCT311I_asd into the intergenic region, had taken place.

To this end, in each case 20 clones with the phenotype "Growth in the presence of sucrose" and "No growth in the presence of kanamycin" were checked for integration of the cassette PgapWT_lysCT311I_asd, Pgap3_lysCT311I_asd or Pg3N3_lysCT311I_asd using the polymerase chain reaction (PCR).

For this, the following synthetic oligonucleotides (primers) were used:

```
Primer cg0054_9.p (SEQ ID No. 39):
5' CCACCCATCACCCTCACTTC 3'

Primer cg0054_10.p (SEQ ID No. 40):
5' GCACTCTCGTTTGGCAGTTC 3'

Primer QlysC_WT_P2 (SEQ ID No. 41):
5' AAGTGCCGGGATCATTACTA 3'
```

The primers shown were synthesized by MWG Biotech (Ebersberg, Germany). The primers cg0054_9.p and cg0054_10.p enable a 1032 bp DNA fragment to be amplified if the wild-type arrangement is present in the intergenic region. Using a further primer (QlysC_WT_P2) in the same reaction mixture, which is capable of annealing to the lysC gene, enables a 1330 bp DNA fragment to be amplified, whereby integration of the synthetic operon PgapWT_lysCT311I_asd, Pgap3_lysCT311I_asd or Pg3N3_lysCT311I_asd into the intergenic region IBcg0054 is specifically detected. Under the conditions chosen for the PCR reaction, the combination of primers cg0054_9.p and cg0054_10.p does not result in an amplicon in the case of integration into the intergenic region. In addition, PCR reactions which have not yielded an amplicon for technical reasons are identified with the aid of the detection reactions described.

The PCR reactions were carried out using the Tag PCR Core Kit from Qiagen (Hilden, Germany), containing the *Thermus aquaticus* Tag DNA polymerase, in a mastercycler from Eppendorf (Hamburg, Germany). The conditions in the reaction mixture were adjusted according to the manufacturer's information. The PCR mixture was first subjected to an initial denaturation at 94° C. for two minutes. This was followed by 35 repeats of a denaturation step at 94° C. for 30 seconds, a step of binding the primers to the DNA at 57° C. for 30 seconds, and the extension step for extending the primers at 72° C. for 60 s. After the final extension step at 72° C. for 5 min, the products amplified in this way were checked by electrophoresis in an agarose gel.

In this manner, mutants were identified, in which the cassette PgapWT_lysCT311I_asd, Pgap3_lysCT311I_asd or Pg3N3_lysCT311I_asd has been integrated, with one of the strains *C. glutamicum* obtained in each case being named DM1729_PgapWT_lysCT311I_asd, DM1729_Pgap3_lysCT311I_asd and DM1729_Pg3N3_lysCT311I_asd.

Example 5

Preparation of L-lysine

The *C. glutamicum* strains obtained in example 4, DM1729_PgapWT_lysCT311I_asd, DM1729_Pgap3_lysCT311I_asd and DM1729_Pg3N3_lysCT311I_asd, and the starting strain DM1729 were cultured in a nutrient medium suitable for producing lysine, and the lysine content in the culture supernatent was determined.

For this purpose, the clones were first propagated on brain-heart agar plates (Merck, Darmstadt, Germany) at 33° C. for 24 hours. Starting from these agar plate cultures, in each case a preculture was inoculated (10 ml medium in a 100 ml conical flask). The medium used for the preculture was MM medium. The preculture was incubated at 33° C. on a shaker at 240 rpm for 24 hours. A main culture was inoculated from this preculture such that the starting OD (660 nm) of the main culture was 0.1 OD. MM medium was also used for the main culture.

MM Medium

| | |
|---|---|
| CSL | 5 g/l |
| MOPS | 20 g/l |
| Glucose (autoclaved separately) | 50 g/l |

Salts:

| | |
|---|---|
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| $CaCO_3$ | 25 g/l |

CSL (corn steep liquor), MOPS (morpholinopropanesulphonic acid) and the salt solution were adjusted to pH 7 with aqueous ammonia and autoclaved. The sterile substrate and vitamin solutions and the dry-autoclaved $CaCO_3$ were then added.

Culturing was carried out in volumes of 10 ml in 100 ml conical flasks with baffles. The temperature was 33° C., with 250 revolutions per minute and a humidity of 800.

After 24 hours the optical density (OD) was measured at a wavelength of 660 nm using a Biomek 1000 (Beckmann Instruments GmbH, Munich). The amount of lysine formed was determined using an amino acid analyser from Eppendorf-BioTronik (Hamburg, Germany) by ion exchange chromatography and post-column derivatization with ninhydrin detection.

The result of the experiment is depicted in Table 1.

TABLE 1

Preparation of L-lysine

| Strain | L-lysine HCl (g/l) | OD (660 nm) |
|---|---|---|
| DM1729 (starting strain) | 9.9 | 14.9 |
| DM1729_PgapWT_lysCT311I_asd | 12.5 | 13.9 |
| DM1729_Pgap3_lysCT311I_asd | 12.8 | 13.2 |
| DM1729_Pg3N3_lysCT311I_asd | 13.2 | 12.9 |

All values are averages of three independent experiments with the strains listed The result indicates the positive effect on the formation of the desired product (L-lysine) due to using the promoter variants according to the invention, Pgap3 and Pg3N3, with respect to the starting strains mentioned above.

Example 6

Construction of the Replacement Vector pK18mobsacB_IBcg0054_Pg3_argJB

Starting from the genomic sequence of *Corynebacterium glutamicum* ATCC13032, a 2722 bp DNA fragment was synthesized at GeneArt (Regensburg, Germany) (Seq ID: 29), which carries the Pgap3 promoter and the genes argJ (coding for a glutamate N-acetyltransferase) and argB (coding for an acetylglutamate kinase). The promoter region of the gap gene comprises positions 10 to 470, with the sequence of the construct in this region corresponding to the sequence depicted in Seq ID No:3 (for Pgap3). This is followed downstream by the coding sequences for a glutamate N-acetyltransferase and an acetylglutamate kinase from *Corynebacterium glutamicum*. The fragment was cut by SphI and BlnI cleavage via the terminally introduced cleavage sites SphI and BlnI and then cloned into the vector pK18mobsacB_IBcg0054 (from example 2) which had been cut likewise with SphI and BlnI. The plasmid is named pK18mobsacB_IBcg0054_Pg3_argJB.

Example 7

Preparation of the *C. glutamicum* Strain *Corynebacterium glutamicum* ATCC13032_DargFRGH_Pg3 argJB The vector mentioned in example 6, pK18mobsacB_IBcg0054_Pg3_argJB, was transferred into the *Corynebacterium glutamicum* strain ATCC13032_DargFRGH (from patent application DE102010003419.3) by means of conjugation according to a protocol by Schafer et al. (Journal of Microbiology 172: 1663-1666 (1990)), analogous to example 4.

For this purpose, the vector was first transformed into the *E. coli* S17-1 strain (Simon et al., Biotechnology 1:784-791). The vector pK18mobsacB or pK18mobsacB_IBcg0054_Pg3_argJB cannot self-replicate in *C. glutamicum* ATCC13032 and is retained in the cell only if it has integrated into the chromosome as the result of a recombination event. Clones with integrated pK18mobsacB_IBcg0054_Pg3_argJB are selected by plating the conjugation mixture on LB agar (Sambrook et al., Molecular Cloning: A Laboratory Manual, 2nd Ed., Cold Spring Harbor, N.Y., 1989) supplemented with 15 mg/l kanamycin and 50 mg/ml nalidixic acid. 15 established clones are straightened out on LB agar plates containing 25 mg/l kanamycin and incubated at 33° C. for 16 hours. To select mutants in which the plasmid has been excised due to a second recombination event, the clones are cultured non-selectively in LB liquid medium for 20 hours, then straightened out on LB agar containing 10% sucrose and incubated for 24 hours. Like the starting plasmid pK18mobsacB, the pK18mobsacB_IBcg0054_Pg3_argJB plasmid includes, in addition to the kanamycin-resistance gene, a copy of the sacB gene coding for *Bacillus subtilis* levansucrase. Sucrose-inducible expression results in the formation of levansucrase which catalyses the synthesis of the product levan which is toxic to *C. glutamicum*. Consequently, only those clones in which the integrated pK18mobsacB_IBcg0054_Pg3_argJB has again been excised grow on LB agar containing sucrose. Either the complete cassette IBcg0054_Pg3_argJB or the chromosomal intergenic region IBcg0054 may be excised together with the plasmid. Approximately 40 to 50 colonies were tested for the phenotype "Growth in the presence of sucrose" and "No growth in the presence of kanamycin". In order to establish that the cassette IBcg0054_Pg3_argJB has remained in the chromosome, approximately 20 colonies which have the phenotype 5 "Growth in the presence of sucrose" and "No growth in the presence of kanamycin" were investigated with the aid of the polymerase chain reaction by the standard PCR method of Innis et al. (PCR Protocols. A Guide to Methods and Applications, 1990, Academic Press). This involved amplifying from the chromosomal DNA of the colonies a DNA fragment which carries the surrounding region of the intergenic region IBcg0054 and part of the inserted arg gene. The following primer oligonucleotides were selected for the PCR.

```
argA-E1:
TGTCGCGGAAGTGCTGCAAC cg0054_10.p:
GCACTCTCGTTTGGCAGTTC
```

The correct clones were detected by generating a 1949 bp DNA fragment which was detected in an agarose gel.

Example 8

Preparation of L-ornithine Using *Corynebacterium glutamicum*

To test their ability to produce L-ornithine, in each case three clones of the strain *C. glutamicum* ATCC13032_DargFRGH_Pg3_argJB and three clones of the strain ATCC 13032_Delta_argFRGH were precultured in each case 10 ml of test medium at 33° C. for 16 h. For the production assay, in each case 10 ml of test medium were inoculated with the preculture obtained such that the starting $OD_{600}$ (optical density at 600 nm) was 0.1. Each clone was tested in three shaker flasks, so that each strain is represented by a total of nine shaker flasks.

The test medium was identical to the CgXII medium described in Keilhauer et al. (Journal of Bacteriology (1993) 175: 5593-5603) but additionally contained 7.5 g/l yeast extract (Difco), 25 µg/ml kanamycin, 1 mM IPTG (isopropyl-beta-D-thiogalactopyranoside) and 40 g/l sucrose instead of glucose. For reasons of simplicity, the composition of the test medium is summarized in Table 2 below.

TABLE 2

| Component | Content per 1 |
|---|---|
| $(NH_4)_2SO_4$ | 20 g |
| Urea | 5 g |
| $KH_2PO_4$ | 1 g |
| $K_2HPO_4$ | 1 g |
| $MgSO_4 \times 7 H_2O$ | 0.25 g |
| 3-morpholinopropanesulphonic acid (MOPS) | 42 g |
| $CaCl_2$ | 0.01 g |
| $FeSO_4 \times 7H_2O$ | 0.01 g |
| $MnSO_4 \times H_2O$ | 0.01 g |
| $ZnSO_4 \times 7 H_2O$ | 0.001 g |
| $CuSO_4$ | 0.0002 g |
| $NiCl_2 \times 6H_2O$ | 0.00002 g |
| Biotin | 0.0002 g |
| Protocatechuic acid | 0.03 g |
| Sucrose | 40 g |
| Yeast extract | 7.5 g |
| pH (using NaOH) | 7 |

Culturing was carried out in 100 ml shaker flasks at 33° C. and 200 rpm. The deflection of the shaker was 5 cm. Samples were taken from the cultures after 24 and 48 hours, and the optical density, the sucrose content and the L-ornithine content were determined, and the cells were removed by brief centrifugation (table-top centrifuge type 5415D (Eppendorf) at 13000 rpm, 10 min, room temperature).

The optical density was determined at a wavelength of 660 nm, using a GENios microtitre plate photometer (Tecan, Reading UK). The samples were diluted 1:100 with demineralized water prior to the measurement.

Sucrose was determined using a test system (Cat. No. 10 716 251 035) from R-Biopharm AG (Darmstadt, Germany). This involves inversion of sucrose and the glucose formed being detected using a coupled enzyme assay (hexokinase/glucose-6-phosphate dehydrogenase) via NADH formation.

Quantitative determination of the extracellular amino acid concentrations from the culture supernatent was carried out by means of reversed-phase HPLC (Lindroth et al., Analytical chemistry (1979) 51: 1167-1174), using an HP1100 series HPLC instrument (Hewlett-Packard, Waldbronn, Germany) with connected fluorescence detector (G1321A); system control and data evaluation were carried out using an HP Chem Station (Hewlett-Packard). 1 µl of the amino acid solution to be analysed was mixed in an automated pre-column derivatization with 20 µl of ready-to-use ortho-phthalaldehyde/2-mercaptoethanol reagent (Pierce Europe BV, Oud-Beijerland, Netherlands). The resulting fluorescent, thio-substituted isoindoles (Jones et al., Journal of Chromatography (1983) 266: 471-482) were fractionated on a pre-column (40×4 mm Hypersil ODS 5) and main-column (Hypersil ODS 5) combination (both columns from CS-Chromatographie Service GmbH, Langerwehe, Germany) using a gradient program with an increasingly non-polar phase (methanol). The polar eluent was sodium acetate (0.1 M; pH 7.2); the flow rate was 0.8 ml per minute. Fluorescence of the derivatized amino acids was detected at an excitation wavelength of 230 nm and an emission wavelength of 450 nm. The L-ornithine and/or L-ornithine hydrochloride concentrations were calculated by way of comparison with an external standard and L-asparagine as additional internal standard.

The molecular weight of L-ornithine hydrochloride is 168.6 g×mol$^{-1}$ and that of L-ornithine is 132.1 g×mol$^{-1}$.

The yield was calculated by dividing the amount of L-ornithine formed (measured as L-ornithine hydrochloride) by the amount of sucrose consumed.

The results are depicted in Table 3.

Table 3:

L-ornithine formation after 24 hours (Table 3A) and 48 hours (Table 3B) of incubation. Abbreviations: Orn-HCl: L-ornithine hydrochloride.

TABLE 3A

| Strain | Time 24 hours | | |
|---|---|---|---|
| | Orn-HCl g/l | Yield g/g | OD |
| ATCC 13032_Delta_argFRGH | 9.85 ± 0.10 | 0.39 ± 0.01 | 10.83 ± 0.25 |
| ATCC13032_DargFRGH_Pg3_argJB | 10.53 ± 0.16 | 0.42 ± 0.01 | 10.50 ± 0.45 |

TABLE 3B

| Strain | Time 48 hours | | |
|---|---|---|---|
| | Orn-HCl g/l | Yield g/g | OD |
| ATCC 13032_Delta_argFRGH | 15.10 ± 0.65 | 0.35 ± 0.01 | 11.59 ± 1.20 |
| ATCC13032_DargFRGH_Pg3_argJB | 16.28 ± 0.41 | 0.38 ± 0.01 | 10.88 ± 0.43 |

Example 9

Preparation of the Replacement Constructs pK18mobsacB_homUP_Pg3_hom, pK18mobsacB_ilvAUP_Pg3_ilvA and pK18mobsacB_pycUP_Pg3_pyc Construction of the Replacement Vector pK18mobsacB_homUP_Pg3_hom Starting from the genomic sequence of *Corynebacterium glutamicum* ATCC13032, a 2549 bp DNA fragment was synthesized at GeneArt (Regensburg, Germany) (Seq ID No. 42), which carries a part of the gene region upstream of the hom gene, the Pgap3 promoter and a part of the hom gene. The fragment was cut by BamHI and XbaI cleavage via the terminally introduced cleavage sites BamHI and XbaI and then cloned into the vector pK18mobsacB which had been cut likewise with BamHI and XbaI. The plasmid is named pK18mobsacB_homUP_Pg3_hom.

Construction of the Replacement Vector pK18mobsacB_ilvAUP_Pg3_ilvA

Similarly, a 2442 bp DNA fragment was synthesized at GeneArt (Seq ID No. 43), which carries a part of the gene region upstream of the ilvA gene, the Pgap3 promoter and a part of the ilvA gene. The fragment was cut by BamHI and XbaI cleavage via the terminally introduced cleavage sites BamHI and XbaI and then cloned into the vector pK18mobsacB which had been cut likewise with BamHI and XbaI. The plasmid is named pK18mobsacB_ilvAUP_Pg3_ilvA.

Construction of the Replacement Vector pK18mobsacB_pycUP_Pg3_pyc

Similarly, a 2072 bp DNA fragment was synthesized at GeneArt (Seq ID No. 44), which carries a part of the gene region upstream of the pyc gene, the Pgap3 promoter and a part of the pyc gene. The fragment was cut by BamHI and HindIII=cleavage via the terminally introduced cleavage sites BamHI and HindIII and then cloned into the vector pK18mobsacB which had been cut likewise with BamHI and HindIII. The plasmid is named pK18mobsacB_pycUP_Pg3_pyc.

Example 10

Preparation of the *C. glutamicum* Strains ATCC14310_homUP_Pg3_hom, ATCC14310_ilvAUP_Pg3_ilvA and ATCC14310_pycUP_Pg3_pyc The vectors mentioned in example 9, pK18mobsacB_homUP_Pg3_hom, pK18mobsacB_ilvAUP_Pg3_ilvA and pK18mobsacB_pycUP_Pg3_pyc, were transferred in each case individually by conjugation into the *Corynebacterium glutamicum* strain *C. glutamicum* ATCC14310 (similarly to example 4) by means of conjugation according to a protocol by Schafer et al. (Journal of Microbiology 172: 1663-1666 (1990)).

The following primer oligonucleotides were used for detection PCR of the strains.

Primer for Detecting homUP_Pg3_hom in ATCC14310:

```
Hom_X1-A1
                                       (SEQ ID No. 45)
GATCTAGACGTCCAGGAGTTCCTCTACG

LC-hom2
                                       (SEQ ID No. 46)
TGGCGTCCAAGATGAAGTTG
```

The correct clones were detected by generation of a 1502 bp DNA fragment which was detected in an agarose gel and then confirmed by sequencing.
Primer for Detecting ilvAUP_Pg3_ilvA in ATCC14310:

```
Pgap3_1.p
                                       (SEQ ID No. 47)
CGAGTACTATGCATTGAAGCCTAAAAACGACCG ilvA-int-rev2
                                       (SEQ ID No. 48)
ACCGCGGATCTTGTAGGAAC
```

The correct clones were detected by generation of a 712 bp DNA fragment which was detected in an agarose gel and then confirmed by sequencing.
Primer for Detecting pycUP_Pg3 pyc in ATCC14310:

```
pycUP_3.p
                                       (SEQ ID No. 49)
AGCACGTCAGCTGGTTCA 2xpyc-1
                                       (SEQ ID No. 50)
AGGTACGCCTTGACTGGTGA
```

The correct clones were detected by generation of a 1004 bp DNA fragment which was detected in an agarose gel and then confirmed by sequencing.

Example 11

Production of Isoleucine

In each case, 10 ml of Caso broth containing 0.5% glucose were inoculated with 100 µl of a bacterial culture from example 10 (ATCC 14310 derivatives) in a conical flask with baffles (volume: 100 ml) and shaken at 200 rpm by way of a preculture at 33° C. for 16 h (amplitude: 5 cm). From the preculture, 10 ml of main culture in each of three 100 ml conical flasks with baffles were inoculated with an inoculation volume of 1%. A medium containing 40 g of glucose, 20 g of ammonium sulphate, 0.5 g of potassium dihydrogen phosphate, 0.5 g of dipotassium hydrogen phosphate, 20 g of calcium carbonate, 0.25 g of magnesium sulphate (heptahydrate), 10 mg of iron sulphate (heptahydrate), 10 mg of manganese sulphate (x4H$_2$O), 1 mg of zinc sulphate (heptahydrate), 0.2 mg of copper sulphate and 300 mg/l of L-leucine was used for the main culture. The main culture was incubated at 33° C. and a shaker speed of 200 rpm (amplitude: 5 cm) for 48 h. The culture fluid obtained was removed by centrifugation and the concentration of isoleucine was subsequently determined in the supernatant. Table 4 depicts the results.

TABLE 4

Production of L-isoleucine after 48 hours of incubation

| | Isoleucine conc. (g/l) after 48 h | | |
|---|---|---|---|
| Strain | Culture 1 | Culture 2 | Culture 3 |
| ATCC14310 | 3.51 | 3.43 | 3.48 |
| ATCC14310_homUP_Pg3_hom | 3.91 | 3.95 | 3.97 |
| ATCC14310_ilvAUP_Pg3_ilvA | 4.1 | 4.02 | 4.05 |
| ATCC14310_pycUP_Pg3_pyc | 3.75 | 3.81 | 3.84 |

The abbreviations and names used have the following meaning.
oriV: ColE1-like origin from pMB1
sacB: the sacB gene coding for the protein levansucrase
RP4mob: RP4-mobilization site
Kan: Kanamycin-resistance gene
'cg0057: Part of the cg0057 gene coding for a serine/threonine protein kinase
cg0055: cg0055 gene coding for a putative membrane protein
'cg0054: Part of the cg0054 gene coding for an iron-uptake protein
gap Terminator: Termination sequence of the gap gene
promoter: Promoter of the gap gene corresponding to SEQ ID No. 3 (also P gap 3)
gap RBS: Ribosome-binding site of the gap gene
lysC: Allele of the lysC gene, coding for a densensitized aspartate kinase
asd: asd gene coding for an aspartate-semialdehyde dehydrogenase
argJ: argJ gene coding for a glutamate N-acetyltransferase
argB: argB gene coding for an acetylglutamate kinase
homUP: part of the gene region upstream of the hom gene
hom': part of the hom gene coding for a homoserine dehydrogenase
ilvAUP: part of the gene region upstream of the ilvA gene
ilvA': part of the ilvA gene coding for a threonine dehydratase
pycUP: part of the gene region upstream of the pyc gene
pyc': part of the pyc gene coding for a pyruvate carboxylase
HindIII: Cleavage site of the HindIII=restriction enzyme
BamHI: Cleavage site of the BamHI restriction enzyme
XbaI: Cleavage site of the XbaI restriction enzyme
AvrII: Cleavage site of the AvrII restriction enzyme
NsiI: Cleavage site of the NsiI restriction enzyme
SphI: Cleavage site of the SphI restriction enzyme
BlnI: Cleavage site of the BlnI restriction enzyme

The invention claimed is:

1. An isolated polynucleotide having promoter activity, which comprises SEQ ID NO: 3 or SEQ ID NO: 34.

2. The polynucleotide according to claim 1, which consists of the nucleotide sequence depicted in SEQ ID NO: 3 or SEQ ID NO: 34.

3. The polynucleotide according to claim 1, which is functionally linked at the 3' end to a second polynucleotide which comprises an ATG or GTG start codon at the 5' end and the second polynucleotide codes for one or more polypeptides, wherein said link is a direct link, a link through a linker oligonucleotide, or a link through a linker polynucleotide.

4. The polynucleotide according to claim 3, wherein the polynucleotide of SEQ ID NO: 3 or SEQ ID NO: 34 is linked through the adenosine nucleotide in position 461 at the 3' end of SEQ ID NO: 3 or SEQ ID NO: 34 by a linker oligonucleotide of 1, 2, 3, 4 or 5 nucleotides in length to the first nucleotide of the start codon of the second polynucleotide.

5. The polynucleotide according to claim 3, wherein the polynucleotide of SEQ ID NO: 3 or SEQ ID NO: 34 is linked through the adenosine nucleotide at its 3' end, by a linker polynucleotide of from 6 to 600 nucleotides in length to the first nucleotide of the start codon of the second polynucleotide.

6. The polynucleotide according to claim 5, wherein the linker polynucleotide comprises a nucleotide sequence which ensures translation of RNA transcribed from the polynucleotide.

7. The polynucleotide according to claim 5, wherein the sequence of the linker polynucleotide is SEQ ID NO: 12 or SEQ ID NO: 13.

8. The polynucleotide according to claim 5, wherein the sequence of the linker polynucleotide is SEQ ID NO: 14, SEQ ID NO: 15, SEQ ID NO: 16, SEQ ID NO: 17 or SEQ ID NO: 18.

9. A polynucleotide according to claim 2, which is functionally linked through the adenosine nucleotide in position 461 at the 3' end of SEQ ID NO: 3 or SEQ ID NO: 34 to a linker oligonucleotide or to a linker polynucleotide which ensures translation of RNA.

10. The polynucleotide according to claim 3, wherein the second polynucleotide which codes for one or more polypeptides is selected from the group consisting of:
 a) Polynucleotide (zwf gene) coding for the Zwf subunit of glucose-6-phosphate 1-dehydrogenase (Zwf),
 b) Polynucleotide (opcA gene) coding for the OpcA subunit of glucose-6-phosphate 1-dehydrogenase (OpcA), c) Polynucleotide (devB gene) coding for a 6-phosphogluconolactonase (DevB),
d) Polynucleotide (tkt gene) coding for a transketolase (Tkt),
e) Polynucleotide (tal gene) coding for a transaldolase (Tal),
f) Polynucleotide (gnd gene) coding for a 6-phosphogluconate dehydrogenase (Gnd),
g) Polynucleotide (rpe gene) coding for a ribulose-phosphate 3-epimerase (Rpe),
h) Polynucleotide (rpi gene) coding for a ribose-5-phosphate isomerase B (Rpi),
i) Polynucleotide (ppc gene) coding for a phosphoenolpyruvate carboxylase (Ppc),
j) Polynucleotide (fbp gene) coding for a fructose 1,6-bisphosphatase (Fbp),
k) Polynucleotide (pyc gene) coding for a pyruvate carboxylase (Pyc),
l) Polynucleotide (dapA gene) coding for a dihydrodipicolinate synthase (DapA),
m) Polynucleotide (asd gene) coding for an aspartate-semialdehyde dehydrogenase (Asd),
n) Polynucleotide (ddh gene) coding for a meso-diaminopimelate dehydrogenase (Ddh),
o) Polynucleotide (lysA gene) coding for a diaminopimelate decarboxylase (LysA),
p) Polynucleotide (aat gene) coding for an aspartate aminotransferase (Aat),
q) Polynucleotide (lysE gene) coding for a polypeptide having L-lysine-export activity (LysE),
r) Polynucleotide (dapB gene) coding for a dihydrodipicolinate reductase (DapB),
s) Polynucleotide (lysC gene) coding for an aspartate kinase (LysC),
t) Polynucleotide (dapC gene) coding for a succinyldiaminopimelate aminotransferase, AT class I (DapC),
u) Polynucleotide (dapD gene) coding for a tetrahydrodipicolinate succinylase (DapD),
v) Polynucleotide (dapE gene) coding for a succinyl-di-aminopimelate desuccinylase (DapE),
w) Polynucleotide (dapF gene) coding for a diaminopimelate epimerase (DapF),
x) Polynucleotides (ilvB gene and ilvN gene) coding for the subunits of an acetolactate synthase (IIvBN),
y) Polynucleotide (ilvC gene) coding for an isomeroreductase (IlvC),
z) Polynucleotide (ilvD gene) coding for a dihydroxy-acid dehydratase (IlvD),
aa) Polynucleotide (ilvE gene) coding for a transaminase (IlvE),
bb) Polynucleotide (ilvA gene) coding for a threonine dehydratase (IlvA),
cc) Polynucleotide (horn gene) coding for a homoserine dehydrogenase (Hom),
dd) Polynucleotide (thrB gene) coding for a homoserine kinase (ThrB),
ee) Polynucleotide (thrC gene) coding for a threonine synthase (ThrC),
ff) Polynucleotide (leuA gene) coding for an isopropylmalate synthase (LeuA),
gg) Polynucleotide (leuB gene) coding for an isopropylmalate dehydrogenase (LeuB),
hh) Polynucleotide (leuC gene) coding for the large subunit of an isopropylmalate isomerase (LeuC),
ii) Polynucleotide (leuD gene) coding for the small subunit of an isopropylmalate isomerase (LeuD),
jj) Polynucleotide (lysE gene) coding for a lysine/ornithine transporter,
kk) Polynucleotide (argB gene) coding for an N-acetylglutamate kinase (ArgB),
ll) Polynucleotide (gdh gene) coding for a glutamate dehydrogenase (Gdh),
mm) Polynucleotide (argJ gene) coding for a glutamate N-acetyltransferase (ArgJ),
nn) Polynucleotide (argC gene) coding for an N-acetyl-gamma-glutamyl-phosphate reductase (ArgC), and
oo) Polynucleotide (argD gene) coding for an acetylornithine aminotransferase (ArgD).

\* \* \* \* \*